(12) United States Patent (10) Patent No.: US 12,629,141 B2

Bambury et al. (45) Date of Patent: May 19, 2026

(54) IMPLANT FOR CLOSING AN OPENING IN TISSUE

(71) Applicant: Signum Surgical Limited, Galway (IE)

(72) Inventors: Eoin Bambury, Galway (IE); Moshe Zilversmit, Campbell, CA (US); Michael Schaller, Louisville, CO (US); Scott Early, Redwood City, CA (US); Ciaran O'Sullivan, County Galway (IE)

(73) Assignee: Signum Surgical Limited, Galway (IE)

( * ) Notice: Subject to any disclaimer, the term of this patent is extended or adjusted under 35 U.S.C. 154(b) by 0 days.

(21) Appl. No.: 17/865,838

(22) Filed: Jul. 15, 2022

(65) Prior Publication Data

US 2022/0361863 A1 Nov. 17, 2022

Related U.S. Application Data

(63) Continuation of application No. 16/706,294, filed on Dec. 6, 2019, now Pat. No. 11,452,512, which is a (Continued)

(30) Foreign Application Priority Data

Oct. 6, 2017 (EP) ..................................... 17195342
Oct. 20, 2017 (EP) ..................................... 17197528
(Continued)

(51) Int. Cl.
*A61B 17/00* (2006.01)
*A61B 17/12* (2006.01)

(52) U.S. Cl.
CPC ..................... *A61B 17/0057* (2013.01); *A61B 2017/00004* (2013.01); *A61B 2017/00579* (2013.01);
(Continued)

(58) Field of Classification Search
CPC ............ A61B 17/0057; A61B 17/0644; A61B 17/0469; A61B 17/0412; A61B 17/0487;
(Continued)

(56) References Cited

U.S. PATENT DOCUMENTS 3,877,434 A * 4/1975 Ferguson ........... A61B 17/0485
606/139
4,204,541 A * 5/1980 Kapitanov ........... A61B 17/064
606/221
(Continued)

FOREIGN PATENT DOCUMENTS

CN 101347348 A 1/2009
CN 102327135 A 1/2012
(Continued)

OTHER PUBLICATIONS

Absorv®—Bioabsorbable Extrusions, http:/www.zeusinc.com/advanced-products/absory-bioabsorbable. Aug. 11, 2017 (7 pages).
(Continued)

*Primary Examiner* — Kathleen S Holwerda
(74) *Attorney, Agent, or Firm* — Bookoff McAndrews, PLLC

(57) ABSTRACT

An implant 801 for closing an opening in tissue such as a fistula or a sinus comprises a coil having a substantially uniform outer diameter. The coil forms an internal passage having a diameter that tapers from a distal end to a proximal end. The implant 801 may be delivered using a non-tapered driver coil 820.

19 Claims, 70 Drawing Sheets

Related U.S. Application Data continuation of application No. PCT/EP2018/065246, filed on Jun. 8, 2018.

(60) Provisional application No. 62/517,553, filed on Jun. 9, 2017.

(30) Foreign Application Priority Data

| | | | |
|---|---|---|---|
| Dec. 21, 2017 | (EP) | ...................................... | 17209834 |
| May 4, 2018 | (EP) | ...................................... | 18170943 |

(52) U.S. Cl.
CPC .............. *A61B 2017/00623* (2013.01); *A61B 2017/00641* (2013.01)

(58) Field of Classification Search
CPC ... A61B 17/064; A61B 17/068; A61B 17/862; A61B 17/8634; A61B 17/869; A61B 17/0401; A61B 2017/0414; A61B 2017/0409; A61B 2017/0464; A61B 2017/0496; A61B 2017/0412; A61B 2017/0647; A61B 2017/0649; A61B 2017/0641; A61B 2017/0427; A61B 2017/0429; A61B 2017/0435; A61B 2017/0437; A61B 2017/06076; A61B 2017/00641; A61B 2017/00623; A61B 2017/0068; A61B 2017/00579; A61B 17/0485; A61B 17/12; A61F 2002/0847–087
See application file for complete search history.

(56) References Cited

U.S. PATENT DOCUMENTS

| | | | | |
|---|---|---|---|---|
| 4,745,919 | A | | 5/1988 | Bundy et al. |
| 5,108,420 | A | | 4/1992 | Marks |
| 5,309,927 | A | | 5/1994 | Welch |
| 5,330,503 | A | | 7/1994 | Yoon |
| 5,476,505 | A | | 12/1995 | Limon |
| 5,582,616 | A | * | 12/1996 | Bolduc ................ A61B 17/064 |
| | | | | 606/139 |
| 5,628,762 | A | | 5/1997 | Al-Tameem |
| 5,643,305 | A | | 7/1997 | Al-Tameem |
| 5,645,565 | A | | 7/1997 | Rudd et al. |
| 5,782,844 | A | * | 7/1998 | Yoon ................... A61B 17/064 |
| | | | | 606/139 |
| 5,810,851 | A | | 9/1998 | Yoon |
| 5,810,882 | A | | 9/1998 | Bolduc et al. |
| 5,824,008 | A | | 10/1998 | Bolduc et al. |
| 5,904,696 | A | | 5/1999 | Rosenman |
| 5,964,772 | A | | 10/1999 | Bolduc et al. |
| 5,972,001 | A | | 10/1999 | Yoon |
| 6,010,517 | A | | 1/2000 | Baccaro |
| 6,059,825 | A | | 5/2000 | Hobbs et al. |
| 6,080,182 | A | | 6/2000 | Shaw et al. |
| 6,083,244 | A | | 7/2000 | Lubbers et al. |
| 6,245,079 | B1 | | 6/2001 | Nobles et al. |
| 6,296,656 | B1 | | 10/2001 | Bolduc et al. |
| 6,375,671 | B1 | | 4/2002 | Kobayashi et al. |
| 6,537,300 | B2 | | 3/2003 | Girton |
| 6,551,319 | B2 | | 4/2003 | Lieberman |
| 6,562,051 | B1 | | 5/2003 | Bolduc et al. |
| 6,663,633 | B1 | | 12/2003 | Pierson, III |
| 6,790,218 | B2 | | 9/2004 | Jayaraman |
| 6,884,248 | B2 | | 4/2005 | Bolduc et al. |
| 6,984,221 | B1 | | 1/2006 | Scheye |
| 7,077,850 | B2 | | 7/2006 | Kortenbach |
| 7,115,274 | B2 | | 10/2006 | Keller et al. |
| 7,189,251 | B2 | | 3/2007 | Kay |
| 7,485,087 | B2 | | 2/2009 | Burgard |
| 7,645,229 | B2 | | 1/2010 | Armstrong |

| | | | |
|---|---|---|---|
| 7,811,295 | B2 | 10/2010 | Kortenbach |
| D629,899 | S | 12/2010 | Meinero |
| 7,897,167 | B2 | 3/2011 | Armstrong et al. |
| 8,177,809 | B2 | 5/2012 | Mavani et al. |
| 8,206,416 | B2 | 6/2012 | Mavani et al. |
| 8,221,451 | B2 | 7/2012 | Mavani et al. |
| 8,377,094 | B2 | 2/2013 | Mavani et al. |
| 8,414,634 | B2 | 4/2013 | Sekido et al. |
| 8,465,516 | B2 | 6/2013 | Pavcnik et al. |
| 8,486,155 | B2 | 7/2013 | McAlister et al. |
| 8,491,256 | B2 | 7/2013 | Cronin et al. |
| 8,501,217 | B2 | 8/2013 | Armstrong et al. |
| 8,535,349 | B2 | 9/2013 | Chen et al. |
| 8,556,930 | B2 | 10/2013 | Ellingwood |
| 8,568,446 | B2 | 10/2013 | Kurokawa et al. |
| 8,579,919 | B2 | 11/2013 | Bolduc et al. |
| 8,623,049 | B2 | 1/2014 | Ward |
| 8,647,351 | B2 | 2/2014 | Kortenbach |
| 8,685,072 | B2 | 4/2014 | Neuberger |
| 8,702,644 | B2 | 4/2014 | Hall et al. |
| 8,764,791 | B2 | 7/2014 | Armstrong |
| 8,784,436 | B2 | 7/2014 | Ho et al. |
| 8,840,917 | B2 | 9/2014 | Armstrong et al. |
| 8,858,546 | B2 | 10/2014 | Hall et al. |
| 8,915,941 | B2 | 12/2014 | Obermiller |
| 8,932,325 | B2 | 1/2015 | Stanley et al. |
| 8,936,616 | B2 | 1/2015 | Nelson |
| 8,986,331 | B2 | 3/2015 | Chekan et al. |
| 9,113,851 | B2 | 8/2015 | Agnew |
| 9,131,941 | B2 | 9/2015 | Carrison et al. |
| 9,138,210 | B2 | 9/2015 | Schulte et al. |
| 9,149,262 | B2 | 10/2015 | Obermiller et al. |
| 9,211,116 | B2 | 12/2015 | Carrison et al. |
| 9,226,736 | B2 | 1/2016 | Obermiller et al. |
| 9,277,904 | B2 | 3/2016 | Paul, Jr. et al. |
| 9,345,476 | B2 | 5/2016 | Surti |
| 9,433,410 | B2 | 9/2016 | Kortenbach |
| 9,456,813 | B2 | 10/2016 | Obermiller et al. |
| 9,456,815 | B2 | 10/2016 | Armstrong et al. |
| 9,474,514 | B2 | 10/2016 | Agnew et al. |
| 9,492,149 | B2 | 11/2016 | Obermiller et al. |
| 9,526,484 | B2 | 12/2016 | Armstrong |
| 9,532,773 | B2 | 1/2017 | Jimenez et al. |
| 9,538,996 | B2 | 1/2017 | Patel et al. |
| 9,572,556 | B2 | 2/2017 | Obermiller et al. |
| 9,585,647 | B2 | 3/2017 | Clark |
| 9,615,830 | B2 | 4/2017 | Ranucci et al. |
| 9,675,343 | B2 | 6/2017 | Ostrovsky et al. |
| 9,675,353 | B2 | 6/2017 | Ranucci et al. |
| 9,687,215 | B2 | 6/2017 | Obermiller et al. |
| 9,724,082 | B2 | 8/2017 | Stanley et al. |
| 9,763,882 | B2 | 9/2017 | Halskov et al. |
| 9,788,821 | B2 | 10/2017 | Johnson et al. |
| 9,788,839 | B2 | 10/2017 | Lagodzki et al. |
| 9,801,617 | B2 | 10/2017 | Blom |
| 9,861,517 | B2 | 1/2018 | Pavcnik et al. |
| 9,907,885 | B2 | 3/2018 | Keighley |
| 9,956,315 | B2 | 5/2018 | Patel et al. |
| 9,962,144 | B2 | 5/2018 | Ellingwood |
| 9,993,235 | B2 | 6/2018 | Mavani et al. |
| 10,080,863 | B2 | 9/2018 | Kullas et al. |
| 10,143,457 | B2 | 12/2018 | Agnew |
| 10,342,523 | B2 | 7/2019 | Obermiller et al. |
| 10,357,232 | B2 | 7/2019 | Jimenez et al. |
| 10,363,030 | B2 | 7/2019 | Ranucci et al. |
| 10,368,870 | B2 | 8/2019 | Ranucci et al. |
| 10,383,653 | B2 | 8/2019 | Tasci |
| 10,398,419 | B2 | 9/2019 | Blom |
| 10,441,256 | B2 | 10/2019 | Paul, Jr. et al. |
| 10,470,749 | B2 | 11/2019 | Obermiller et al. |
| 10,617,644 | B2 | 4/2020 | Halskov et al. |
| 10,624,639 | B2 | 4/2020 | Ranucci et al. |
| 10,646,225 | B2 | 5/2020 | Ranucci et al. |
| 10,675,030 | B2 | 6/2020 | Ziniti et al. |
| 10,842,475 | B2 | 11/2020 | Horeman et al. |
| 2002/0183786 | A1 | 12/2002 | Girton |
| 2002/0193808 | A1 | 12/2002 | Belef et al. |
| 2004/0069312 | A1 | 4/2004 | Ohmi |
| 2004/0147957 | A1 | 7/2004 | Pierson, III |

(56) References Cited

U.S. PATENT DOCUMENTS

| | | |
|---|---|---|
| 2004/0193217 A1 | 9/2004 | Lubbers et al. |
| 2005/0004926 A1 | 1/2005 | Ohtani |
| 2005/0010275 A1 | 1/2005 | Sahatjian et al. |
| 2005/0038460 A1 | 2/2005 | Jayaraman |
| 2005/0049626 A1 | 3/2005 | Burgard |
| 2005/0159776 A1 | 7/2005 | Armstrong |
| 2005/0182495 A1 | 8/2005 | Perrone |
| 2005/0187568 A1 | 8/2005 | Klenk et al. |
| 2005/0251201 A1 | 11/2005 | Roue et al. |
| 2006/0074447 A2 | 4/2006 | Armstrong |
| 2006/0280720 A1 | 12/2006 | Fitz et al. |
| 2007/0083230 A1 | 4/2007 | Javois |
| 2007/0088445 A1 | 4/2007 | Patel et al. |
| 2007/0129757 A1 | 6/2007 | Armstrong |
| 2007/0179507 A1 | 8/2007 | Shah |
| 2007/0198059 A1 | 8/2007 | Patel et al. |
| 2007/0248640 A1 | 10/2007 | Karabey et al. |
| 2008/0004640 A1* | 1/2008 | Ellingwood ....... A61B 17/0057 606/151 |
| 2008/0004657 A1 | 1/2008 | Obermiller et al. |
| 2008/0051831 A1 | 2/2008 | Deal et al. |
| 2008/0097523 A1 | 4/2008 | Bolduc et al. |
| 2008/0208265 A1 | 8/2008 | Frazier et al. |
| 2008/0215076 A1 | 9/2008 | Baker |
| 2008/0245374 A1 | 10/2008 | Agnew |
| 2008/0275402 A1 | 11/2008 | Schnell |
| 2009/0069843 A1 | 3/2009 | Agnew |
| 2009/0112238 A1 | 4/2009 | Pitts et al. |
| 2009/0118776 A1 | 5/2009 | Kelsch et al. |
| 2009/0157101 A1 | 6/2009 | Reyes et al. |
| 2009/0326577 A1 | 12/2009 | Johnson et al. |
| 2010/0001038 A1 | 1/2010 | Levin |
| 2010/0030319 A1 | 2/2010 | Weber |
| 2010/0049246 A1 | 2/2010 | Obermiller et al. |
| 2010/0076463 A1 | 3/2010 | Mavani et al. |
| 2010/0082056 A1 | 4/2010 | Mavani et al. |
| 2010/0249830 A1 | 9/2010 | Nelson |
| 2010/0274266 A1 | 10/2010 | Rimer et al. |
| 2011/0046607 A1 | 2/2011 | Halevy |
| 2011/0054413 A1 | 3/2011 | Romhild et al. |
| 2011/0054492 A1 | 3/2011 | Clark |
| 2011/0054520 A1 | 3/2011 | Deal et al. |
| 2011/0060362 A1 | 3/2011 | Patel et al. |
| 2011/0238088 A1 | 9/2011 | Bolduc et al. |
| 2011/0282334 A1 | 11/2011 | Groenhoff |
| 2011/0282368 A1 | 11/2011 | Swayze et al. |
| 2011/0282368 A1 | 11/2011 | Cronin et al. |
| 2011/0282381 A1 | 11/2011 | Cronin et al. |
| 2011/0295282 A1 | 12/2011 | Glick et al. |
| 2012/0035644 A1 | 2/2012 | Eskaros et al. |
| 2012/0046690 A1 | 2/2012 | Blom |
| 2012/0101526 A1 | 4/2012 | Bennett |
| 2012/0101534 A1 | 4/2012 | Pitbladdo |
| 2012/0179199 A1 | 7/2012 | Hernandez et al. |
| 2012/0323271 A1 | 12/2012 | Obermiller et al. |
| 2013/0158595 A1 | 6/2013 | Mavani et al. |
| 2013/0237816 A1 | 9/2013 | Armstrong |
| 2013/0338706 A1 | 12/2013 | Jimenez et al. |
| 2014/0018850 A1 | 1/2014 | Ellingwood |
| 2014/0200604 A1 | 7/2014 | Carrison et al. |
| 2014/0227337 A1 | 8/2014 | Keighley |
| 2014/0243794 A1 | 8/2014 | Halskov et al. |
| 2014/0257376 A1 | 9/2014 | Armstrong |
| 2014/0277116 A1 | 9/2014 | Stanley et al. |
| 2014/0288491 A1 | 9/2014 | Halskov et al. |
| 2014/0303603 A1 | 10/2014 | Kullas et al. |
| 2014/0379025 A1 | 12/2014 | Carrison et al. |
| 2014/0379026 A1 | 12/2014 | Carrison et al. |
| 2015/0045612 A1 | 2/2015 | Ostrovsky et al. |
| 2015/0073471 A1 | 3/2015 | Clark |
| 2015/0230802 A1 | 8/2015 | Lagodzki et al. |
| 2015/0250460 A1 | 9/2015 | Horeman et al. |
| 2015/0297807 A1 | 10/2015 | Leblanc et al. |
| 2016/0000416 A1 | 1/2016 | Carrison et al. |
| 2016/0000507 A1 | 1/2016 | Neuberger |
| 2016/0007978 A1 | 1/2016 | Obermiller et al. |
| 2016/0038128 A1 | 2/2016 | Carrison |
| 2016/0143656 A1 | 5/2016 | Tasci |
| 2016/0157840 A1 | 6/2016 | Carrison et al. |
| 2016/0166380 A1 | 6/2016 | Seguin et al. |
| 2016/0184069 A1 | 6/2016 | Lv et al. |
| 2016/0189107 A1 | 6/2016 | Liu |
| 2016/0213361 A1 | 7/2016 | Litvack et al. |
| 2016/0262737 A1 | 9/2016 | Paul et al. |
| 2017/0000469 A1 | 1/2017 | Agnew et al. |
| 2017/0020499 A1 | 1/2017 | Carrison et al. |
| 2017/0086808 A1 | 3/2017 | Patel et al. |
| 2017/0245847 A1 | 8/2017 | Obermiller et al. |
| 2017/0311937 A1 | 11/2017 | Bambury et al. |
| 2018/0021028 A1 | 1/2018 | Emerson et al. |
| 2018/0207098 A1 | 7/2018 | Halskov et al. |
| 2018/0236146 A1 | 8/2018 | Carrison et al. |
| 2018/0325506 A1 | 11/2018 | Ellingwood |
| 2018/0361113 A1 | 12/2018 | Kullas et al. |
| 2019/0269389 A1 | 9/2019 | Horeman et al. |
| 2019/0282229 A1 | 9/2019 | Ranucci et al. |
| 2019/0290277 A1 | 9/2019 | Ranucci et al. |
| 2020/0205832 A1 | 7/2020 | Ranucci et al. |
| 2020/0237374 A1 | 7/2020 | Ranucci et al. |
| 2020/0246006 A1 | 8/2020 | Ziniti et al. |
| 2020/0330652 A1 | 10/2020 | Jessop |

FOREIGN PATENT DOCUMENTS

| | | |
|---|---|---|
| CN | 102802544 A | 11/2012 |
| CN | 103298414 A | 9/2013 |
| CN | 105007832 A | 10/2015 |
| EP | 2628453 A1 | 8/2013 |
| JP | 2015080556 A | 4/2015 |
| WO | WO 96/03925 A1 | 2/1996 |
| WO | WO 97/07744 A1 | 3/1997 |
| WO | WO 97/32526 A1 | 9/1997 |
| WO | WO 00/69345 | 11/2000 |
| WO | WO 2007/090150 A2 | 8/2007 |
| WO | WO 2011/057299 A2 | 5/2011 |
| WO | WO 2013/005752 A1 | 1/2013 |
| WO | WO 2014/117087 | 7/2014 |
| WO | WO 2015/132439 A1 | 9/2015 |
| WO | 2016056016 A1 | 4/2016 |
| WO | 2016189107 A1 | 12/2016 |
| WO | WO 2016/189107 | 12/2016 |

OTHER PUBLICATIONS

Chew, J., "Relieving that pain in the butt (Straits Times, Mind Your Body)," Singapore General Hospital, Mar. 21, 2013, 3 pages, http://www.sgh.com.sg/.

Dudukgain, H. et al., "Why do we have so much trouble treating anal fistula," World Journal of Gastroenterology, Jul. 28, 2011, vol. 17, Issue 28, pp. 3292-3296, http:/wjgnet.com/1007-9327office.

Lewis, R et al., "Novel biological strategies in the management of anal fistula," Colorectal Disease, The Association of Coloproctology of Great Britain and Ireland, Aug. 10, 2012, pp. 1445-1455.

Parks, A.G., et al. "A classification of fistula-in-ano," The British Journal of Surgery, Jan. 1976, vol. 63, No. 1, pp. 1-12.

Vasilevsky, M.D, CA et al., "The Incidence of Recurrent Abscesses or Fistula-in-ano Following Anorectal Suppuration," Diseases of the Colon & Rectum, 1984; Issue 27, pp. 126-130.

"Our purpose is to advance innovation in surgery," last updated Aug. 14, 2017, 2 pages, www.ethicon.com/healthcare-professionals/products.

Wilhelm, Dr. A, "FILAC Fistula-tract Laser Closure," 3 pages.

Villanueva-Herrero, Dr. Juan Antonio "Silicone disk to seal & Collagen matrices to heal Fistula Tracts," 2 pages, http://mintcare.sg/product_category/curaseal/.

"Peramacol™ Collagen Paste for Anorectal Fistula Repair" 4 pages, http://www.hungaronotes.hu/minden/notes2016/kiallitok/covidien2.pdf, 2013 Covidien 5.13 M130535.

Stamos, MD Michael J. et al. "Advances in Anal Fistula Repair: Minimizing Risk for Incontinence," General Surgery News, Dec. 2010, 4 pages.

(56) References Cited

OTHER PUBLICATIONS

"New Technique for Anal Fistula Showing Success" GeneralSurgeryNews.com, Special Report May 2006, 4 pages.

"OTSC Proctology in the treatment of anorectal fistulas," vol. 2 Anorectal Fistula, 2 pages, Oct. 10, 2012.

Piercarlo Meinero, M.D. "VAAFT: Video-Assisted Anal Fistula Treatment with closure of the internal fistula opening by stapler—the MEINERO Technique," 24 pages, www.karlstorz.com, 2011.

Julián Panés et al. "Expanded allogeneic adipose-derived mesenchymal stem cells (Cx601) for complex perianal fistulas in Crohn's disease: a phase 3 randomised, double-blind controlled trial," Jul. 28, 2016, http://dx.doi.org/10.1016/S0140-6736(16)31203-x, 10 pages.

Sep. 9, 2019 Search Report issued in European Patent Application No. 19186010.5. (8 pages).

http://www.ethicon.com/healthcare-professionals/products Retrieved on Jun. 29, 2019.

http://www.zeusinc.com/advanced-products/absorv-bioabsorbables Retrieved on Jun. 25, 2019.

Extended European search report in corresponding European Application No. 21150724.9, dated May 11, 2021 (10 pages).

* cited by examiner

111

107

101

108

110

110

110

102

117

117

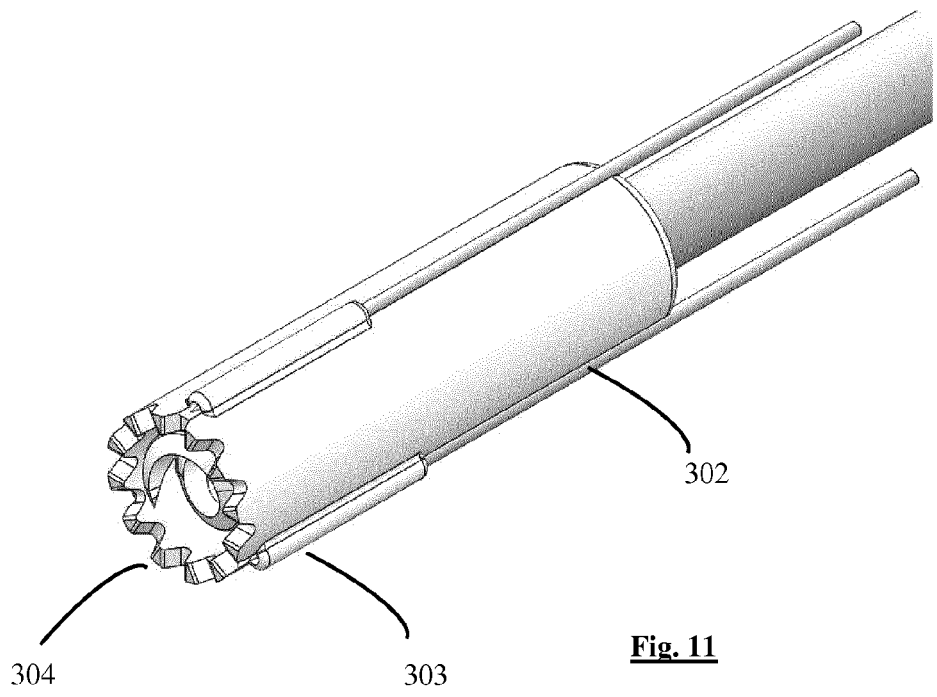
304          303          Fig. 11
302
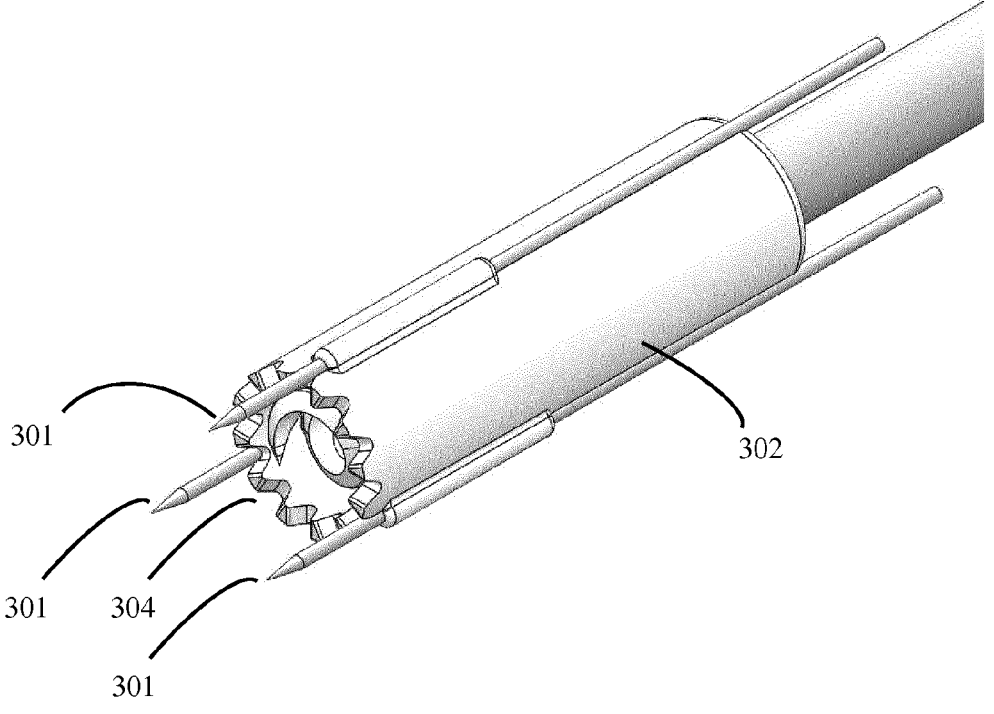
301          302
301     304
301
Fig. 12

400

Height = 13mm

Pitch = 3.75mm
Number of Turns = 2.75
Wall Thickness = 1.1mm

400
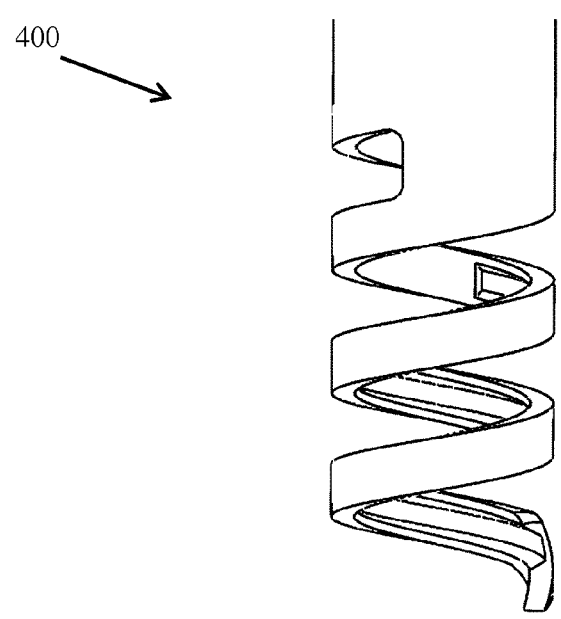
Fig. 14
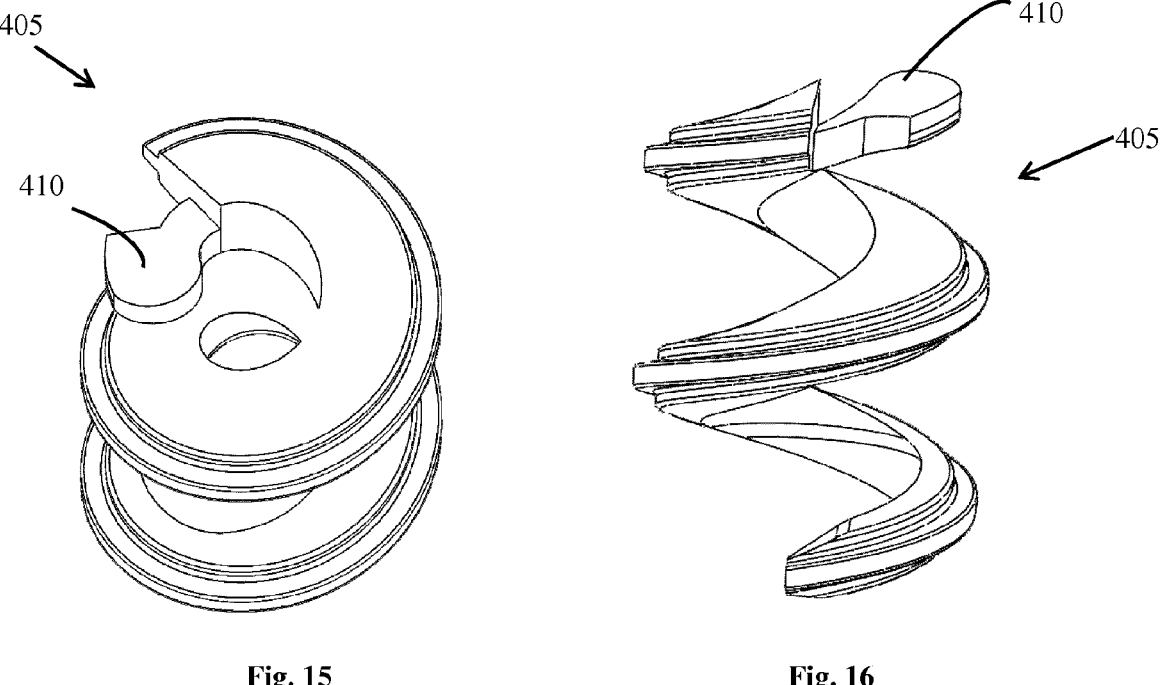
Fig. 15
Fig. 16

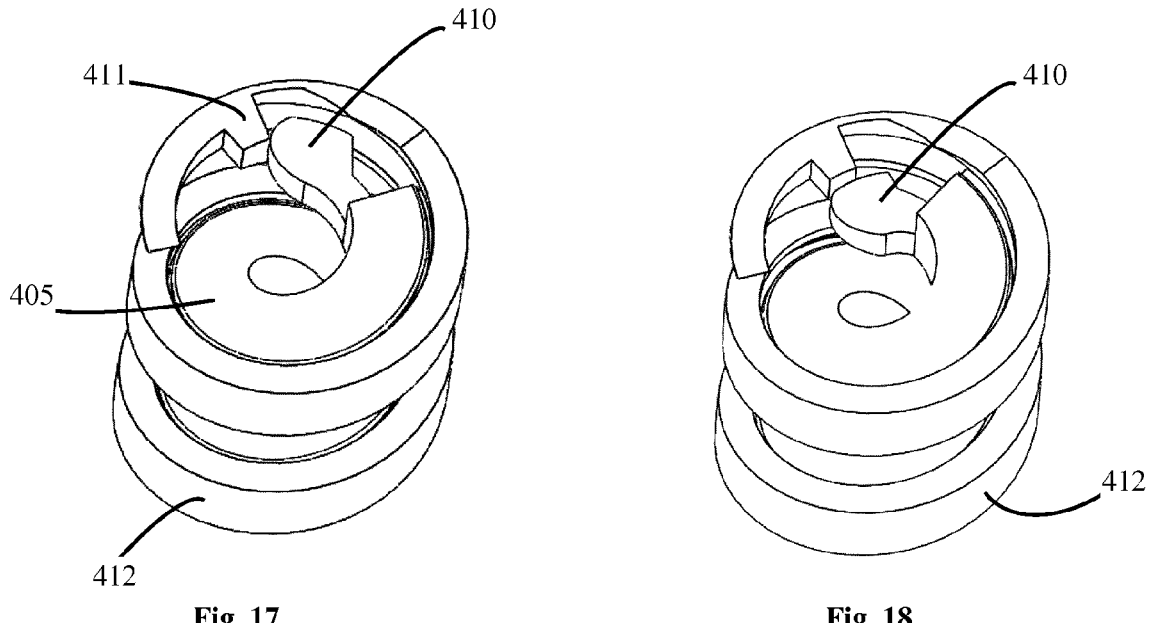
Fig. 17                                Fig. 18
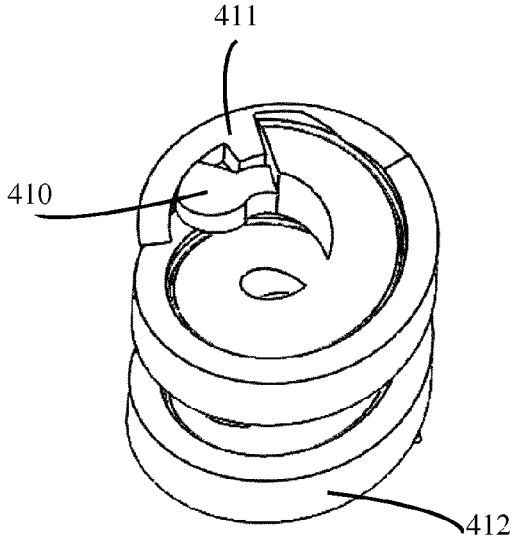
Fig. 19

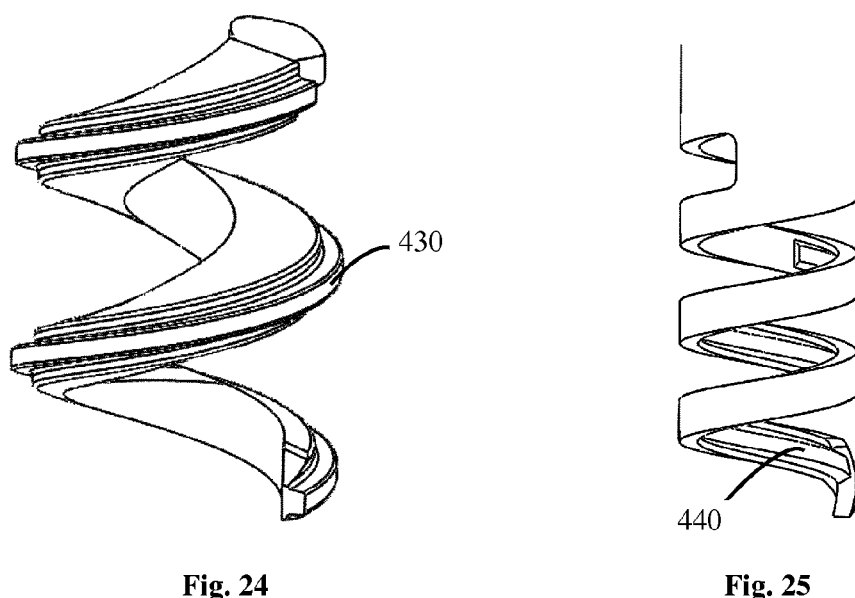
430
Fig. 24
440
Fig. 25
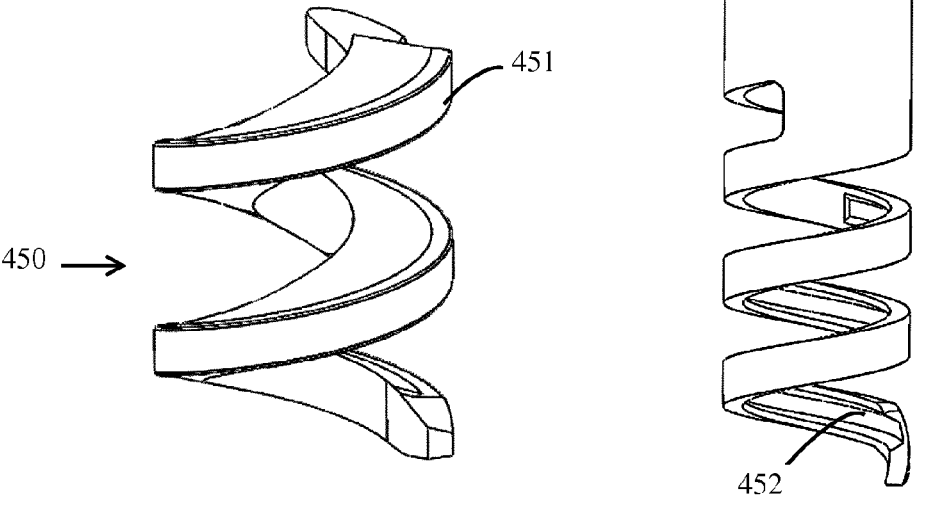
451
450 →
Fig. 26
452
Fig. 27

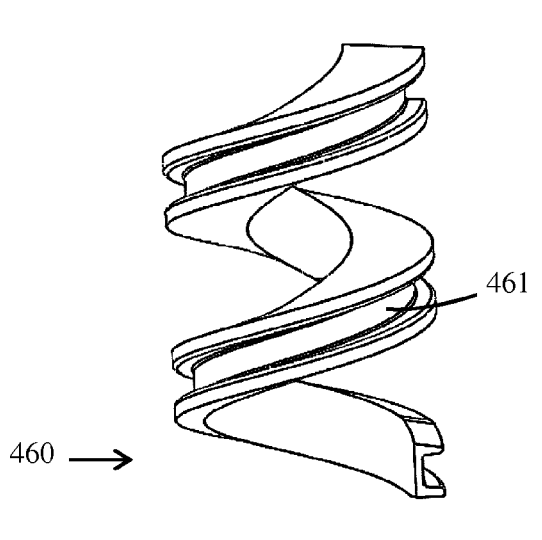
461
460 →
Fig. 28
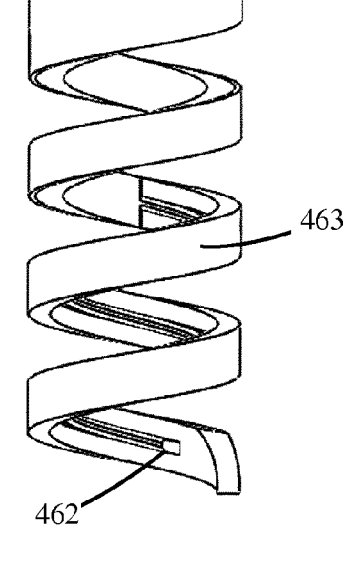
463
462
Fig. 29
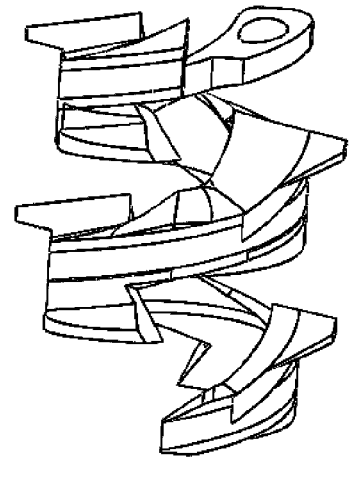
Fig. 30
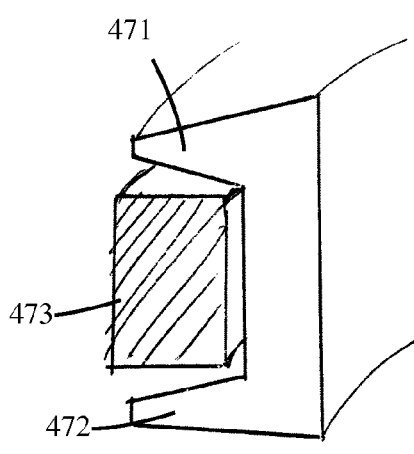
471
473
472
Fig. 31

471
473
472

471
473
472

480

480

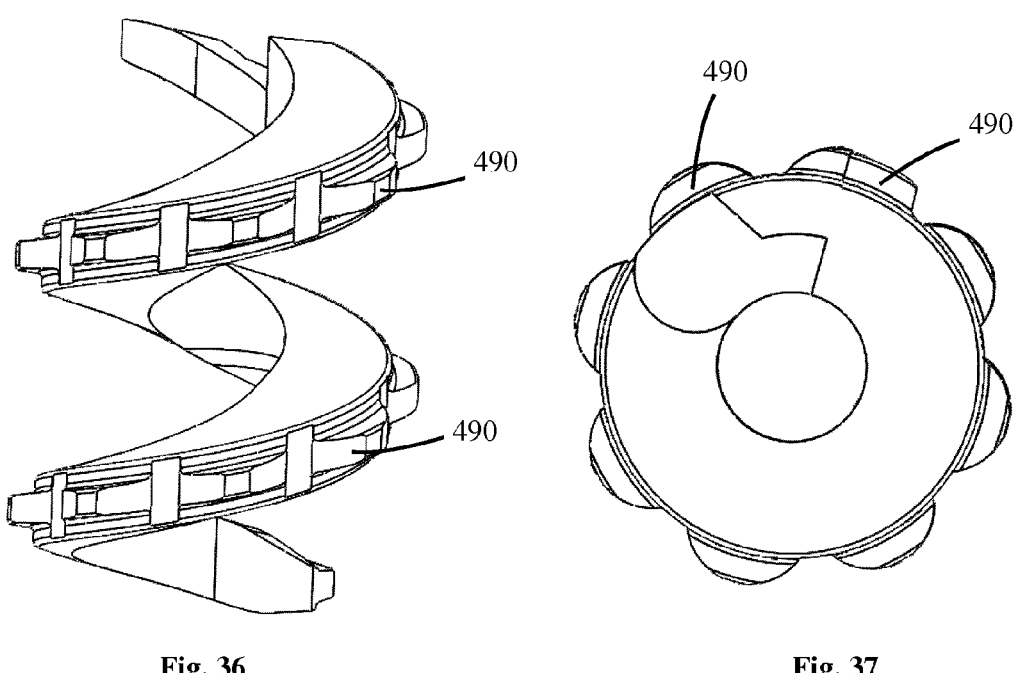
Fig. 36
Fig. 37
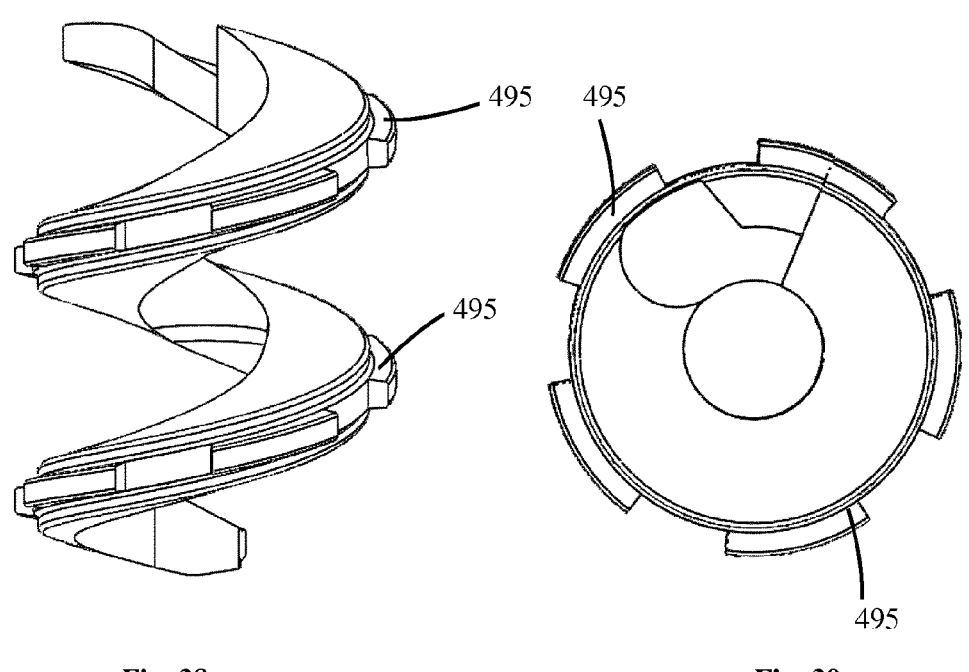
Fig. 38
Fig. 39

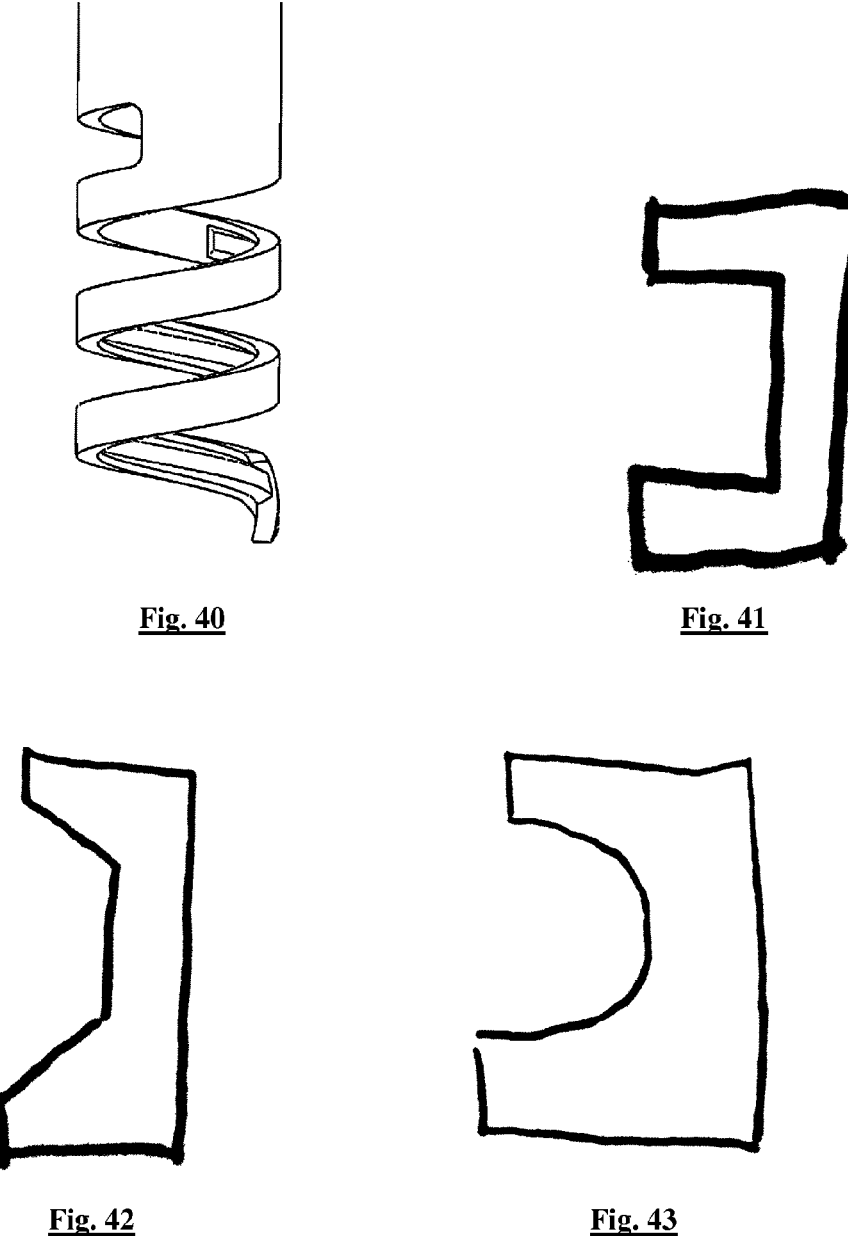
Fig. 40
Fig. 41
Fig. 42
Fig. 43
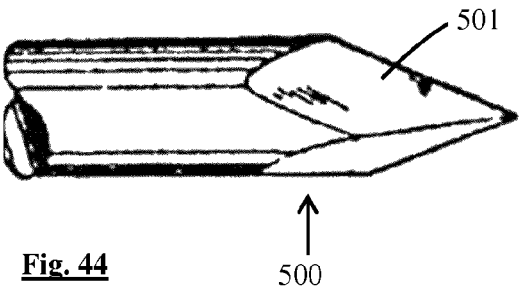
Fig. 44

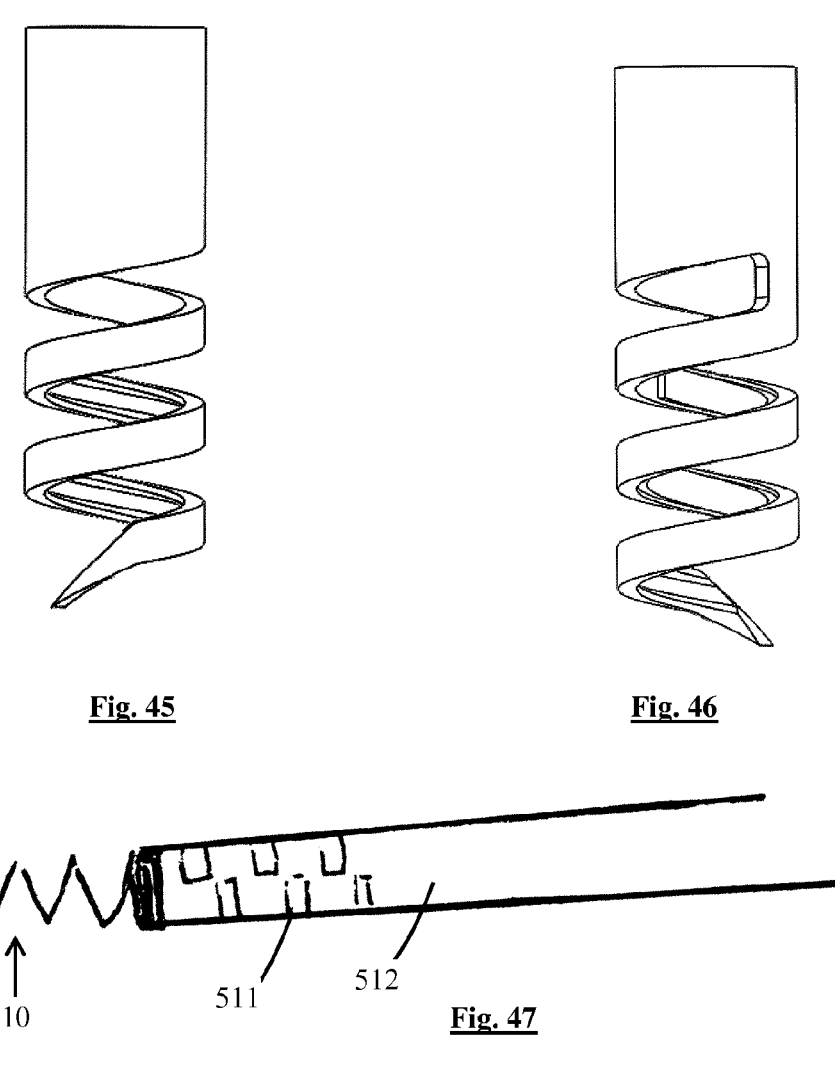
Fig. 45
Fig. 46
Fig. 47
510
511
512
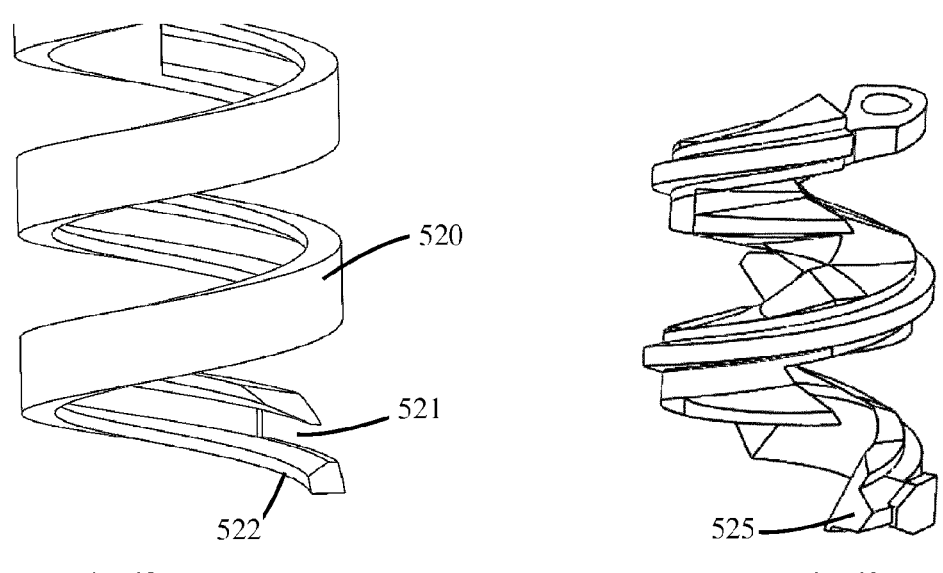
520
521
522
Fig. 48
525
Fig. 49

525

550

550

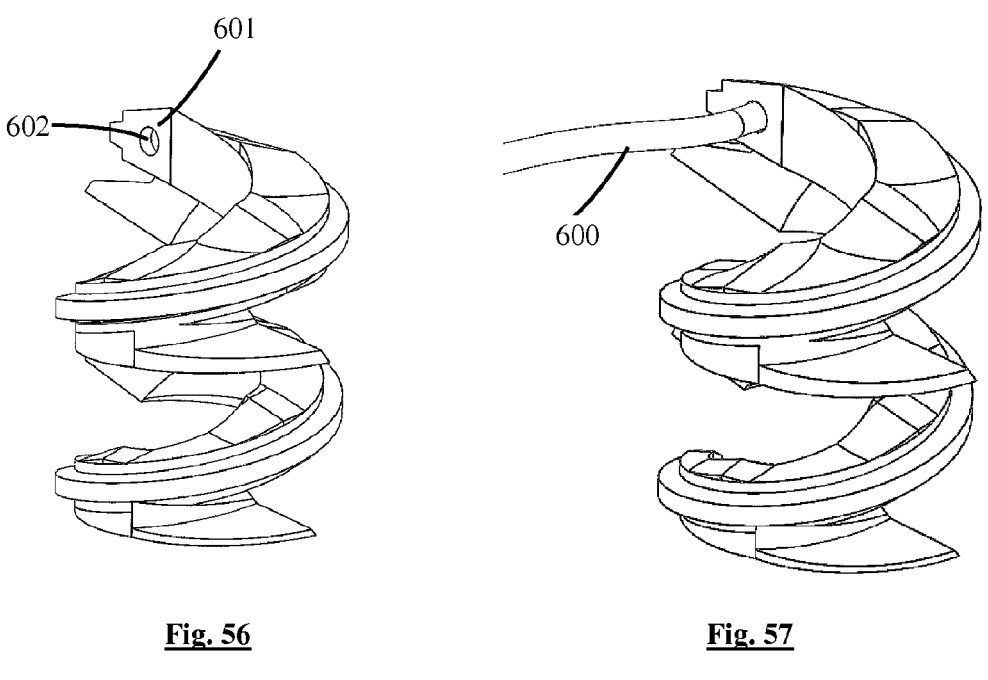
Fig. 56
Fig. 57
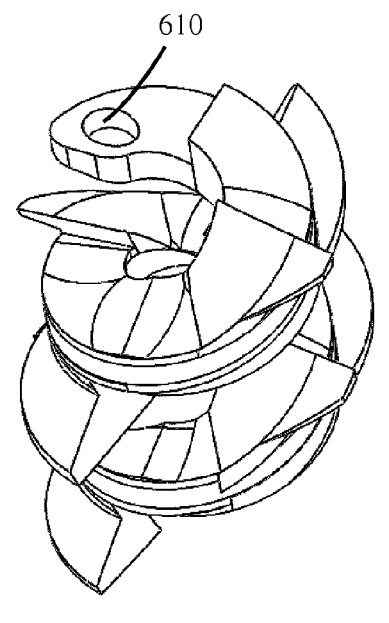
Fig. 58
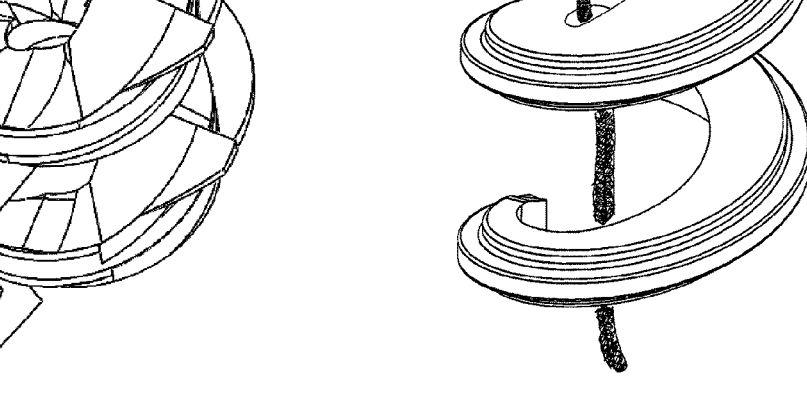
Fig. 59

621   620

622

630

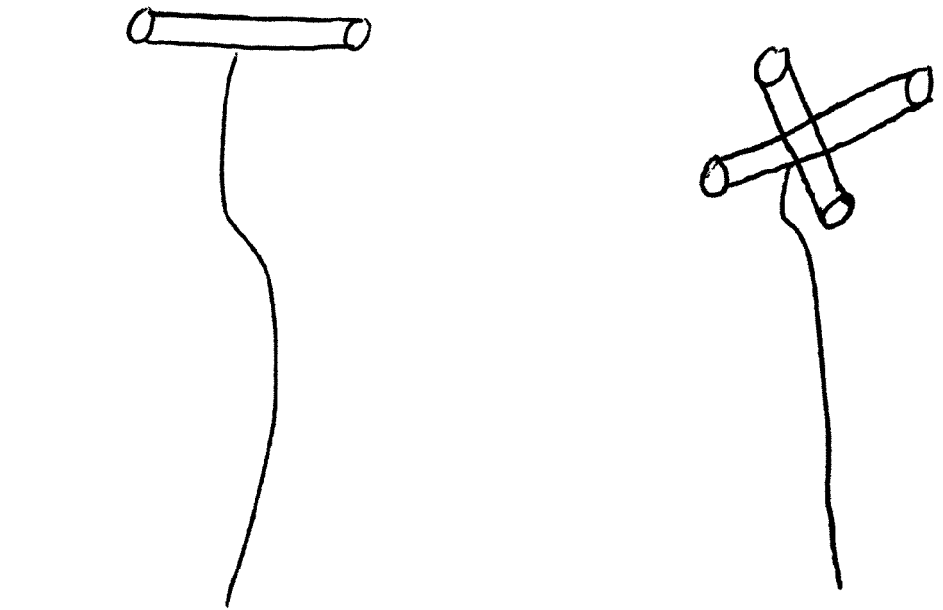
Fig. 62c                                          Fig. 62d
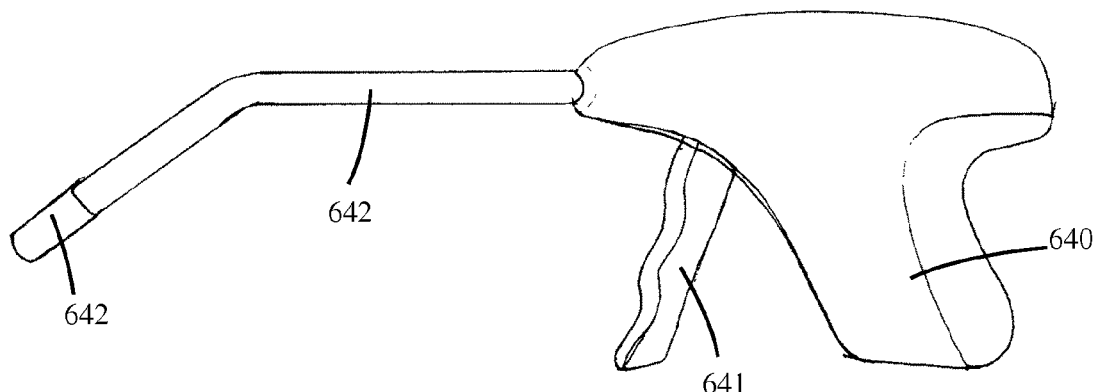
642
642
641
640
Fig. 63
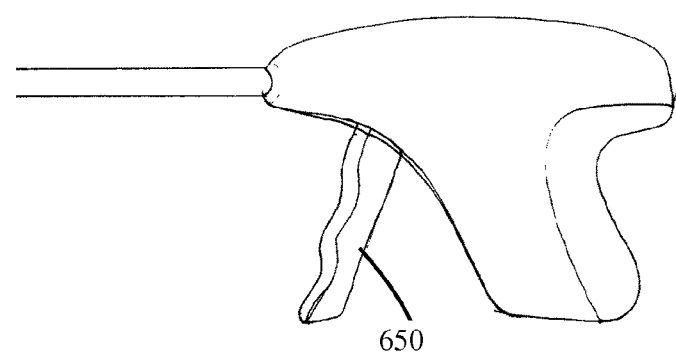
650
Fig. 64

660

180° Rotation

180°

670

815

815

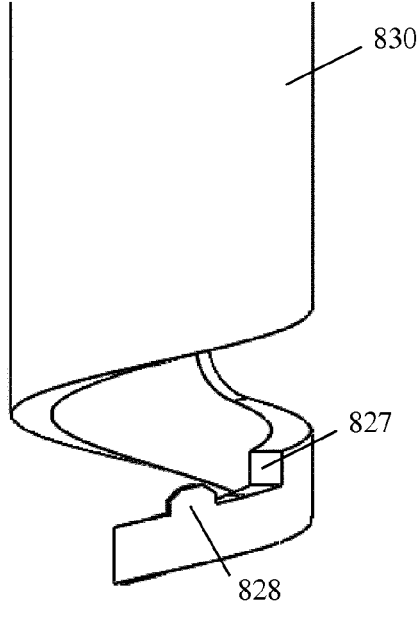
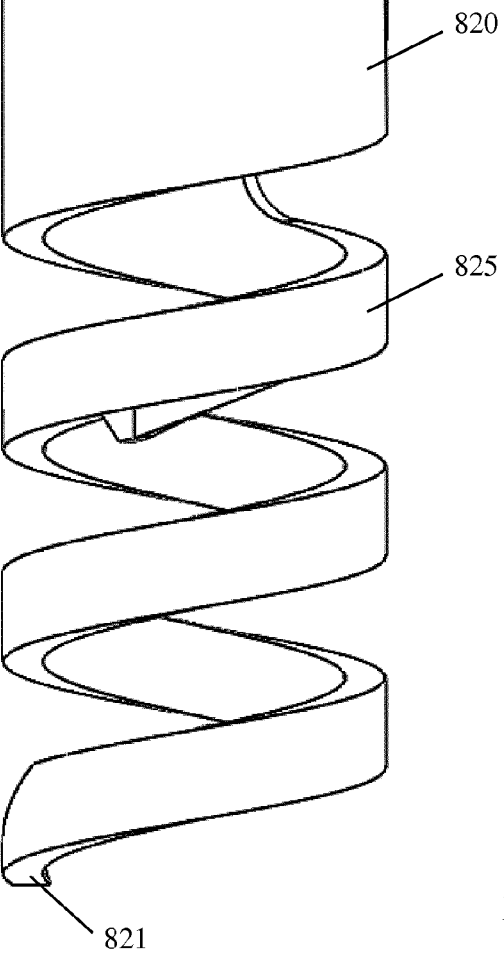
Fig. 91

819

820

820

IMPLANT FOR CLOSING AN OPENING IN TISSUE

CROSS-REFERENCE TO RELATED APPLICATIONS

This is a continuation application under 37 CFR § 1.53(b) of pending U.S. application Ser. No. 16/706,294, filed Dec. 6, 2019, which is a continuation of International Application No. PCT/EP2018/065246, filed on Jun. 8, 2018, which claims the benefit of priority of European Application No. 18170943.7, filed May 4, 2018, European Application No. 17209834.5, filed Dec. 21, 2017, European Application No. 17197528.7, filed Oct. 20, 2017, European Application No. 17195342.5, filed Oct. 6, 2017, and U.S. Provisional Application No. 62/517,553, filed Jun. 9, 2017, all of which are incorporated by reference herein in their entireties.

INTRODUCTION

The invention relates to a device and a system for the treatment of a range of applications including treatment of a sinus or a fistula such as a perianal fistula.

A perianal fistula is an artificial tunnel that, in the majority of cases, develops from an infection that begins within a blocked anal gland. If the infection cannot be cleared from the anal gland an abscess forms and the infection burrows though the sphincteric muscles and exits at the buttocks integument. Patients experience pain associated with the tract and associated abscesses and suffer faecal and blood discharge from the fistula tract. Perianal fistulas may also result from gastro-intestinal diseases such as Crohn's disease, ulcerative colitis, colorectal cancers and their associated treatment and complications due to rectal fissures and trauma.

The global incidence of perianal fistula is 2 per 10,000 population. Over 100,000 fistula procedures are performed between the United States and Western Europe each year. Thirty percent of the procedures performed are reoperations due to treatment failure contributing to a significant preventable cost to the healthcare systems.

Given the inadequate treatment options and poor surgical outcomes there is a defined clinical need for a more effective perianal treatment device.

There is currently no single "gold standard" technique that a surgeon can perform to effectively cure a perianal fistula and not render the patient incontinent. A common fistula treatment is a fistulotomy procedure. A fistulotomy involves the dissection of the sphincteric muscles and the laying open of the fistula tract. Fistulotomies have a relatively high cure rate, however, this procedure results in a high risk of faecal incontinence.

From a patient's point of view, many are happy to assume the risk of incontinence in order to resolve the painful fistula tract. However, this is obviously not an ideal treatment pathway and for many patient population groups the secondary outcome is far from acceptable.

Another commonly used fistula treatment methodology is the use of a seton. Setons are used as a sphincter sparing technique and is simply a suture or vascular strap that is passed through the tract of the fistula and the rectum and tied in a loop. The seton maintains tract patency allowing the infection in the fistula tract to drain, help the tract constrict in length and may cure the tract. If the tract is not cured by the seton the physician can perform a fistulotomy. This approach of trying to preserve the sphincter with setons has been used for over 2500 years and is still the preferred method used by surgeons today.

In an effort to provide a non-destructive perianal fistula treatment various glues and plugs have been developed and introduced to colorectal surgeons in the past 20 years. However, these techniques are not very successful and their use is not widespread. Such glues which are injected into the fistula tract generally become brittle and are not able to occlude the tract for a long enough period to fully heal, faeces re-enter the tract resulting in abscess formation and refistulisation. Physicians often attempt to treat perianal fistulas with glues and plugs even though there may only be a 10 percent chance of effectiveness because it is a sphincter sparing technique and they can always resort to a seton and eventual fistulotomy if all fails.

Attempts have also been made to use plugs to occlude perianal fistula tracts. For example, US2005/004926A describes a plug-like fistula closure device with an attached flexible application string which also serves to evacuate liquids out of a fistula. However, generally the plugs fail because they become extruded from the tract, allowing faeces to enter the tract resulting in reinfection, abscess formation and refistulisation.

There is therefore a need for an improved method and device for the treatment of perianal fistulas.

More generally, there is a need for an improved method and device for treatment of a sinus or a fistula.

STATEMENTS OF INVENTION

According to the invention there is provided an implant for closing an opening in tissue, such as a fistula or a sinus, the implant comprising a coil having an outer diameter that is substantially uniform along the length of the coil and an inner diameter that is tapered between the ends of the coil.

In one embodiment the coil comprises an engagement feature for engagement with a delivery device.

The coil may comprise an outer rail. In some embodiments the rail comprises first and second arms that extend outwardly of the coil, the arms being adapted to receive portion of a driver coil therebetween. The first arm and the second arm may comprise a plurality of spaced-apart segments which are spaced-apart along the implant coil. The segments of the first arm may be offset from the segments of the second arm.

In one embodiment at least some of the rail segments comprise an anti-rewind feature such as a barb.

In some cases the coil comprises a proximal driver end and a distal tissue insertion end and the inner diameter of the coil tapers inwardly from the distal end of the coil.

The implant may taper from an internal diameter of from 1 to 6 mm to an internal diameter of from 0.5 to 2 mm and the pitch of the coil may be from 2 mm to 4 mm.

In one embodiment the implant comprises an interlock feature for releasably interlocking with an interlock feature of a delivery device.

The invention also provides a delivery device for delivery of an implant into tissue, the delivery device comprising a coil having a proximal end and a distal end wherein the coil comprises a distal tip section which is adapted for piercing tissue and/or for compression of tissue.

In one embodiment the coil is a straight helix having a constant pitch. The inner diameter of the driver coil may be from 4 mm to 6 mm, the outer diameter of the driver coil may be from 6 mm to 8 mm, the wall thickness of the driver coil may be from 0.5 mm to 1 mm, and the pitch of the driver coil is from 2 mm to 4 mm.

In some embodiments the driver coil comprises a plurality of coil struts and the height of a strut may be from 0.5 mm to 2 mm, the driver coil may comprise from 2 to 5 turns such as 2.75 turns.

A delivery device as claimed herein, wherein the delivery coil comprises a plurality of turns and wherein the delivery coil comprises at least portion of a turn greater than the number of turns of an implant to be embedded by the delivery device.

In one case the driver coil comprises an engagement feature for engagement with an implant engagement feature.

In one case the driver coil comprises an interlock feature for releasably interlocking with an interlock feature of an implant.

Also provided is a delivery system comprising delivery device of the invention and a driver shaft for the delivery device, the driver shaft and the delivery device may be integral.

In some embodiments, in a first configuration, an engagement feature of the driver coil is engaged with an engagement feature of the implant, and in a second configuration, the engagement feature of the driver coil is disengaged from the engagement feature of the implant, in the first configuration the driver coil may be engaged with an external track of the implant.

In some embodiments, in a first configuration, an interlock feature of the driver coil is engaged with an interlock feature of the implant, and in a released configuration, the interlock feature of the driver coil is disengaged from the interlock feature of the implant, in the first configuration the driver coil may be engaged with an external track of the implant.

In some embodiments, in a delivery configuration, the distal end of the driver coil extends distally beyond the distal end of the implant.

According to the invention there is provided an implant comprising a shaft having a proximal end and a distal end wherein the shaft has a substantially uniform outer diameter and wherein the shaft forms an internal passage having a tapered diameter.

The tapered diameter of the internal passage in one case increases towards a distal end of the shaft.

In one case the internal passage of the shaft is formed by a helical coil.

In some cases a cross section of a distal section of the shaft is tapered towards the distal end of the shaft.

The shaft may comprise an external track for interfacing with a driver. In some cases the track comprises a channel, a rail or a helical track.

In some cases the shaft comprises an external and/or an internal anti-rewind feature. The anti-rewind feature may comprise a barb.

In some cases the shaft comprises an interlock feature for interlocking the implant to a driver.

The invention also provides a delivery device for delivery of an implant into tissue comprising a coil having a proximal end and a distal end wherein the coil comprises a distal tip section which is adapted for piercing tissue and/or for compression of tissue.

In one case the distal tip section is angled towards the distal most tip of the coil.

The distal tip section may extend radially outwardly of the main body of the coil.

In some cases the delivery device comprises a plurality of coil sections. A distal coil section may be tapered. The tapered diameter of the distal coil section may increase towards a distal end of the delivery device.

In some cases the coil sections comprise a distal coil section for receiving an implant and a proximal coil section. The proximal coil section may have at least one dimension which is different than a corresponding dimension of the proximal coil section. An outer diameter of the proximal coil section may be less than an outer diameter of the distal coil section.

In some cases delivery device comprises two elements which are independently movable relative to each other. In one case the elements are independently rotatable relative to each other.

The delivery device elements may comprise a first element having an implant housing region and a second element for engaging a proximal end of an implant, the first element being movable proximally relative to the second element.

In one embodiment the delivery device coil is a straight helix of constant pitch.

The first element may be a straight helix of constant pitch.

In some cases the delivery device comprises an overtube for the coil.

The overtube may comprise a distal end with formations which are configured for engagement with tissue. Needles may extend or are extendable distally from the distal end of the overtube. In some cases the needles are movable relative to the overtube from an extended configuration in which the needles extend distally of the distal end of the overtube to a retracted configuration.

The invention also provides a system comprising an implant of the invention and a delivery device of the invention.

In a first configuration, a portion of the driver coil may be engaged with a portion of the implant, and in a second configuration, the portion of the drive coil is disengaged from the portion of the implant. In one case in the first configuration, the driver coil is engaged with the external track of the implant.

There may be a releasable interlock between the driver coil and the implant.

In some cases in a delivery configuration, the distal end of the driver coil extends distally beyond the distal end of the implant.

In one case the driver coil and an external track of the implant have differing geometrics.

The pitch of the driver coil may be different than the pitch of the implant track.

In one case the pitch of the driver coil is offset from the pitch of the implant track.

In some cases the devices and methods of the invention may be used to treat a perianal fistula.

However, the devices and methods may be used in a range of applications including treatment of a sinus or a fistula more generally. Examples include treatment of the following:

Rectovaginal fistulas

Entrocutaneous fistulas

Enteroenteral fistula

Gastric fistula

Muscle, integument, fascia or other tissue defects

Pilonidal or other sinus

Bodily vessel

Fluid lumen

Repair of anatomical defects or damage

The invention also provides a method for treating a fistula comprising the steps of:— providing an implant;

inserting the implant into the bulk tissue of the sphincteric muscle complex adjacent to the fistula; and using the implant to draw tissue surrounding the fistula inwardly.

The method may further comprise:— activating the implant to draw tissue surrounding the tract inwardly.

The method may comprise anchoring the implant in the tissue.

In some cases the implant is anchored prior to activation of the implant.

The implant may comprise an anti-rewind feature that may be selected from one or more of:

a positive feature such as a barb, arrowhead or fishhook-like feature;

a negative feature such as a trough, a slot or a groove, and a surface feature such as surface roughening.

In one embodiment the device comprises a tapered portion which is configured for insertion into bulk tissue surrounding a fistula and a driver interface portion which is configured for engagement with a driver for rotation of the coil to draw tissue surrounding a fistula inwardly.

The invention also provides a drainage seton having an anchoring feature for anchoring the seton in situ. In some cases the anchoring feature is provided at a compression zone or region of the seton.

In some embodiments the anchoring feature comprises a step or projection on the seton, such as one or more of a knot, a barb or a quill.

In some cases at least a portion of the outer surface of the driver coil is lubricious.

There may be engagement features on the driver coil and/or the implant coil for temporarily locking the driver coil to the implant coil for delivery of the implant coil.

The invention also provides a fistula treatment system comprising a fistula treatment device of the invention and a tissue stabilising device for stabilising the mucosal tissue for delivery of the implant.

In some embodiments the stabilising device comprises a hollow element attached to the delivery mechanism and surrounding the implant prior to delivery. The hollow element may be biased by spring loading or otherwise to apply pressure to the mucosal surface.

In one embodiment a leading surface of the hollow element that interfaces to the mucosal surface interacts with the mucosal surface to prevent rotation and/or twisting of the mucosal lining.

The hollow element may comprise features such as needles for penetration into the mucosal surface.

The invention also provides a method for treating a fistula comprising the steps of:—providing an implant of the invention;

inserting the implant into the bulk tissue of the sphincteric muscle complex adjacent to the fistula; and rotating the implant to draw tissue surrounding the fistula inwardly.

In some embodiments the method comprises:— providing a drainage seton;

embedding the seton in the sphincter muscle complex; and leading the seton so that the distal end of the seton protrudes through the external opening of a fistula tract.

In some cases, after insertion of the implant coil, the delivery device is released from the coil.

The method may further comprise:— providing a drainage seton;

attaching the seton to the coil; and leading the seton externally of the fistula.

The method may comprise:— providing a drainage seton;

embedding the seton in the sphincter muscle complex; and leading the seton so that the distal end of the seton protrudes through the external opening of a fistula tract.

In some cases the shape of the coil in cross section is selected from one or more of round, oval, triangular, multifaced and ribbon.

In one embodiment at least a portion of the coil is bioabsorbable.

In one case the fistula treatment device further comprises a drainage seton.

The seton may extend from the coil.

In one case the seton is hollow.

In one case the seton is solid.

In one embodiment the seton has a plurality of peripheral holes.

The shape of seton in cross section in some cases is selected from one or more of round, oval, star and cross.

In one embodiment the seton comprises multiple elements. The elements of the seton may be braided.

In one case at least a portion of the seton is bioabsorbable.

In one case the seton is of differential bioabsorption. In one embodiment a proximal portion of the seton is bioabsorbable, for example, to facilitate removal of a remainder of the seton. In another embodiment a distal portion of the seton is bioabsorbable to facilitate closure of the eternal opening of the fistula prior to full absorption of the seton.

In one embodiment at least a portion of the coil is bioabsorbable and at least a portion of the seton is configured to bioabsorb in advance of bioabsorption of the coil.

The invention also provides a fistula treatment system comprising a fistula treatment device and a driver implement for rotation of the coil to draw tissue surrounding a fistula inwardly.

In one case the driver implement comprises a driver coil which is configured for engagement with the driver interface of the implant coil.

In one case the driver coil is hollow and the corresponding driver interface portion of the implant coil is solid.

In another case the driver coil is solid and the corresponding driver interface portion of the implant coil is hollow.

The invention also provides a fistula treatment device comprising an implant as defined which is configured for insertion into bulk tissue surrounding a fistula and being rotatable to draw tissue surrounding the fistula inwardly and a drainage seton extending from the implant.

In one embodiment the seton is of differential bioabsorption.

In one case a proximal portion of the seton is bioabsorbable to facilitate removal of a remainder of the seton.

The tapered coil is preferably configured for insertion at the site of the internal opening of a fistula and being rotatable to draw bulk tissue, including sphincteric muscle, surrounding the fistula inwardly.

In one case the coil has a leading end and a trailing end, the coil decreasing in lateral extent between the leading and trailing ends. The leading end may include a pointed tissue insertion tip.

In one embodiment the device comprises a seton attachment feature.

The attachment feature may be selected from one or more of:—
  a protrusion such as a ball-shape;
  a hook;
  a cleat;
  a butt joint; or
  a bond such as a thermal and/or adhesive bond.

In one embodiment the implant has a recess or hole for reception of a seton. The seton may be bonded or fixed to the recess or hole, for example by adhesive and/or thermal bonding, and/or crimping.

In another embodiment the device comprises a delivery mechanism attachment feature.

The method may comprise:—
  providing a drainage seton;
  attaching the seton to the coil; and
  leading the seton externally of the fistula.

The method may comprise:—
  providing a drainage seton;
  embedding the seton in the sphincter muscle complex; and
  leading the seton so that the distal end of the seton protrudes through the external opening of a fistula tract.

The perianal fistula treatment device has the advantages of:
  effective healing of the fistula tract;
  preservation of continence; and
  improved healing time.

The device preserves the patient's continence by protecting the sphincteric muscles from division. The device is securely anchored into the fistula tract, effectively sealing the tract and preventing faecal matter from entering the internal opening during the healing process.

The device allows any remaining abscess materials to drain from the tract during the healing process. The device may be integrated into the tissue over the healing process, and may be ultimately absorbed as the tract is healed.

The invention removes variability due to surgeon skill by providing a standardised technique for treating perianal fistulas.

The method for treating a fistula may include any or all of the following steps:
  using seton for location/tension/mucosal wall apposition prior to delivering;
  using a delivery mechanism to deliver a closure device to repair a defect in the bulk tissue of the sphincteric muscle complex;
  delivering a closure device below the surface of the mucosal lining of the rectum at the dentate line into bulk tissue to allow remodelling of the mucosal lining over the site of delivery; and
  embedding a seton in the sphincter muscle complex with the distal end protruding through the external opening of a fistula tract in order to allow drainage and healing of a fistula tract.

The method may include compressing fistula tissue via the implant, the compressing may include progressively compressing fistula tissue such that a compression force imparted to fistula tissue via the distal end of the implant may be less than a compression force imparted to fistula tissue via the proximal end of the implant.

The method may further include compressing fistula tissue so as to close the internal opening while maintaining the external opening open.

Facilitating drainage through the external opening may include positioning a drainage member in the fistula tract. At least a portion of the drainage member may extend from a location within the fistula tract and through the external opening.

A seton is used as a drainage mechanism to palliatively treat a perianal fistula. A drainage member or drain may be regarded as a single ended seton. The terms seton, drain, or drainage member are use interchangeably.

At least one of the implant or the drainage member may be bioabsorbable.

Both of the implant and the drainage member may be bioabsorbable, and a rate of absorption of the implant may be faster than a rate of absorption of the drainage member.

Both of the implant and the drainage member may be bioabsorbable, and a rate of absorption of the drainage member may be faster than a rate of absorption of the implant.

A method of closing an opening in tissue may include:
  delivering an implant of the invention into tissue such that
    a plurality of helical loops of the implant may pass through tissue surrounding the opening and may compress the tissue radially inwardly; and
  fixing a drain element relative to the implant such that after the implant is delivered the drain element may extend from within the opening to a location outside of the opening, the drain element may be configured to facilitate fluid drainage from the opening along the drain element.

The method may further include drawing tissue around the opening radially inwardly toward a center of the implant, a first region of tissue may be drawn radially inwardly to a greater extent than at least a second region of tissue.

The method may further include sealing closed only one end of the opening.

The invention also provides a kit for closure of an opening in human tissue may comprise:
  an implant of the invention; and
  a longitudinally extending drain member.

At least one of the implant or the drain member may be bioabsorbable.

Both of the implant and the drain member may be bioabsorbable, and a rate of absorption of the implant may be faster than a rate of absorption of the drain member.

Both of the implant and the drain member may be bioabsorbable, and a rate of absorption of the drain member may be faster than a rate of absorption of the implant.

The invention also provides a delivery device for delivery of an implant into tissue, the delivery device comprising a coil having a proximal end and a distal end wherein the coil comprises a distal tip section which is adapted for piercing tissue and/or for compression of tissue.

In one case the coil is a straight helix having a constant pitch.

The inner diameter of the driver coil is from 4 mm to 6 mm, the outer diameter of the driver coil is from 6 mm to 8 mm, the wall thickness of the driver coil is from 0.5 mm to 1 mm, and the pitch of the driver coil is from 2 mm to 4 mm.

The driver coil may comprise a plurality of coil struts and the height of a strut is from 0.5 mm to 2 mm.

In one case the driver coil comprises from 2 to 5 turns such as 2.75 turns.

In some cases the delivery device comprises an engagement feature for engagement with an implant engagement feature.

The delivery device may comprise an interlock feature for releasably interlocking with an interlock feature of an implant.

The delivery coil may comprise a plurality of turns and wherein the delivery coil comprises at least portion of a turn greater than the number of turns of an implant to be embedded by the delivery device.

The invention also provides an implant delivery device comprising an implant delivery coil and a drive shaft for the delivery coil, the drive shaft being movable form a retracted implant loaded configuration to an extended implant delivery configuration wherein the shaft is rotatable in a delivery direction for movement between the loaded and delivery configurations. In one case the shaft is prevented from rotation in an opposite direction to the delivery direction between the loaded and delivery configurations.

The shaft may be movable from a delivery configuration to a disengaged retracted configuration. The shaft may be rotatable in a direction opposite to the delivery direction for movement from the delivery configuration to the disengaged retracted configuration. The delivery direction may be a clockwise direction and the disengaged direction is a counter clockwise direction.

In one case on movement between the delivery configuration to the disengaged retracted configuration the shaft is free to rotate in a counter-clockwise direction.

The may comprise a housing for the delivery device and the driver shaft. The housing may comprise a grip portion and a tube extending from a distal end of the grip portion. The tube or a section thereof may be malleable or flexible. The tube may comprise a distal bend. In some cases the bend extends at an angle of from 30 to 60 (such as 45) degrees with respect to a longitudinal axis of the tube.

In some cases the system further comprises a rotary handle for rotating the shaft.

In one case the system further comprises a releasable lock to prevent rotation of the shaft.

In some cases the system comprises a mounting element for mounting a drain to the driver shaft.

The mounting element may be movable with the shaft. The mounting element may be movable from a loading configuration for mounting a drain to the mounting element to a retracted configuration.

In some cases at least a portion of the drive shaft is flexible.

BRIEF DESCRIPTION OF THE DRAWINGS

The invention will be more clearly understood from the following description of some embodiments thereof, given by way of example only, with reference to the accompanying drawings, in which:

FIGS. 11 and 12 are perspective views of a tissue stabilisation device of the invention;

FIGS. 13 and 14 are isometric views of an implant driver coil according to the invention;

FIGS. 15 and 16 are isometric views of an implant according to the invention;

FIGS. 17 to 23 illustrate the engagement of the implant with the drive coil;

FIG. 24 is an isometric view of another implant and FIG. 25 is an isometric view of another driver coil according to the invention;

FIGS. 26 and 27 illustrate an implant with a tapered rail and the corresponding driver coil;

FIGS. 28 and 29 illustrate an implant with an I-section rail and the corresponding driver coil;

FIGS. 30 to 33 are a series of images that illustrate the engagement of another implant and driver coil;

FIGS. 36 and 37 are isometric and plan views of another implant with a segmented rail;

FIGS. 38 and 39 are isometric and plan views of another implant with a segmented rail;

FIGS. 40 to 43 illustrate implant coils with troughs of different shapes;

FIG. 44 is an enlarged view of a distal tip of driver coil;

FIGS. 45 and 46 are views of a driver coil with a "concord" shaped distal tip;

FIG. 47 is an image of another driver coil and integral drive shaft;

FIGS. 48 to 50 are images of another implant and associated driver coil;

FIG. 56 is a perspective view of another implant with a mounting feature for reviewing a drain or seton;

FIG. 57 is a view of the implant of FIG. 56 with the drain attached;

FIGS. 58 and 59 are views of another implant and a drain;

FIG. 62c is a view of another attachment feature and a drain;

FIG. 62d is a view of a further attachment feature and a drain;

FIGS. 63 to 68 are views of various delivery devices;

FIG. 91 is an exploded view of the driver coil;

DETAILED DESCRIPTION

Figure 1:
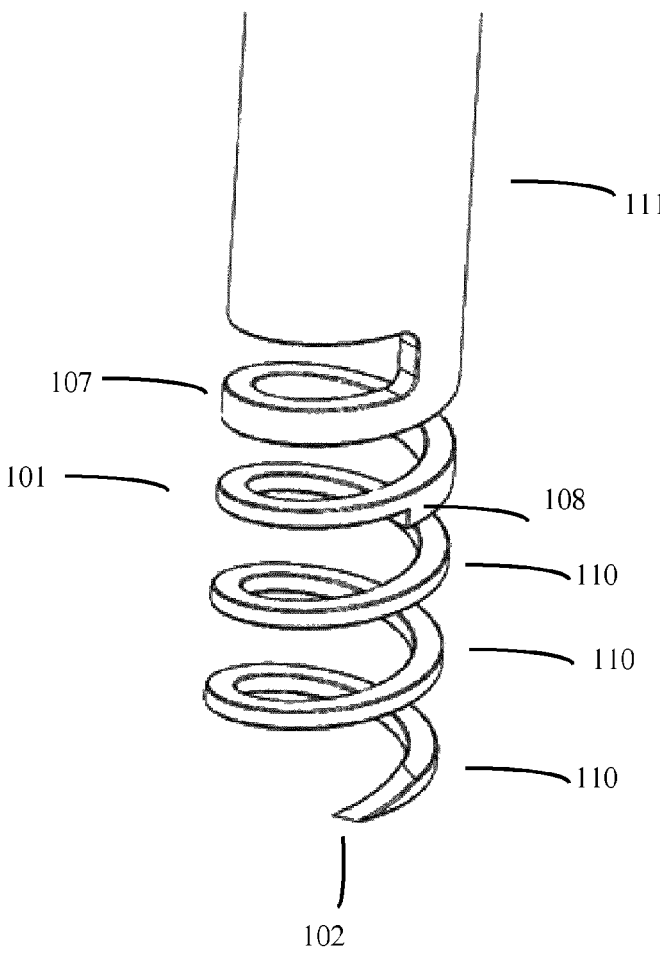
FIG. 1 is a perspective view of a delivery device according to the invention.

The following aspects are described in detail with reference to some of the drawings:

1. Straight sided delivery mechanism and variations
2. Corresponding implant geometry and features
3. Interlocking feature
4. Driver mechanism variation
5. Belt loop embodiment
6. Tissue stabilisation.

In the invention the delivery mechanism affects the initial gathering and compression of tissue.

1. Straight Sided Delivery Mechanism

A coiled delivery mechanism is used for delivering an implant into tissue. In one case, illustrated in FIG. 1, the delivery coil 101 is a straight helix of constant pitch. The delivery mechanism fully supports the full length of the implant 105 (i.e. the implant is housed within the delivery coil). The delivery coil forms a piercing sharp tip 102 at its distal end.

Figure 2:
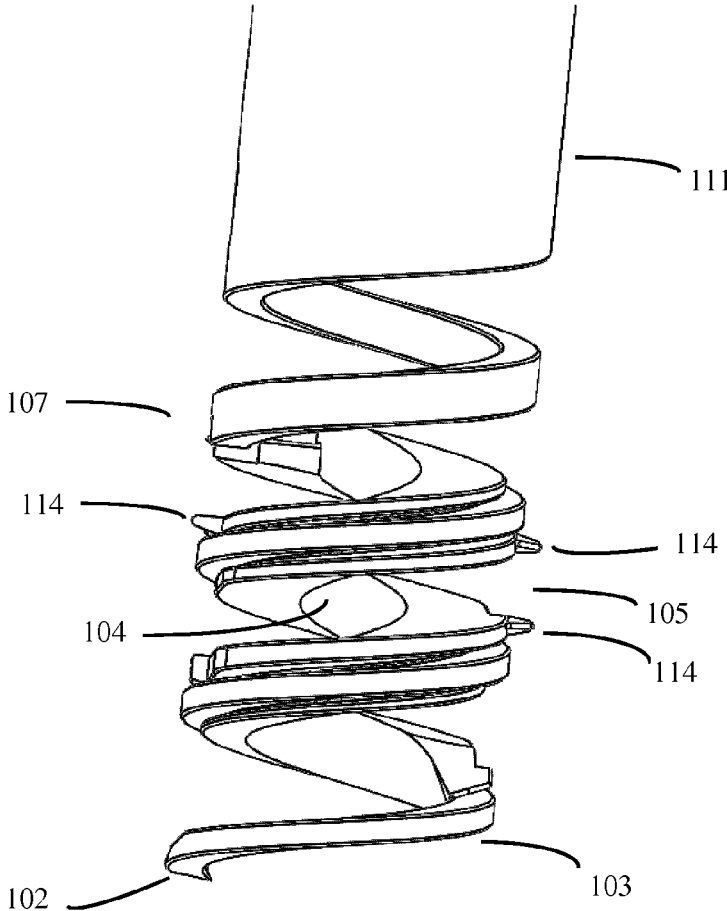
FIG. 2 is a perspective view of the delivery device with an implant of the invention.
Figure 3:
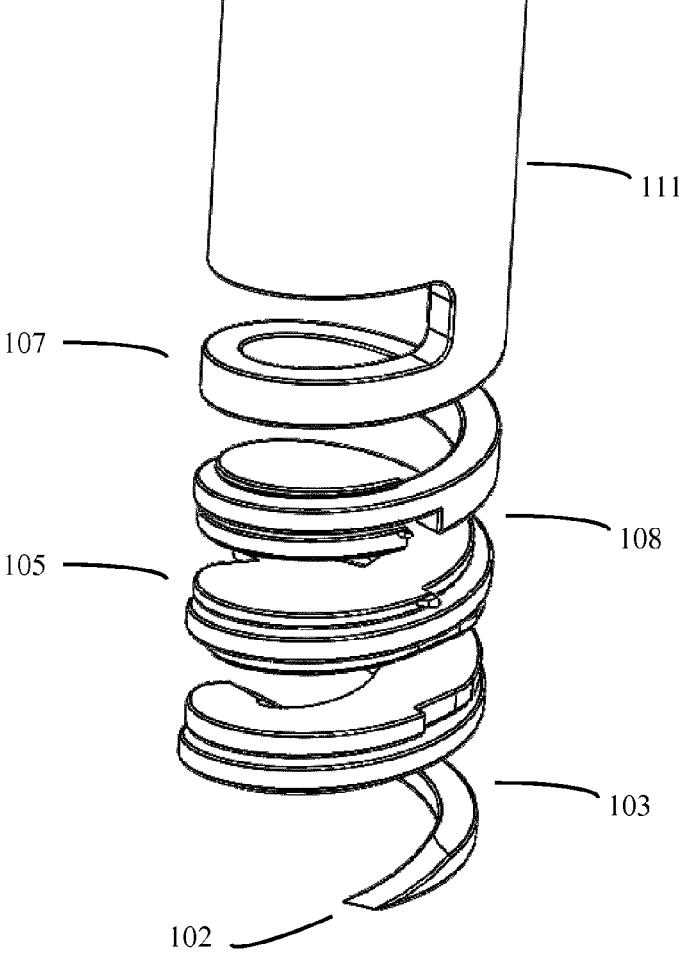
FIG. 3 is another view of an implant and a delivery device.

The delivery coil 101 acts to gather the first (largest/distal) loop of tissue 103 as illustrated in FIG. 2 and leads this tissue into a compression zone 104 of the implant.

Figures 9A, 9B, 9C, 10:
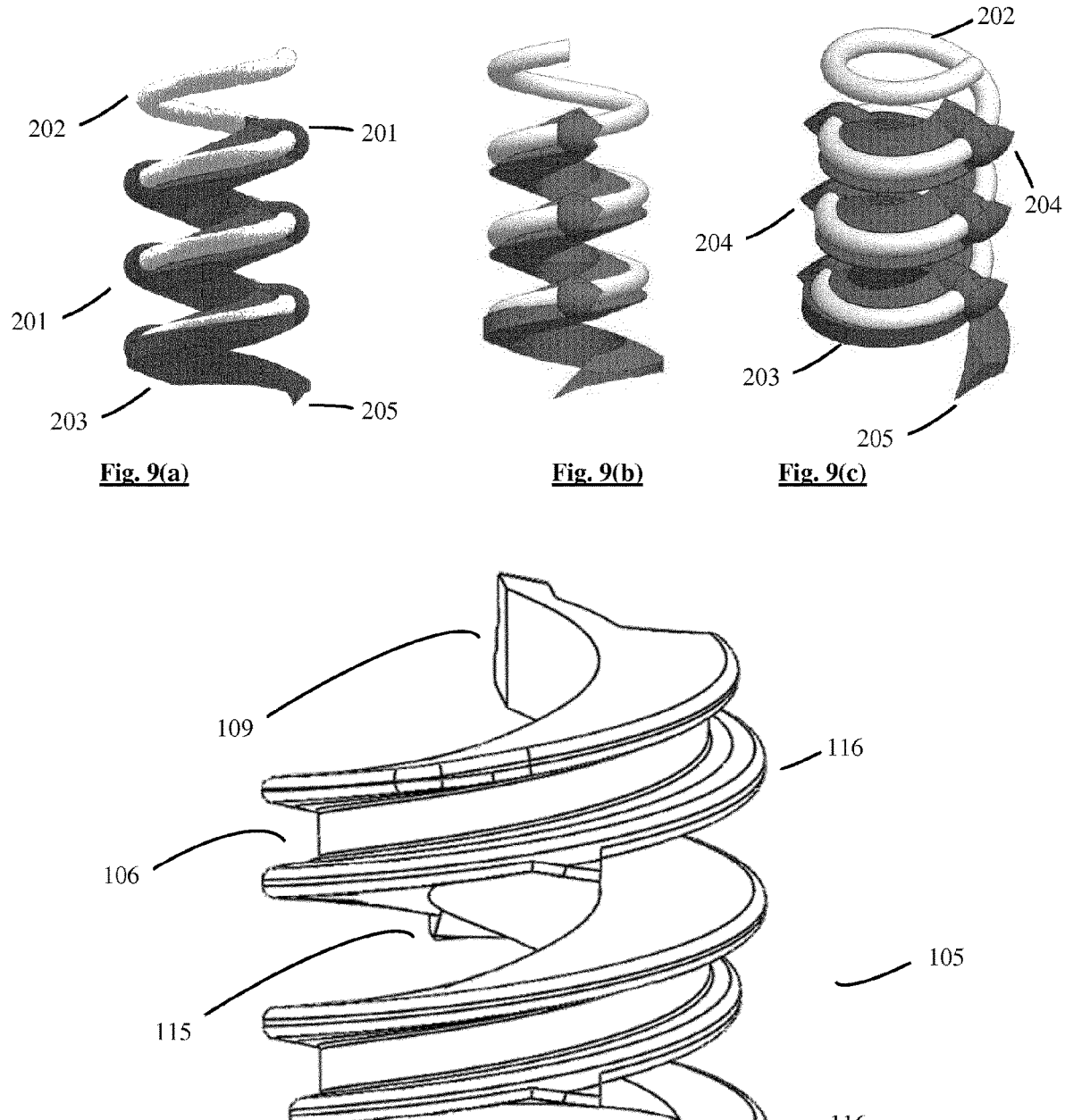
FIGS. 9(a) to (c) are a series of images showing a guide in the form of loops though which a driver coil extends.
FIG. 10 is a perspective view of an implant according to the invention.

The delivery coil may consist of a number of distal coil loops 110 (FIG. 1) which are of appropriate dimensions to interface to an implant track 106 (FIG. 10). An engagement surface 108 (FIG. 1) may be provided to interface to the implant proximal surface 109 (FIG. 10). A further coil 107 (FIG. 1), or plurality of coils, may be provided proximal to the implant to allow for controlled depth of delivery of the implant into tissue. This coil may be of differing cross sectional area, or shape, to the implant engagement coils 110.

The delivery coil may be attached to a delivery tube 111. The delivery coil may also formed by a cut (e.g. laser cut) in this delivery tube 111. The delivery tube 111 is preferentially a hollow tube. It may also be formed form a solid rod in alternative embodiments.

The driver coil tip 102 may be so shaped as to advantageously penetrate the tissue during delivery. The tip 102 may be angled down towards the tissue surface to facilitate piercing, radially outwards to facilitate gathering of tissue for compression and/or to accommodate larger tissue openings, or a combination of both.

The driver coil may have a larger distal diameter than subsequent (more proximal) coils (i.e. tapered coil with larger distal end). A larger diameter allows for gathering of greater bulk of tissue for compression. The larger diameter can also disengage from the implant track due to the straight nature of the outside diameter of the implant.

2. Corresponding Implant Geometry and Features

The following implant features are unique to the straight sided delivery mechanism.

The implant 105 is comprised of an internal tapered aspect 104 with an external straight (non-tapered) outside diameter which contains a track 106 that interfaces with the driver coil 101.

Figures 4A, 4B, 4C:
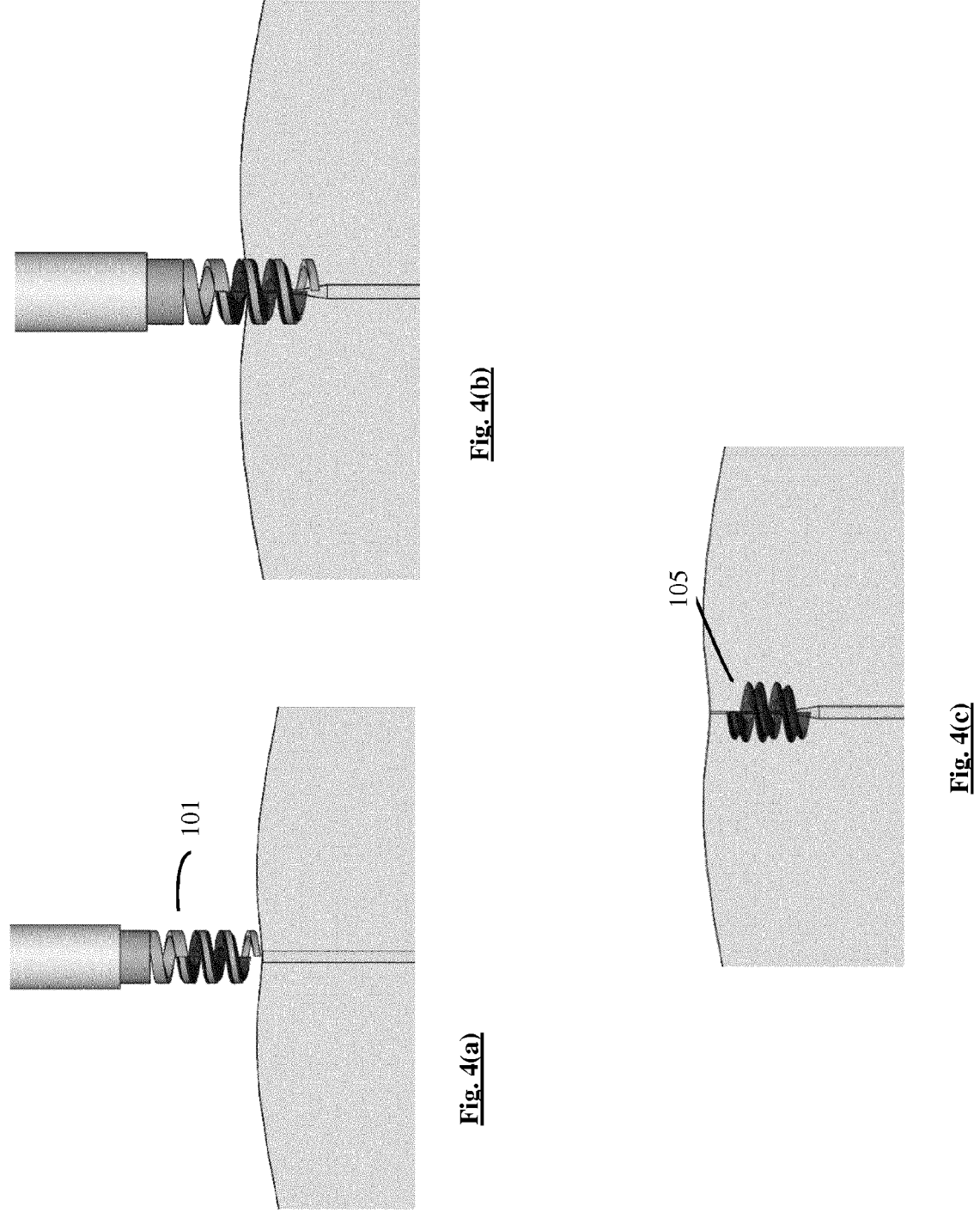
FIGS. 4(a) to (c) are a series of images of the delivery device and implant, in use.

The internal tapered section 104 allows for tissue compression and retention of compression post removal of the driver coil as illustrated in FIG. 4.

The track 106 on the external diameter of the implant 105 facilitates an interface to the driver coil 101. The depth of this track may be undersized to allow for a friction interface keeping the implant in place until delivery.

As illustrated for example in FIG. 10, the cross-section of the distal end of the implant 113 is 'feathered' or sloped to interface to the driver coil allowing a seamless transition from the driver coil to the implant internal taper during delivery. This geometry reduces the torque required for delivery and prevents tissue fouling on the implant distal edge during delivery.

Anti-rewind features, or barbs, may be positioned on the implant externally 114 or internally 115. These features may be beneficial in the disengagement of the driver coil during delivery of the implant into tissue. They also serve to prevent migration of the implant post implantation.

The driver coil 101 and implant engagement track 106 may have differing pitch to create a varying 'shelf' feature 116 along the length of the implant. This varying geometry may be beneficial for stabilising (locking) the implant within the driver coil. Additional this varying feature may be beneficial in providing a stronger surface for the implant/driver coil interaction during dynamic delivery or disengagement and retraction.

In a similar manner the driver coil pitch and implant track pitch may be offset either proximally or distally to allow for a corresponding thicker 'shelf' surface.

There may be anti-rewind features such as barbs on the inner surface of the implant.

3. Interlocking Feature

Figure 8:
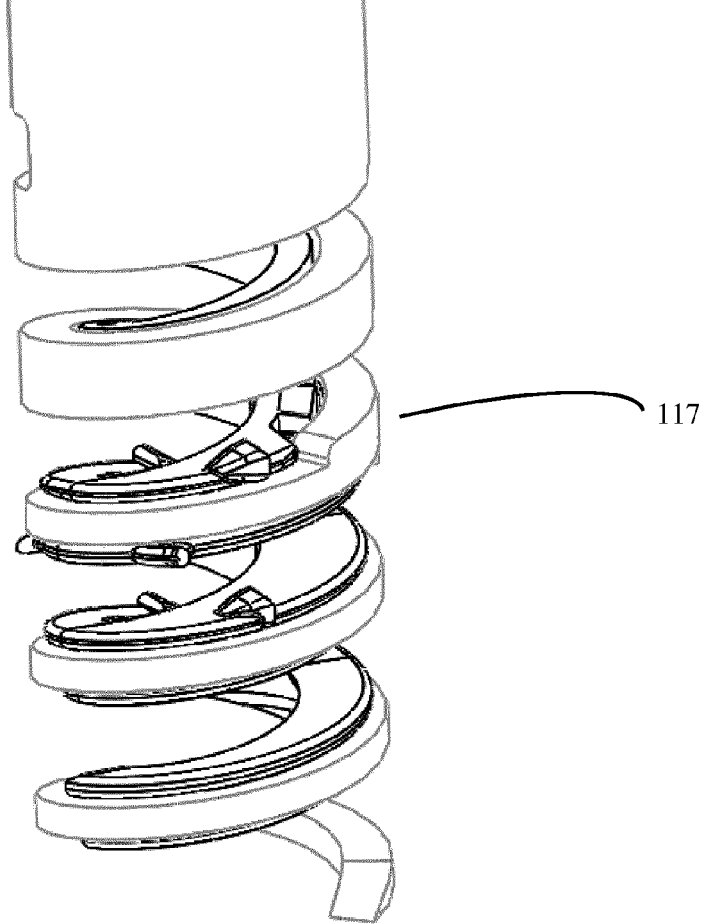

An interlocking feature such as feature 117, illustrated in FIG. 8, may be provided to secure the implant to the driver mechanism until delivery at the appropriate location.

Figure 5:
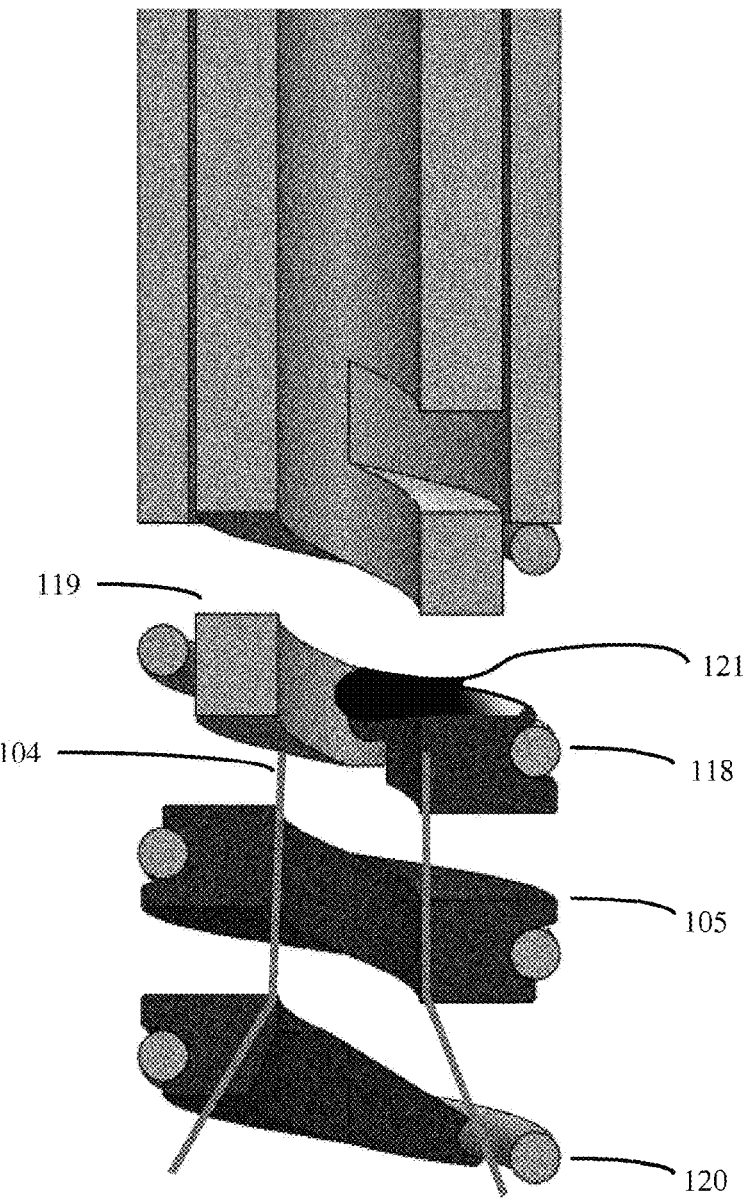
FIG. 5 is a perspective, partially cut-away view of the delivery device and implant.
Figure 6:
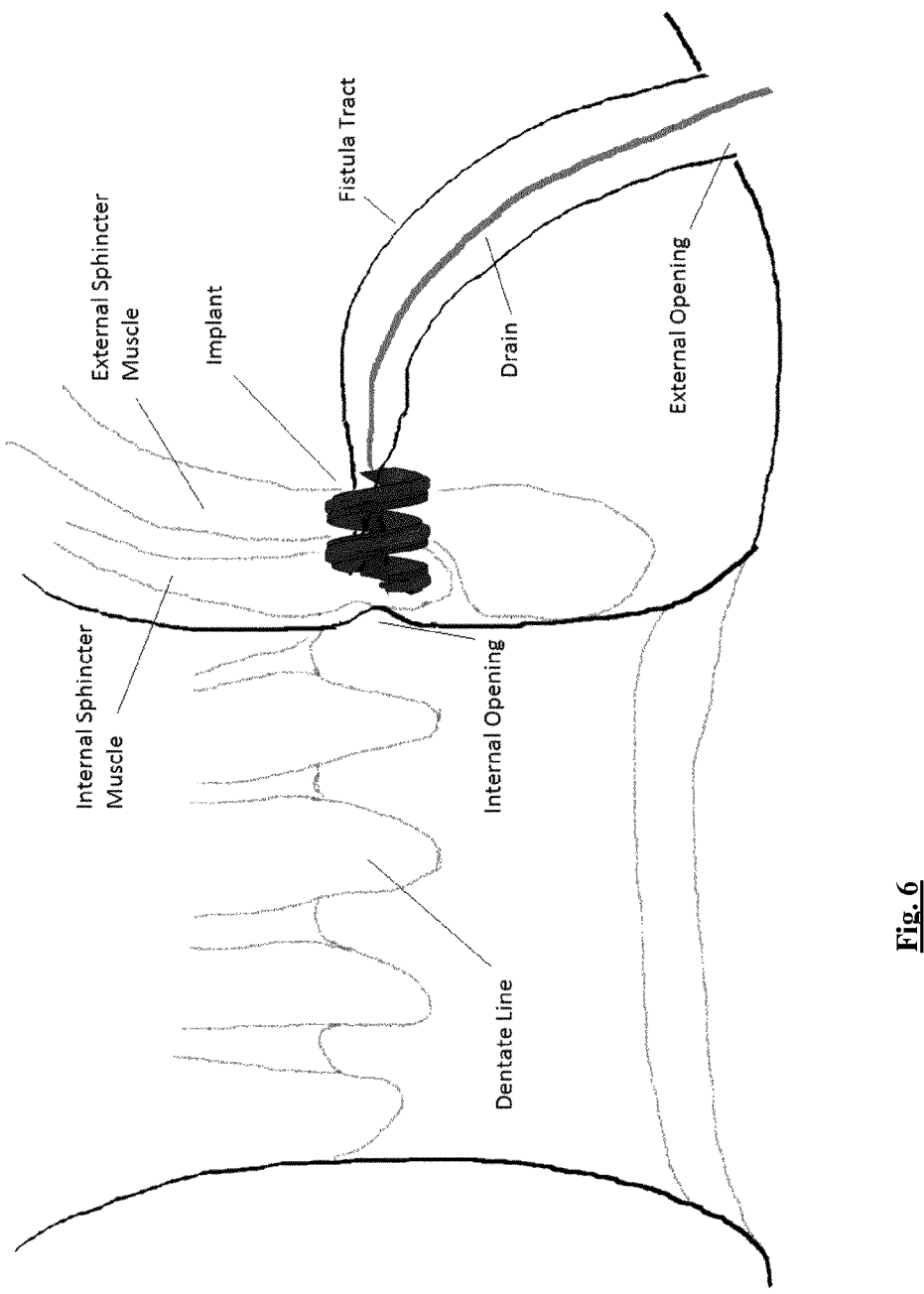
FIG. 6 is a view of a fistula with the implant of the invention, in situ.
Figure 7:
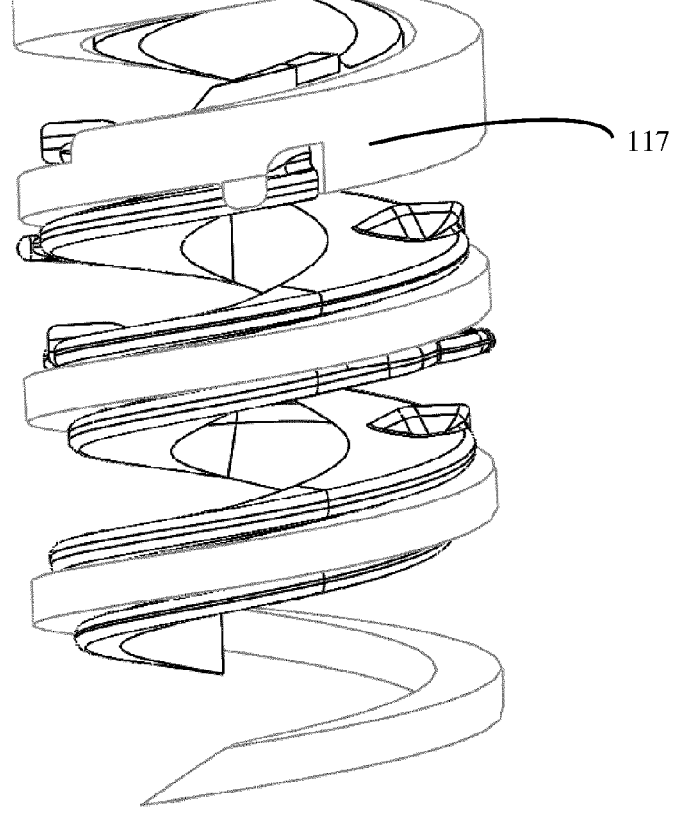
FIGS. 7 and 8 are perspective views of another implant and delivery device with an interlock feature between the implant and the delivery device.

The lock feature may consist of any of the following:

Negative feature on implant surface and corresponding mating positive feature on driver coil Negative feature on driver coil and corresponding mating positive feature on implant surface Alternative embodiments that allow frictional disengagement of the driver coil and the implant after delivery to the appropriate location in tissue Alternative embodiments that allow active disengagement of the driver coil and the implant after delivery to the appropriate location in tissue 4. Driver Mechanism Variation The implant driver may be constructed of two independent rotatable tubes made into coils. Referring to FIG. 5, an outer most driver coil 118 may be configured in a way that it constrains the implant along the outside surface of the implant. The distal most portion of the outer driver coil 120 extends beyond the implant to act as the leading edge to facilitate the puncture of tissue and gathering of tissue to be lead into the compression zone of the implant 104.

An inner tube coil 119 may be used to maintain the implant's initial position acting as a backstop preventing the implant from moving proximally. This inner coil may have a locking mechanism to maintain the retention of the implant on the driver mechanism 121 until the desired time of release.

During delivery, the implant 105 is constrained by the two driver elements until the delivery to the appropriate location is complete. The outer driver coil 118 is then retracted by reversal (preferentially in an anti-clockwise manner). After the outer coil is free from the implant the inner driver coil 119 is retracted by reversal (preferentially in an anti-clockwise manner.

In an alternative embodiment a driver coil may act as a guide that is first delivered into tissue and acts as a guide for an implant that may be subsequently advanced over it. In this embodiment, a straight coiled driver element with a sharp tip is driven into the target tissue.

Once the driver coil resides at the specified depth a rigid (or semi rigid) implant may be advanced over the driver coil. The implant is advanced by a proximal "pusher" element which may be located internally to the driver coil. Upon driver retraction the implant is held in place by a proximal pusher element. The pusher element may be coiled in shape. The pusher element is retracted subsequent to the retraction of the driver coil.

5. Belt Loop Embodiment

The implant may include 'loops' such as loops 201 illustrated in FIG. 9 to retain the driver coil 202. The driver coil passes through these loops on external surface of the implant 203.

The loops may incorporate anti-rewind features such as barbs 204.

The driver coil in this embodiment may preferentially be circular in cross section.

In one embodiment the implant 203 forms a sharp tip 205 for tissue piercing during delivery.

In another embodiment the driver coil 202 may be advance distally to the implant and form a sharp tip for tissue piercing during delivery.

The driver coil may be rewound through the loops post-delivery of the implant at the appropriate location.

6. Tissue Stabilisation

A stabiliser system may comprise a series of needles 301 as illustrated in FIGS. 11 and 12 which may be placed radially around the outside (or inside or inside and outside) of the distal end of a delivery over tube 302 (member). The needles 301 penetrate through the mucosa and a depth into the underlying tissue to stabilize these tissues during the delivery of the implant.

The needles 301 may be stored during device placement as illustrated by 303, and upon localization deployed from their resting place in the distal overtube 302 (crown/rook).

After implantation is complete the needles 301 maybe retracted.

Retractable needles are not necessary but will provide safety from accidental needle sticks to the patient and surgeon, prevent needle damage, and facilitate a lower device profile to ease insertion to the target surgical site.

There may be a plurality of needles.

There may be a surface stabilisation mechanism 304 used in conjunction with the needles to prevent the movement or binding of the proximal layer of tissue (e.g. mucosal layer in the case of perianal fistula) during implant delivery.

The driver coil may be driven by manual, automatic, powered (e.g. spring loaded, trigger or wheel activated, electrical, pneumatic or other) means.

Preferentially the driver coil is driven a number of turns clockwise to deliver the implant to the appropriate depth in the tissue location and is subsequently reversed in an anti-clockwise direction to disengage from the implant and be removed from the tissue.

Figure 13:
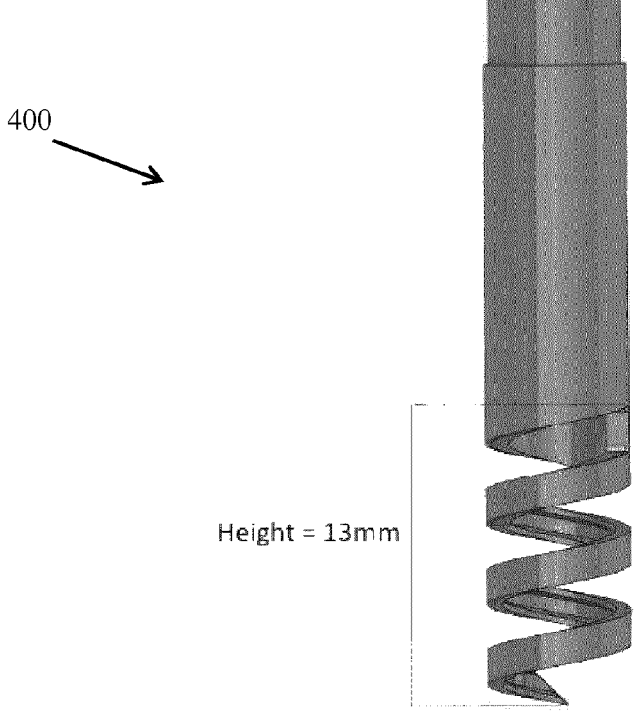
Figure 20:
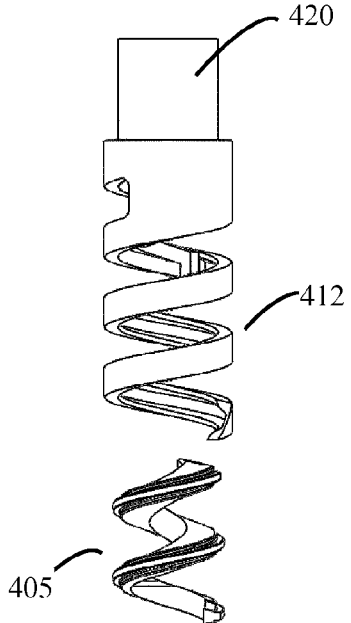
Figure 21:
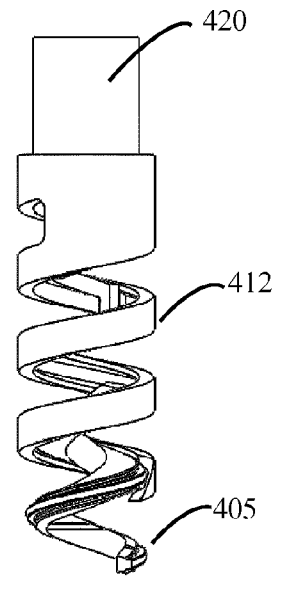
Figure 22:
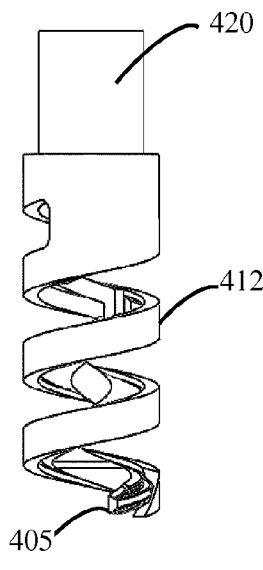
Figure 23:
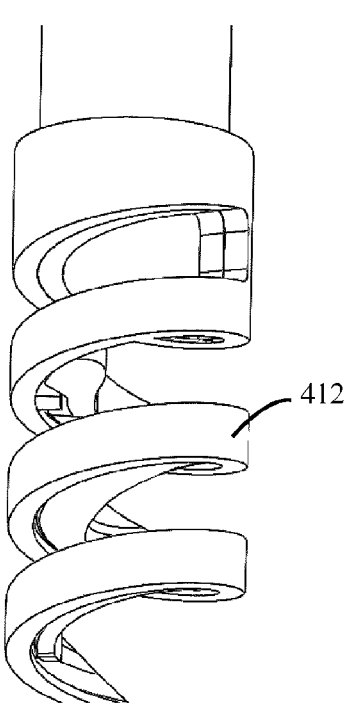
Figure 32:
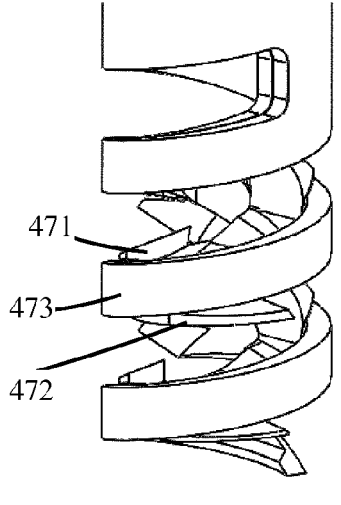
Figure 33:
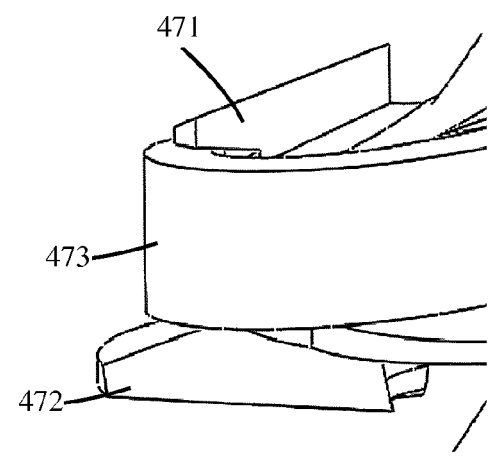

FIGS. 13 and 14 illustrate a driver coil 400 with an elongated driver coil pitch with uniform inner and outer diameter. The pitch is important to prevent tissue gripping between the struts of the driver coil. If the driver coil struts are too close to each other the tissue becomes bound and may cause damage, mechanical deformation to the coil and/or change the direction of coil travel (unpredictable off kilter delivery). These instances increase the amount of torque required to drive the coil into the tissue body and increase the torque required to retract the driver from the tissue body, increasing the coil driver requirements of delivery. Deformation of the coil driver also causes binding/locking of the un-deployed implant and may lock the implant in place permanently, an undesired result. The elongated pitch facilitates a straight coil delivery, ensuring the device is delivered into the desired targeted tissue. Typical preferred driver coil details are:

Height: 13 mm
  Pitch: 3.75 mm
  Number of turns: 2.75
  Wall thickness: 0.5 to 1.1 mm The strut height of the coil driver is important. If the height is narrow the coil driver may buckle and/or easily track off center. The coil driver strut height is preferably uniform for the entire length of the coil driver. This ensures that the weakest point of the driver coil is at the very back of the delivery coil construct. With the implant in place and the locking features the overall implant/coil driver system is a singly strong unit with all components working together to support each component (implant and driver).

A locking feature may be desirable to keep the implant and driver coil locked together during transportation, unpacking for use, and throughout the implant delivery process until the desired implant depth is reached.

Referring for example to FIGS. 15 to 23 in one embodiment the proximal end of an implant 405 has a rigid yet flexible armature 410 that flexes inwardly and latches over a detent feature 411 on the proximal end of the driver coil 412, locking the implant 405 in place during the implant loading process (at time of manufacture, or may be loaded at the time of the procedure). After the implant delivery step, the driver coil 412 is rotated in the counter clockwise direction. The force of flexion of the flexible armature 410 over the driver coil detent feature 411 is less than the force to maintain the implant in place. The driver coil is then rotated away proximally from the implant which remains embedded in the tissue.

The proximal driver coil locking feature may be square in profile, rounded in profile, or tapered in profile.

The implant flexible armature may include a ramp feature that facilitates disengagement from the driver coil.

In another embodiment the implant is locked to the driver coil using a distal cap. The cap securely covers the distal end of the delivery system. The cap may have an internal feature that abuts against the distal tip of the implant that keeps the implant secured in place until the cap is to be removed at the moment the device is ready for use.

In all cases the driver coil may have a mounting feature such as the proximal step 420 for mounting a delivery system.

Referring for example to FIGS. 24 and 25 the implant may have an outer rail (positive protrusion 430 from the outer diameter of the implant) along the outside diameter of the implant. The rail 430 acts as a guide when the implant is stowed in the driver coil to aid in the retention of the implant during delivery. The rail 430 also acts as a support (hoop strength) to maintain the shape of the implant once implanted and tissue compressive forces are acting radially outward on the compressive inward implant, to maintain tissue tract closure. The rail adds strength to the implant so that during the coil driver retraction the implant maintains its shape, this facilitates 1:1 shape match to the driver coil.

The driver coil may have a negative feature or trough 440 that accepts the implant rail 430. This serves as a guide for the implant for loading the implant and maintains the stowed configuration of the implant so that the implant does not lose its position during the implantation process. A negative feature on the inner diameter of the driver coil may be more readily manufactured.

Referring for example to FIGS. 26 and 27 in another embodiment an implant 450 tapers to a rail 451 on the outside diameter and rides in a driver coil trough 452.

Referring for example to FIGS. 28 and 29 in another embodiment an implant 460 has the shape of an I-beam in cross section providing a recess or trough 461 negative feature on the implant. The "I-beam" design provides stiffness to the implant to maintain shape post deployment as the implant compresses the tissue tract closed.

The I-beam rail adds strength to the implant so that during the coil driver retraction the implant maintains its shape, this allows for 1:1 shape to the driver coil.

The "I-beam" trough 461 rides along a positive rail feature 462 on the inner diameter of a driver coil 463. The positive rail 463 of the driver coil retains the implant 460 in the stowed position, provides a guide for loading the implant and supports the implant during delivery so that it will not become disengaged from the driver coil earlier than desired.

Referring for example to FIGS. 30 to 33 in one embodiment an implant 470 has a top and bottom feature 471, 472 that may also incorporate a barb. These features 471, 472 straddle the driver coil strut 473. One advantage of this embodiment is that it is relative easy to manufacture.

The feature 471 may be described as an internal barb and the feature 472 may be described as an external barb. The internal barbs may be configured to be positioned proximal to the succeeding coils of the driver coil preventing proximal movement of the implant relative to the driver coil. The external barbs may be configured to be positioned distal to the succeeding coils of the driver coil preventing distal movement of the implant relative to the driver coil. The external barbs have the added function of extending radially past the driver coil enabling engagement in tissue during CCW rotation. Both the internal and external barbs are shaped to have a leading edge that allows CW rotation into tissue and presents a flat surface creating anti-rewind force on CCW rotation.

Figure 34:
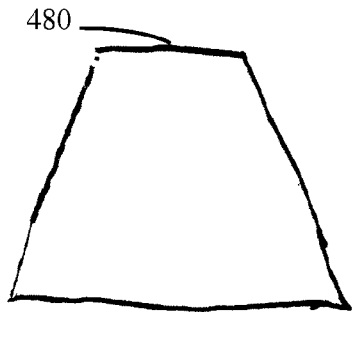
FIGS. 34 and 35 are cross sectional views of various shapes of rail.
Figure 35:
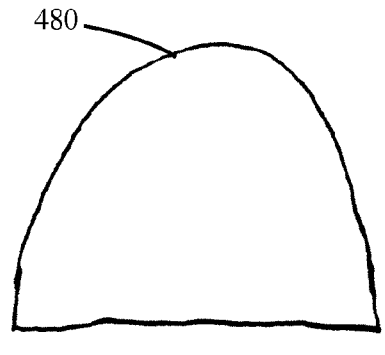

Referring for example to FIGS. 34 and 35 the positive rail feature of the implant may be tapered such that the most distal portion 480 (outer most diameter) is shorter than the adjacent base to the outer diameter of the implant. This may be readily manufactured and reduces the amount of contact with the negative trough feature of the driver coil. The distal end of the rail may be domed having a radius that reduces the contact angle with the surface of the negative trough of the driver coil and thereby, reducing the friction between the two elements.

The positive rail feature on the implant may comprise a plurality of spaced-apart segments.

Referring for example to FIGS. 36 and 37 the positive rail feature of the implant may be made up of a series of independent dome shaped segments 490 to reduce the amount of friction between the implant and driver coil.

Referring for example to FIGS. 38 and 39 the positive rail feature of the implant may be made up of a series of individual rail segments 495 to reduce the amount of friction between the implant and driver coil.

Referring for example to FIGS. 40 to 43 the negative or trough feature of the driver coil is matched to the profile of the rail of the implant. FIGS. 40 and 41 illustrate a rectilinear shape. FIG. 42 illustrates a tapered profile. FIG. 43 illustrates a curvilinear/rounded profile.

The implant can be moulded with a non-smooth surface finish to create small raised features that when they contact the smooth surface of the driver coil, friction is minimized to aide in the separation of the implant from the driver coil.

The implant may be coated with a hydrophobic coating (such as PTFE or parylene) so that when in contact with the moist tissue it can more easily separate from the deriver coil.

The driver coil may be electro-polished to enhance the surface smoothness.

The driver coil may be coated with a lubricous layer to reduce the friction between the driver coil and implant to aide in the separation.

The driver coil may be coated with a hydrophobic coating so that when in contact with moist tissue the implant and driver coil more easily separate from each other.

The implant is delivered submucosally. The length of driver coil and implant configuration is preferably in the range from 10 mm to 20 mm so that the driver coil/implant does not reach and/or penetrate through so much tissue that it may disrupt anatomical features that are not involved in the fistula tract closure procedure. Such anatomical features may include but not limited to the vagina or prostate among other local vascular branches.

Referring for example to FIG. 44 the driver coil distal tip 500 can have at least two or any number of facets 501 to form a sharp tip suitable for piercing tissue.

Referring for example to FIGS. 45 and 46 the distal tip of the driver coil may have a shaped tip to aid in the initial engagement of tissue to gain purchase and guide the drive coil the rest of the way. A flat facing engagement tip would require downward force on the tissue to make the initial puncture and begin driving the coil into the tissue. With a shaped tip, just by rotating the driver coil into the tissue the tip will begin to penetrate the surface of the tissue and self-drive into the tissue.

Referring for example to FIG. 47 the driver coil and driver shaft element may be constructed from a single piece of material in which the most distal tip 510 is manufactured in the shape of the driver coil. Proximal to the driver coil portion 511 may be a length configured to be non-torqueable (1:1 rotational motion) to enable free range of motion at a flexible/steerable joint in the drive/handle system. Proximal to the flexible section 511 may be a rigid section 512 that couples to the drive shaft's motion delivery system.

The driver coil may be attached to a drive shaft in any suitable manner.

In one case the driver coil is welded onto a drive shaft. The driver coil may be bonded onto a drive shaft. The driver coil may be screwed onto a drive shaft. The driver coil may be press fit onto a drive shaft.

Figure 50:
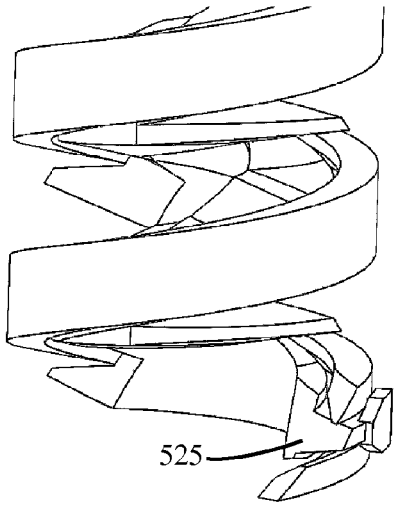

Referring to FIGS. 48 to 50 in one embodiment a driver coil 520 has a slit 521 at the distal tip 522 and the implant distal tip has a horizontal "I-beam" like feature 525. When the implant is placed in the driver coil the "I-beam" feature 525 slots into the driver coil distal slit 521 and locks in place. The lock is undone by rotating the driver coil counter clockwise with a force that is less than the force required to maintain the tissue fixation of the implant.

The distal lock configuration enables the implant and driver coil to remain locked together at the distal tip. It is not possible for tissue to work its way between the driver coil/implant interface and separate the two components or get caught in-between.

The clockwise forward driving motion of the locked components aids in keeping the driver coil and implant locked together.

The implant pitch can be elongated to aid in implantation by prevention of tissue gripping between the struts of the implant whilst maintaining the necessary strength at the proximal end to provide the compressive hoop forces required to compress the tissue tract closed. If the implant struts are too close to each other the tissue becomes bound and may cause damage, mechanical deformation to the implant and/or change the direction of the implant's path of travel (unpredictable off kilter delivery). These instances increase the amount of torque required to drive the implant into the tissue body and increase the torque required to retract the driver from the tissue body, increasing the coil driver requirements of delivery/retraction. Deformation of the implant also causes binding/locking of the un-deployed implant to the driver coil and may lock the implant in place permanently, an undesired result. The elongated pitch facilitates a straight implant delivery, ensuring the implant is delivered into the desired targeted tissue.

Figure 51:
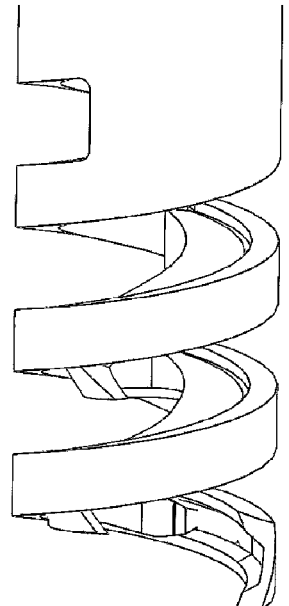
FIG. 51 is an isometric view of another implant coil with barbs.

The implant may have a series of barbs along its body to aid in retention at the intended delivery site. The barbs also provide a locking feature in the anti-clockwise (or vice versa) direction so that the driver coil can be removed. One such configuration is illustrated in FIG. 51.

One or and additional location for the placement of the barbs may be between the implant struts.

The extent to which the barbs extend between the struts is limited to prevent tissue bunching.

The barbs may extend radially from the outer edge of the implant or the barbs may extend inwardly from the inner diameter of the implant.

Figure 52:
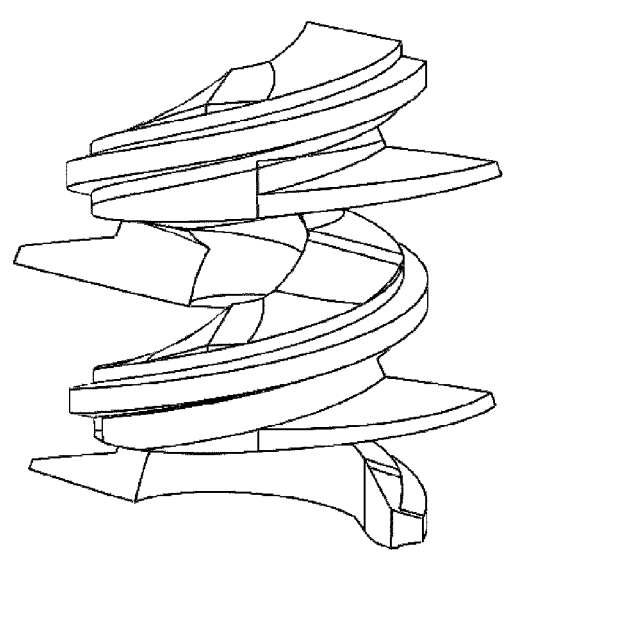
FIGS. 52 and 53 are views of another implant with barbs and an associated driver coil.
Figure 53:
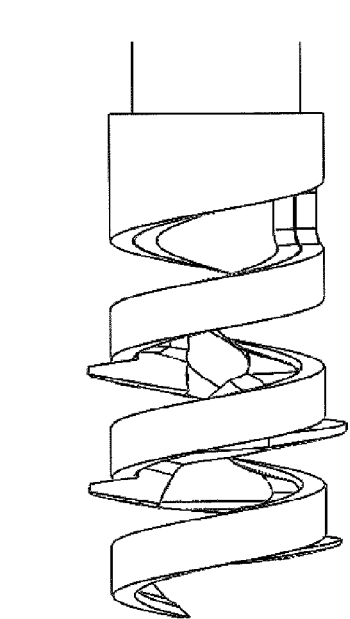

Referring for example to FIGS. 52 and 53 the barbs may extend between the struts and then extend radially outward from the outer edge of the implant. Another embodiment may have the barbs extend between the struts and inwardly. In another embodiment the barbs may extend downwardly and radially both outwardly and inwardly.

Another embodiment relies on a rough surface finish on the overall implant surface to create a high friction. When implanted in tissue, the surface friction of the implant is greater than the force required to withdraw the driver coil.

Figure 54:
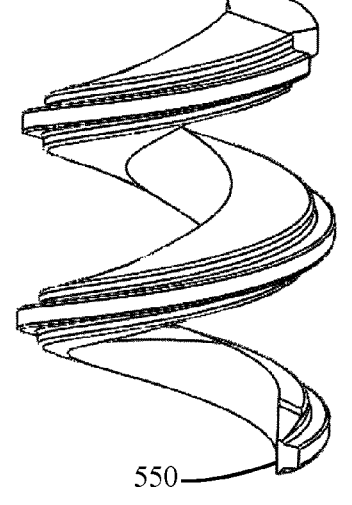
FIGS. 54 and 55 are isometric views of an implant with a tapered distal tip.
Figure 55:
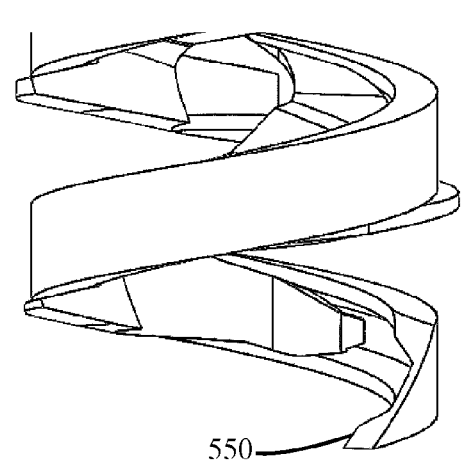

Referring for example to FIGS. 54 and 55 the distal tip 550 of the implant may be tapered to reduce the overall thickness of the implant's distal leading edge and to allow for a gradual "dilation" of tissue as the implant is driven into the tissue. Too large of a transition from the bare driver coil onto the implant may rip the tissue and not form the tract that the implant will reside implanted in. Too large of step from driver coil to implant surface increases the force required driving the device into the tissue.

The implant may be placed a distance proximally from the distal tip of the driver coil. The greater the distance the implant is placed proximal the larger the initial tissue capture will be made by the driver coil. This is advantageous to increase the size of the tissue defect to be closed by the implant.

Referring for example to FIGS. 56 and 57 in one embodiment a bioabsorbable drain 600 may be attached to the implant at the proximal surface 601. The implant may have a preformed hole 602 in which drain is inserted and heat staked, press fit into, crimped into, or glued in place.

Referring for example to FIGS. 58 and 59 in one embodiment the implant may have an eyelet 610 at the proximal end to attach the bioabsorbable drain 611.

Figure 60:
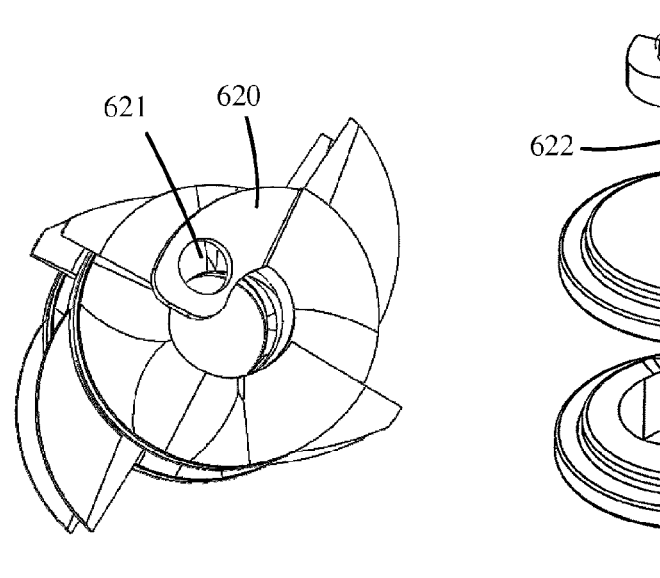
FIGS. 60 and 61 are views of a further implant and a drain.
Figure 61:

Referring for example to FIGS. 60 and 61 in one embodiment a proximal coil member 620 incorporating an eyelet 621 extends inwards of the implant to maintain an concentric axial direction of the drain 622 through the implant such that when tension is pulled on the drain the implant is not driven off center.

Figure 62A:
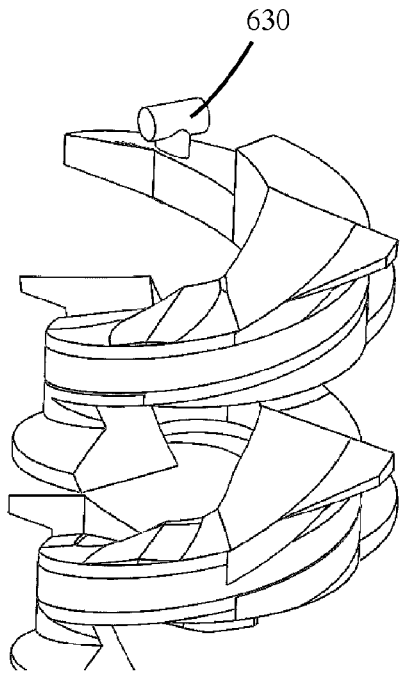
FIGS. 62a and 62b are views of another implant and a drain.
Figure 62B:

Referring for example to FIGS. 62a and 62b in one embodiment a "toggle hook" 630 is provided the proximal end of the implant and provides a purchase to attach the drain to the implant. The proximal end of the suture may have a "dead man anchor" that catches on the toggle hook 630.

Referring for example to FIGS. 62c and 62d in one embodiment the drain may be attached to a rod or series of rods that have a larger distance then the inner diameter of the implant proximal end.

In one embodiment the proximal end of the implant may have a "cleat" that the drain may be tied to or may provide as a catchment for a dead man anchor or grapple hook feature.

Referring for example to FIG. 63 the delivery system may have a handle 640 with a hand/finger activation member 641 and a shaft 642 may have a distal tip 643 for receiving the implant. The handle allows the user to securely grip the device during the procedure. The handle also incorporates a release mechanism that activates the implant delivery either through a single motion or multiple motions of activation.

Referring for example to FIG. 64 a trigger 650 may be pulled once to activate the implant drive system or it may be pulled a multiple of times. There may be a safety feature (button, latch, switch) that prevents the driver system from pre mature activation. Pulling the trigger 650 activates the delivery of the implant and upon completion the trigger 650 activates the driver coil retraction motion. A switch may be provided between delivery and retraction.

Figure 65:
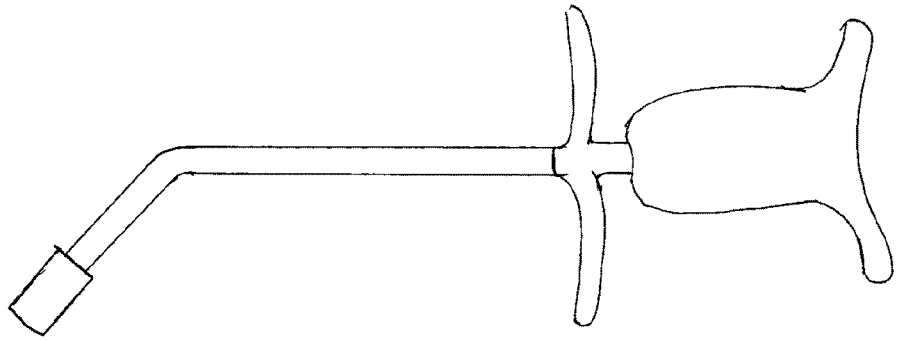

FIG. 65 illustrates another delivery system with a T-shaped handle. The operation is similar to the delivery device of FIG. 64.

Figure 66:
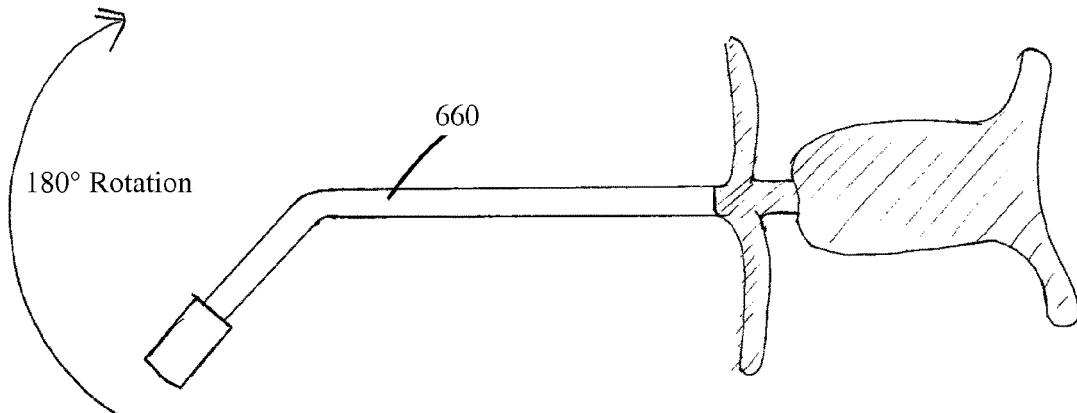

Referring for example to FIG. 66 in one embodiment the delivery system shaft 660 is pre-shaped to ensure optimal access to the treatment site in the rectum. To facilitate the usefulness of the device in the various surgical positions the patient may be placed in, the shaft may be rotatable to allow the user to position the device in an ergonomic fashion. For example when the patient is placed in the jack knife position and the surgeon is looking onto the rectum, the device facilitates ergonomic access and delivery at and below the transverse line (from 3-9 on a clock face). In the rotational shaft embodiment, the shaft handle is fixed and the shaft is rotatable at least 180 degrees so that the operator may rotate the drive shaft while maintaining an ergonomic hand position on the delivery system handle.

In the fixed T-Handle and shaft configuration, the handle is permanently fixed to a pre-bent shaft.

Figure 67:
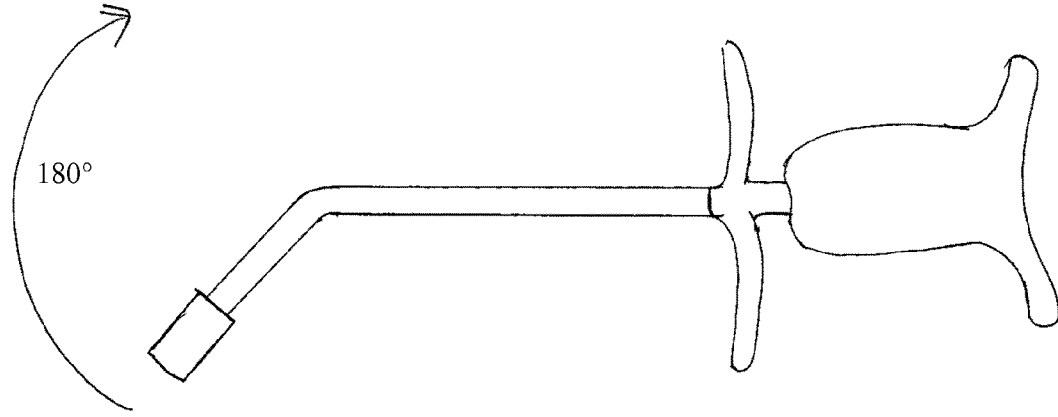

In some embodiments the entire handle and shaft assembly may be rotated so that the angled shaft is in apposition with the target tissue site. This handle design does not have preferential of orientation. This is illustrated in FIG. 67.

In one embodiment the driver shaft is steerable so that the operator can maintain a constant hand position on the handle and the control the distal tip to align to the appropriate treatment site. The shaft may be controlled by remote control, manually controlled pull wires, microfluidics and hydraulics, battery powered or wired powered motor(s), or magnetic activation.

In one embodiment the shaft may be malleable such that the operator may modify the shape of the driver shaft to best accommodate the anatomy of the patient to best deliver the implant at the treatment site.

Figure 68:
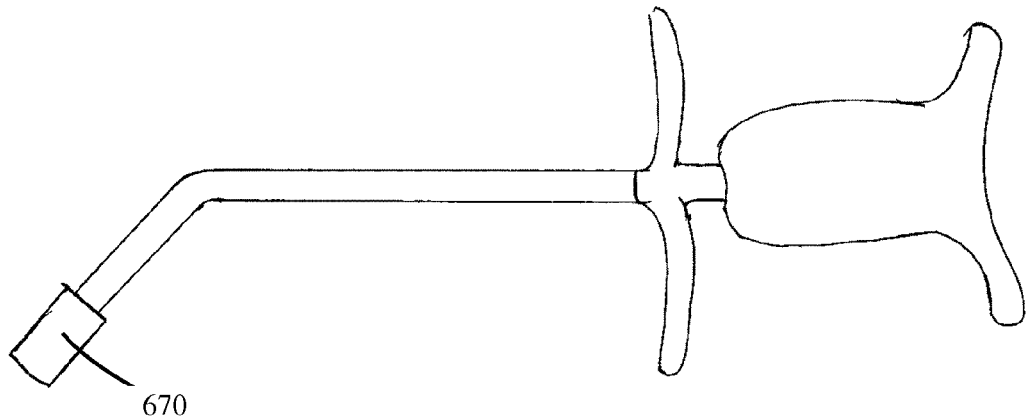

Referring for example to FIG. 68 in one embodiment the drive shaft may be made of a transparent material or may be transparent just at the portion 670 containing the driver coil and implant so that the operator may observe the distal operation of the device.

In some instances it may be advantageous to create a mucosal slit at the treatment site to uncover the sphincter muscle surface. The release of the mucosal layer prevents the tissue bunching and gripping onto the driver coil during implant delivery and the driver coil removal. Enabling a more repeatable function of the delivery system.

Prior to creating the mucosal slit, antibiotic prophylaxis treatment may be advised.

The mucosal slit may be created by electrocautery or by conventional scalpel.

Figure 69:
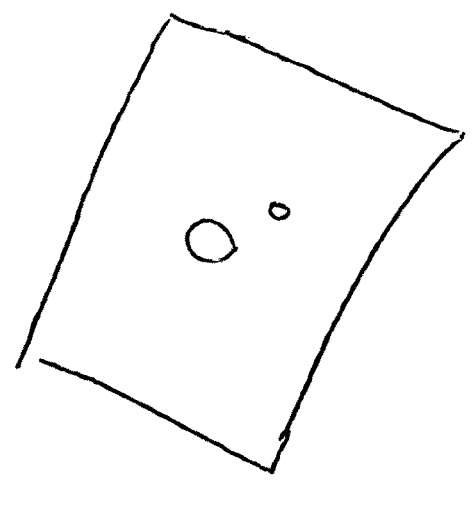
FIGS. 69 to 72 are views showing the creation of various mucosal slits.

Referring for example to FIG. 69 the mucosal slit may be made at just the point of the leading edge of the driver coil to minimize over mucosal involvement.

Figure 70:
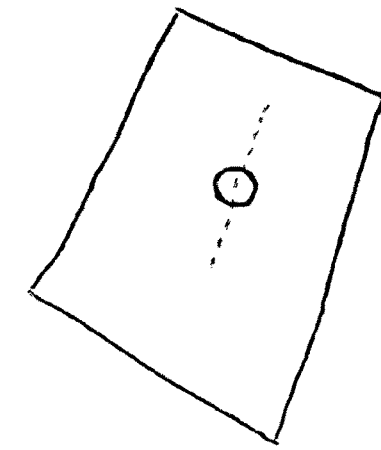
Figure 71:
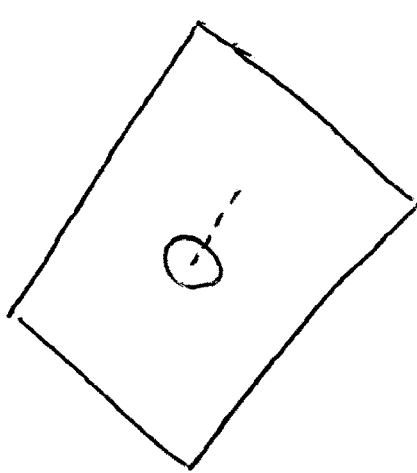

Referring for example to FIGS. 70 and 71 the mucosal slit may be made to run a partial length or the entire length of the tissue defect.

The mucosal slit may be made at minimum the length to accept the distal tip of the driver coil or as long as the user expert feels is necessary.

Figure 72:
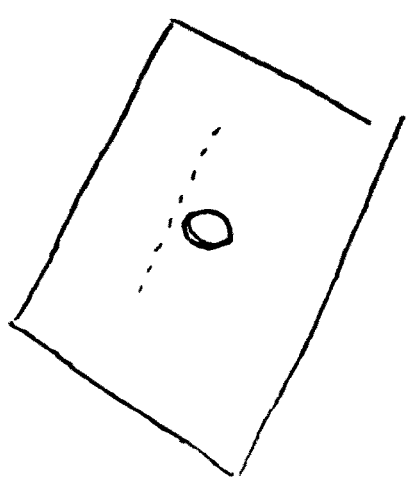

The mucosal slit may be created in a manner that it runs vertically through or adjacent to [FIG. 72] the tissue defect.

The mucosal slit may be created in a manner that it runs horizontally through or adjacent to the tissue defect.

The mucosal slit may be created in a manner that it runs diagonally through or adjacent to the tissue defect.

It may be necessary post implant delivery and driver coil retraction to close the mucosal slit. This can be achieved in any number or combination of ways/methods.

Any one of the below methods of closing the mucosal slit may be applied post implant delivery and driver coil retraction, at any moment during the delivery process, or prior to the delivery process (implant delivered and driver coil removed).

A stitch may be placed along the mucosal slit to appose the two side of the slit together.

In an additional embodiment, the suture may provide a pain relief and antibacterial treatment to the mucosal wall. The mucosal wall is dense in capillary's and an ideal place for therapeutic particle/molecules/drug delivery.

In one method a patch that is capable to adhere to the mucosal wall maybe placed in a manner that it bridges the site of the planned mucosal slit prior to the mucosal slit creation to prevent extensive tissue splitting. The patch has an elastic property that allows the material to return to the steady state and appose the slit ends together post procedure.

In an additional method a patch may be placed across the mucosal slit post implantation procedure in a manner that it apposes the edges of the slit together.

In an additional embodiment, the patch may provide a pain relief and antibacterial treatment to the mucosal wall. The mucosal wall is dense in capillaries and an ideal place for therapeutic particle/molecules/drug delivery.

In one method the compression forces of the implant is capable of apposing the mucosal.

It may not be necessary to close the mucosal slit.

Antibiotic prophylaxis treatment may be advised.

Bleeding is controlled by surgical technique. Compression, injection of adrenaline, electrocautery instrumentation.

A bioabsorbable drain is attached or may be connected to the implant. The drain maintains tract patency throughout the healing process so that no portion of the tract heals prior to the external opening healing. This prevents any remaining foreign material or infected bodies from remaining in the tract and forming an infected sinus. The drain allows any material in the tract to be extruded outwardly through the external tract opening.

The drain may be attached or maintained in a position proximal to the proximal end of the implant throughout shipping, the implantation process, and during the healing process such that the drain may not be removed from the device or the tissue tract.

Figure 73:
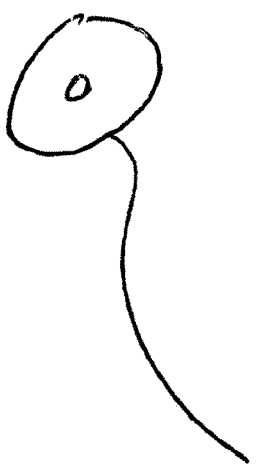
FIG. 73 is a perspective view of another drain of the invention.

Referring for example to FIG. 73 in one embodiment the drain has a bioabsorbable disk structure on the proximal end that is larger than the proximal inner diameter of the implant. The disk prevents the drain from being removed prematurely through the external tract opening. The drain may be tied to the disk, heat staked to the disk, thermoformed from the same extrusion of the drain material "bump" process, glued, or knotted in such a way the drain cannot be removed from the disk.

In one embodiment the drain has a series of knots tied along the proximal length. With at least one knot larger than the proximal inner diameter of the implant to keep the drain from being removed through the external tract opening. A series of knots distal to the most proximal hoop of the implant may serve as method to prevent the drain from moving towards the internal opening of the tract.

The drain may be secured to the outer skin of the buttocks using a skin adhesive bandage capable of withstanding daily patient activates for a course of at least 4 weeks, such has walking sitting, scooching, wiping, washing with water and/or typical human cleaning solutions, and pulling at the bandage.

A method to clean the entire length of the tissue tract prior to internal opening tract closure may be desirable to remove granulation tissue, foreign material, infected material, and to disrupt the epithelized tract lining if one exits.

One method of cleaning the tract is to run a rigid brush though the fistula tract in which the brush bristles are numerous, rigid and provide radial force against the wall of tract to capture material and at the same time "scuff" the walls of the tract.

Another method of cleaning the tract is by removing the tract and any comprised tissue by means of partial or full fistulectomy. Another method of cleaning the tract is by means of laser or RF ablation or by mechanical removal of tissue by means of curette The tract may be flushed with sterile water, saline, hydrogen peroxide to aid in cleaning the tract through dilution and bacterial agents. Flushing may be carried out by abutting a syringe against the external, internal or both tissue tract openings. Flushing may also be carried out by attaching a micro catheter to a syringe and inserting the distal end of the micro catheter into the external, internal or both tissue tract openings.

In some embodiments the implant and/or drain combination may be coated with, seeded, constructed (entirely or partially) of a growth enhancement medium and/or a therapeutic agent.

The implant may be used for closing the internal and/or external opening in order to retain a growth enhancement medium or material, or therapeutic agent in place during healing.

Growth factors may include, but are not limited to: Stem cells (e.g. adipose-derived mesenchymal stem cells or other mesenchymal stromal stem cells), extra cellular matrix material or slurry, a combination of stem cells and extracellular matrix or slurry, tissue growth factors, blood plug, collagen matrix, endothelial cells, altered/engineered endothelial cells, blood serum, glues, growth factor, pre-clotted blood plug, culture or media supplement comprising a cell and extra cellular matrix material and medium for encouraging growth enhancement.

The implant may be used to aid in the therapeutic administration of regenerative materials (such as listed above) to repair or enhance weakened or damaged tissues in humans or animals such as subcutaneous tissue, organs, and joints. In one case the implant is used in the treatment of perianal fistula.

To enhance and facilitate the healing of perianal fistulas, or other soft tissue wounds, it may be desirable to seed the area of the fistula with tissue growth materials such as stem cells (e.g. adipose-derived mesenchymal stem cells or other mesenchymal stromal stem cells), extra cellular matrix material or slurry, a combination of stem cells and extracellular matrix or slurry, tissue growth factors, blood plug, collagen matrix, endothelial cells, altered/engineered endothelial cells, blood serum, glues, growth factor, pre-clotted blood plug, culture or media supplement comprising a cell and extra cellular matrix material and medium for encouraging growth enhancement.

In one embodiment the implant may be fully or partially constructed from an appropriate growth enhancement medium or material, or therapeutic agent. The implant may be placed at the internal opening of the fistula tract, or at the external opening or both. A drain may or may not be used in conjunction with any configuration of the implant and may be either comprise a bioabsorbable material (e.g. a PLGA construct), or non-bio-absorbable material (e.g. nylon), or alternatively may be fully or partially constructed from an appropriate growth enhancement medium or material, or therapeutic agent.

In the case where the implant is located at the internal opening of the fistula tract, a drain may extend through the tract and exit at the external opening of the fistula tract.

In the case where the implant is located at the external opening of the fistula tract, a drain may extend through the tract and exit at the internal opening of the fistula tract.

In the case of an implant is used at both the internal and external opening, a drain may be captured between the two implants and contained in the tract of the fistula tract.

In another embodiment the implant or drain may be constructed from a suitable bio-absorbable material and doped or seeded or coated with growth enhancement medium or material, or therapeutic agent such as described.

The implant may be used as a tract closure mechanism at either the internal opening or external opening or both for the purpose of maintaining the growth enhancement medium or material, or therapeutic agent in place during healing.

One method of delivering and retaining a growth enhancement medium or material, or therapeutic agent such as; stem cells (e.g. adipose-derived mesenchymal stem cells or other mesenchymal stromal stem cells), extra cellular matrix material or slurry, a combination of stem cells and extracellular matrix or slurry, tissue growth factors, blood plug, collagen matrix, endothelial cells, altered/engineered endothelial cells, blood serum, glues, growth factor, pre-clotted blood plug, culture or media supplement comprising a cell and extra cellular matrix material and medium for encouraging growth enhancement, is by first injecting the material into the internal opening or the external opening or both openings of the fistula tract.

Figure 74:
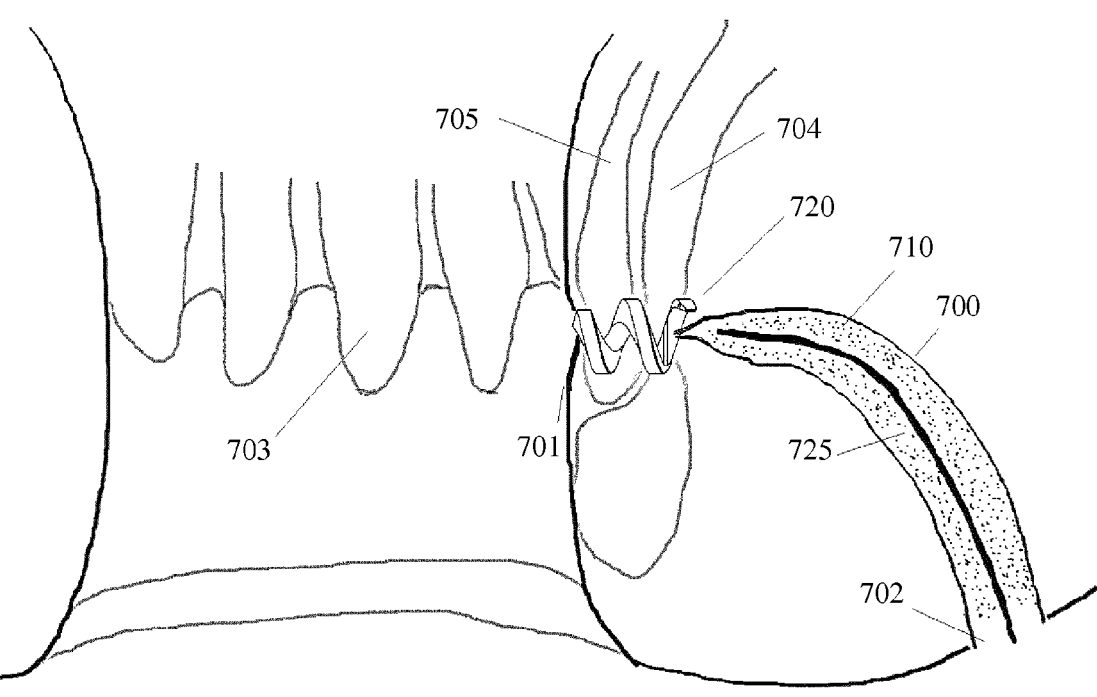
FIG. 74 is a diagram of a fistula tract with a growth enhancement medium in place and an internal opening of the tract closed by an implant.
Figure 75:
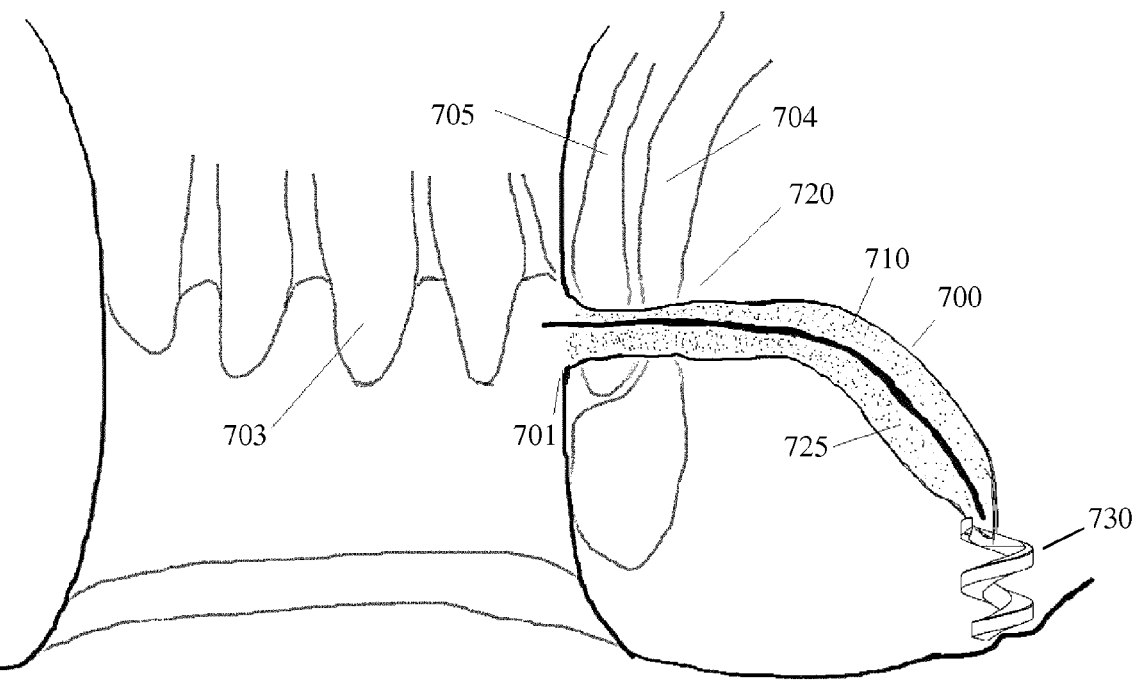
FIG. 75 is a diagram similar to FIG. 74 with an external opening of the tract closed by an implant.
Figure 76:
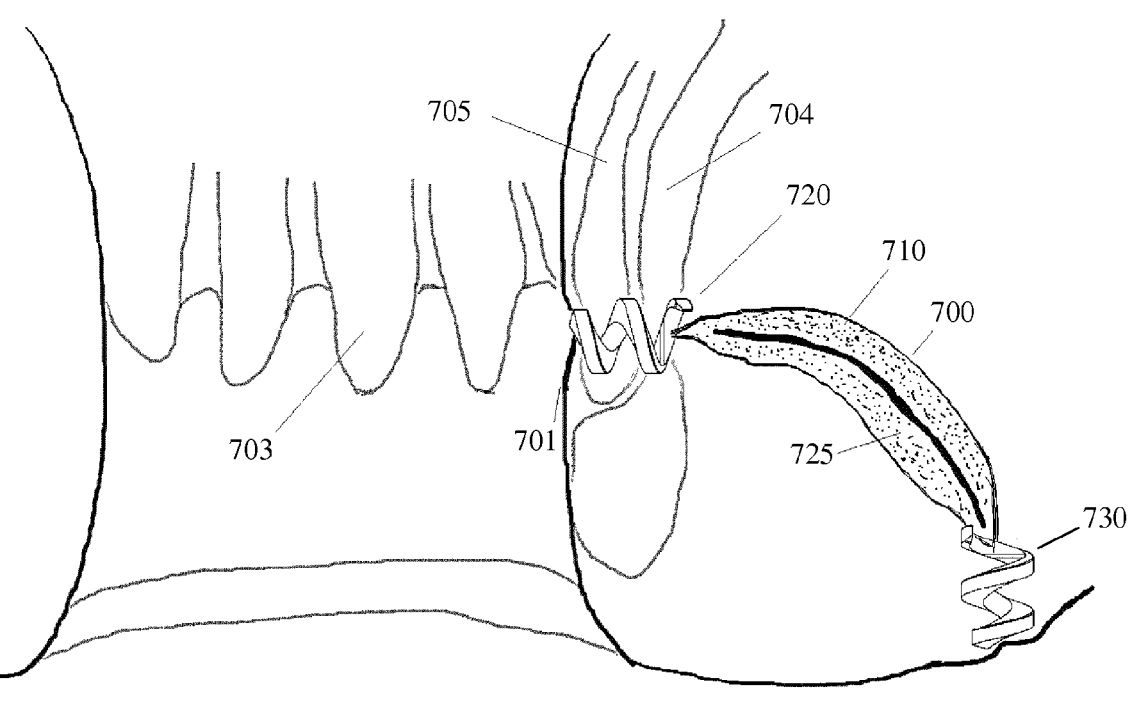
FIG. 76 is a diagram similar to FIG. 74 with a first implant closing an internal opening and a second implant closing an eternal opening of the fistula tract.

In FIGS. 74 and 75 the reference numerals refer to the following:

700 fistula tract
701 internal opening
702 external opening
703 dentate line
704 external sphincter muscle
705 internal sphincter muscle
710 growth enhancing medium
720 implant at internal opening
725 drain
730 implant at external opening When the desired material has been placed in the tract, the fistula may be closed at the internal opening using an implant device as shown in FIG. 74. The implant provides an optimized tract closure compared to surgical advancement flap or other closure techniques. The implant offers a repeatable and secure closure that can withstand anatomical pressures, ensuring that the material is not able to migrate out of, or be expunged through, the fistula tract internal opening. Alternatively, the implant may be used to close the external opening as shown in FIG. 75. In some cases an implant is used to close both the internal and external openings of the fistula tract as illustrated in FIG. 76. A drain may or may not be used in conjunction with any of these cases.

Figure 77:
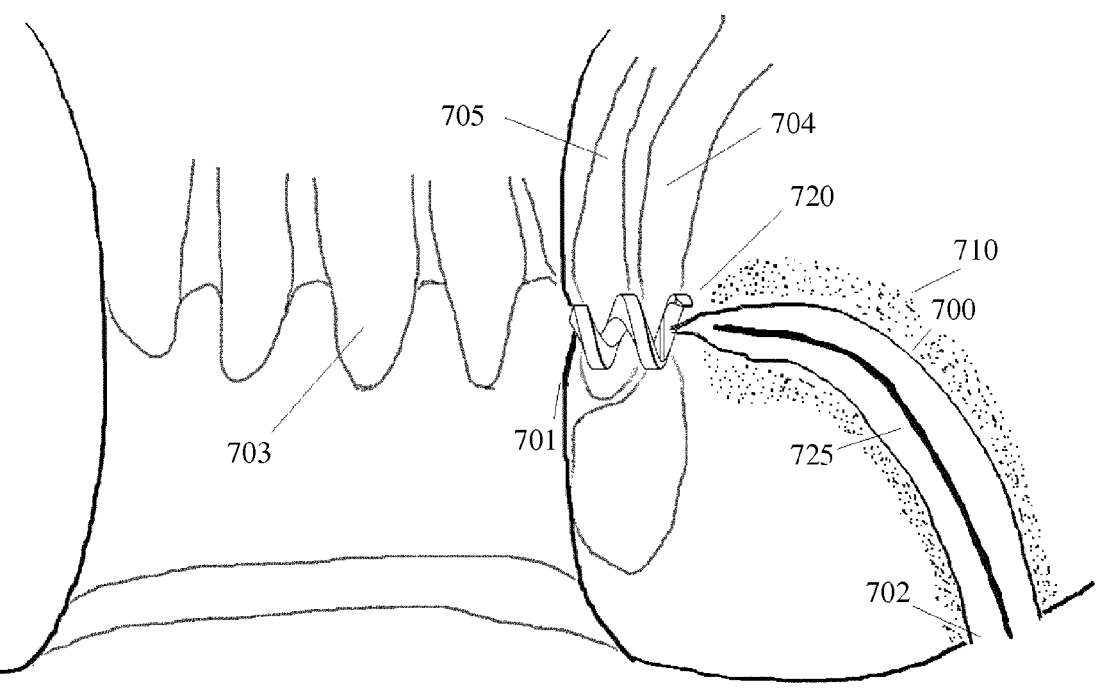
FIG. 77 is a diagram of a fistula tract with a growth enhancement medium extending into tissue surrounding the tract and an internal opening of the tract closed by an implant.
Figure 78:
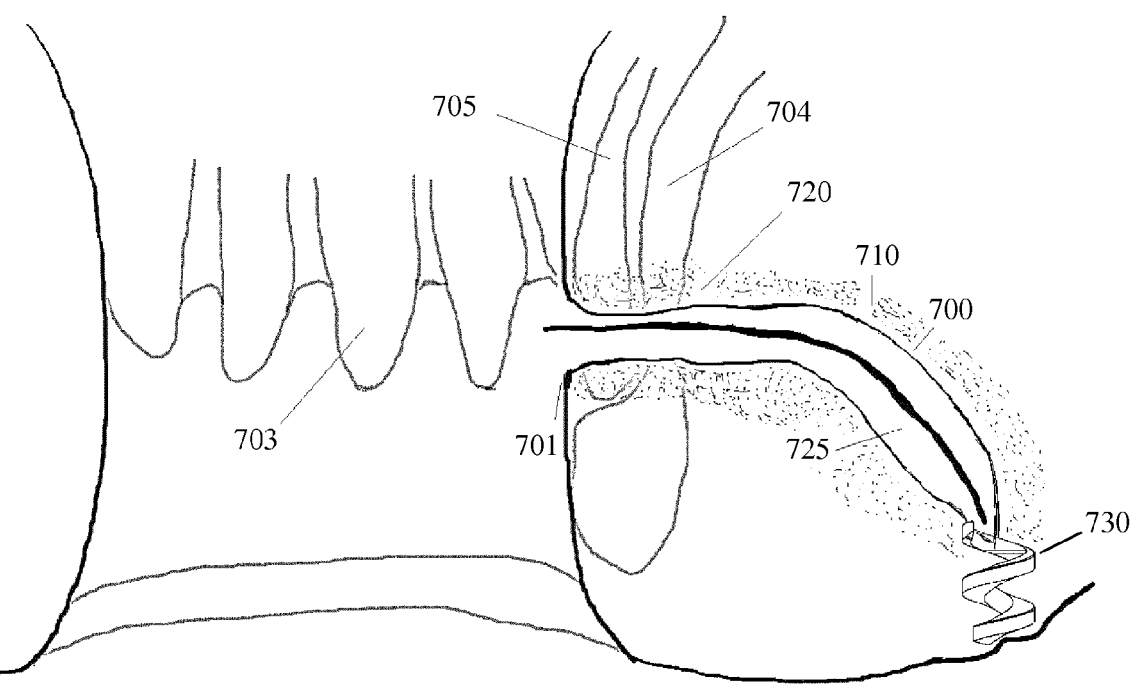
FIG. 78 is a diagram similar to FIG. 77 with an external opening of the tract closed by an implant.
Figure 79:
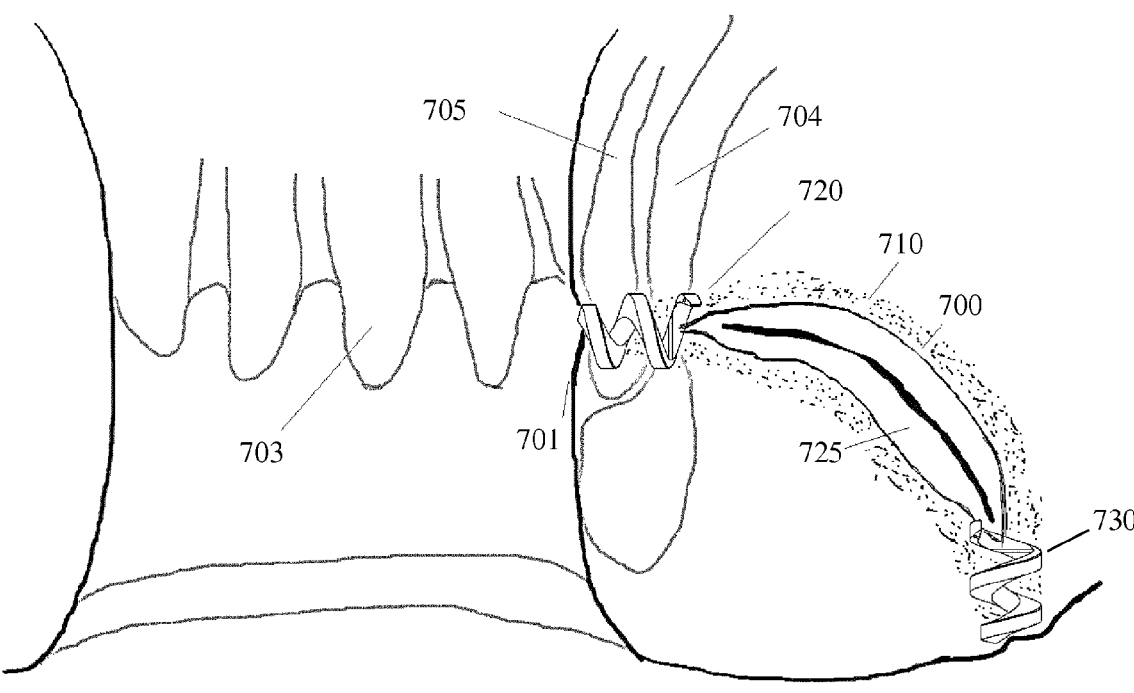
FIG. 79 is a diagram similar to FIG. 77 with a first implant closing an internal opening and a second implant closing an external opening of the fistula tract.

Another method of delivering and retaining a growth enhancement medium or material, or therapeutic agent is by first injecting the material along and around the length of the fistula tract. Once the desired material has been placed in the tissue surrounding tract and/or in the tissue comprising the wall of the fistula tract, the tract may be closed at the internal opening with an implant device as shown in FIG. 77. The implant provides a repeatable and secure closure that can withstand anatomical pressures, ensuring the material is not able to migrate out of, or be expunged through, the fistula tract internal opening. The implant may also be used to close the external opening as shown in FIG. 78. The implant may be used to close both the internal and external openings of the fistula tract as shown in FIG. 79. A drain may or may not be used in conjunction with any of these cases.

Figure 80:
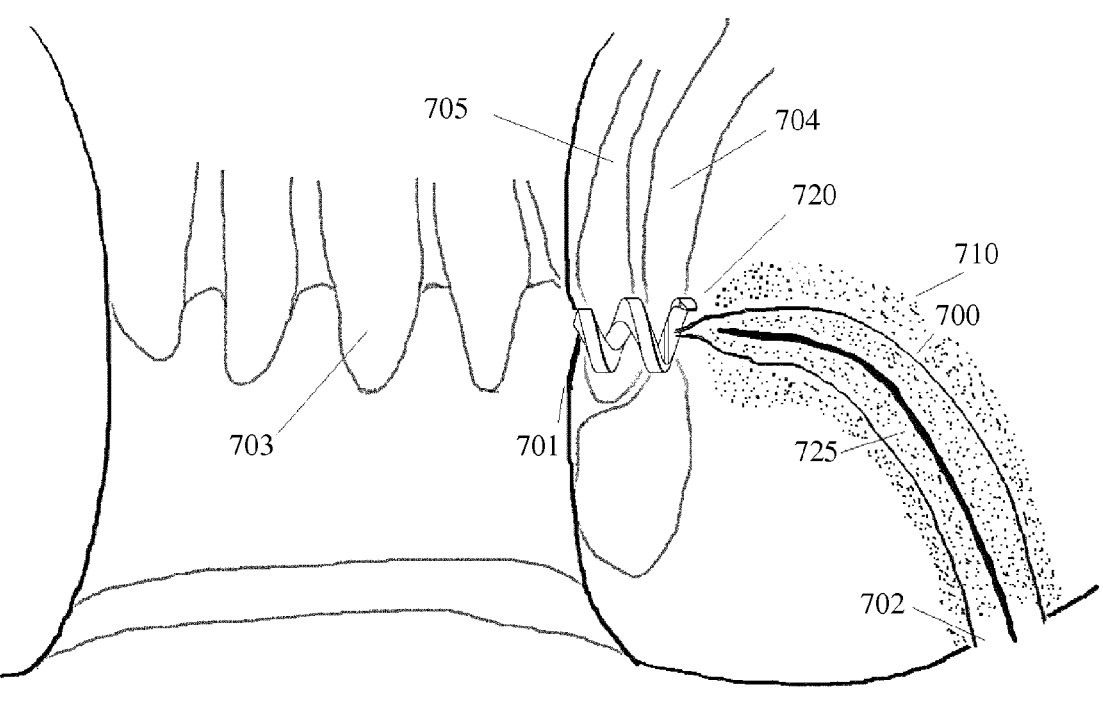
FIG. 80 is a diagram of a fistula tract with a growth enhancement medium in the tract and extending into tissue surrounding the tract and an internal opening of the tract closed by an implant.
Figure 81:
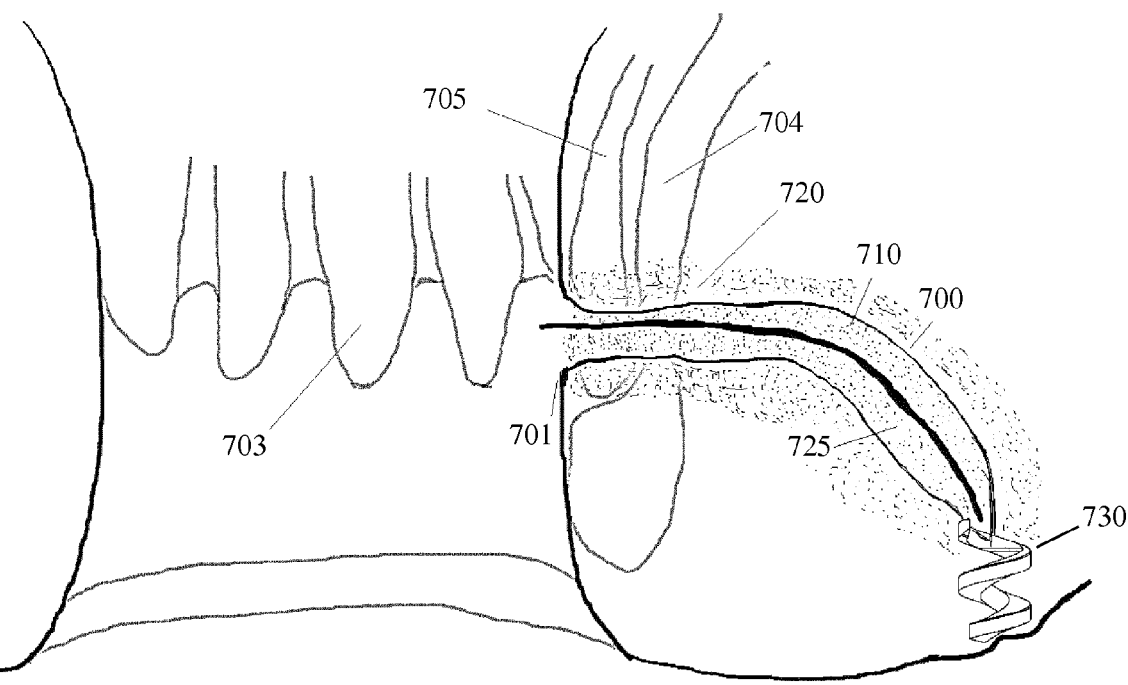
FIG. 81 is a diagram similar to FIG. 80 with an external opening of the tract closed by an implant.
Figure 82:
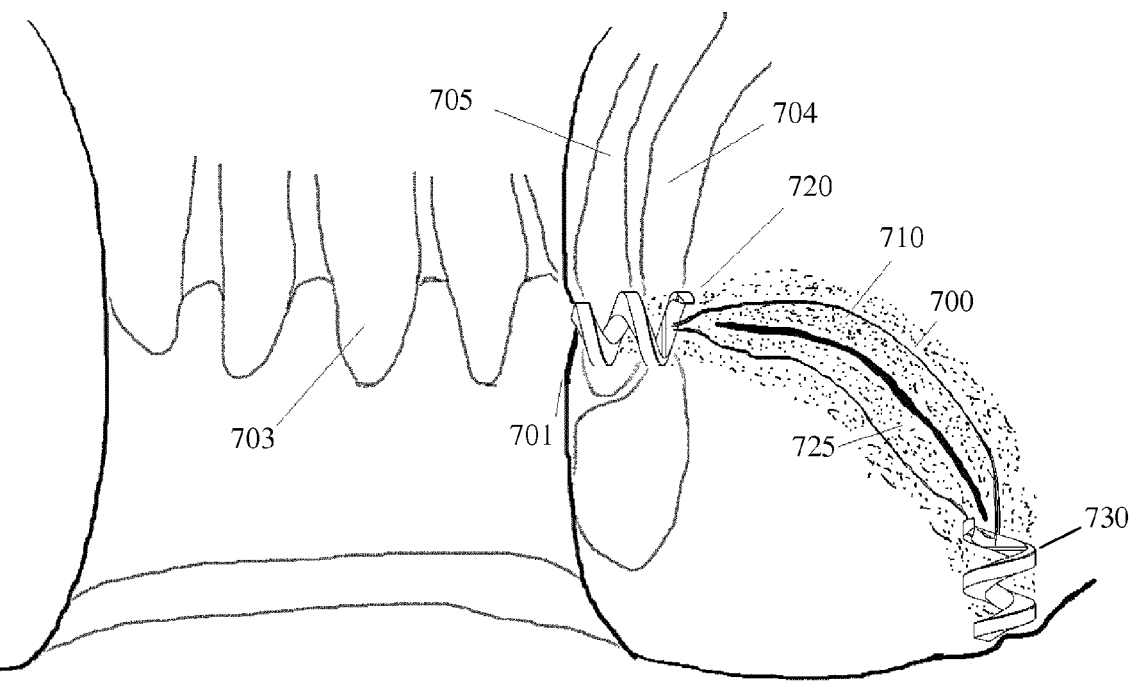
FIG. 82 is a diagram similar to FIG. 80 with a first implant closing an internal opening and a second implant closing an external opening of the fistula tract.
Figure 83:
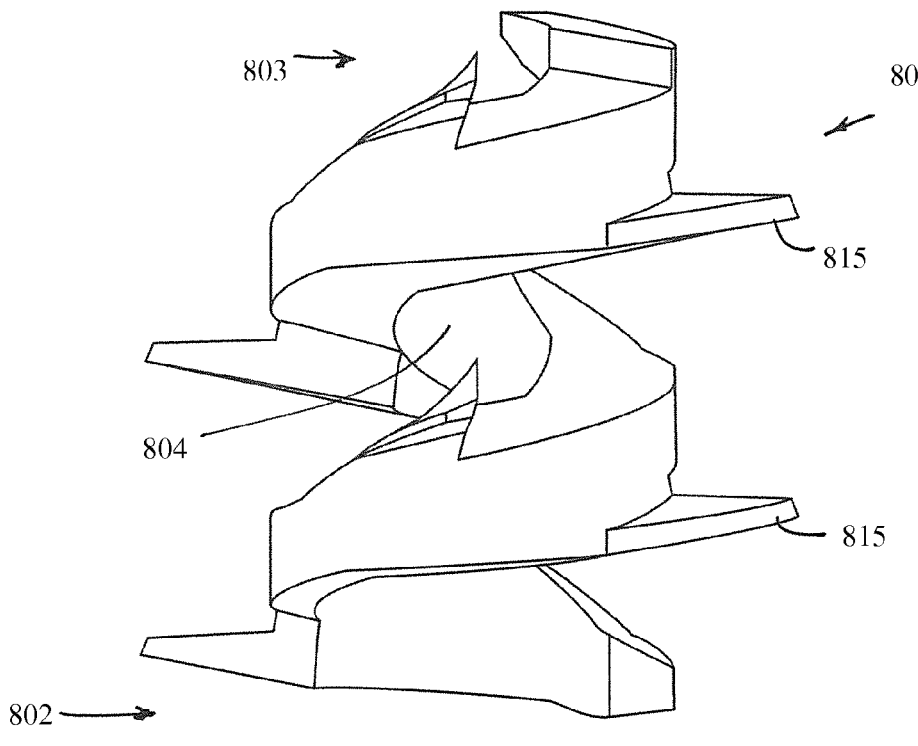
FIGS. 83 to 86 are isometric views of an implant according to the invention in different orientations.
Figure 84:
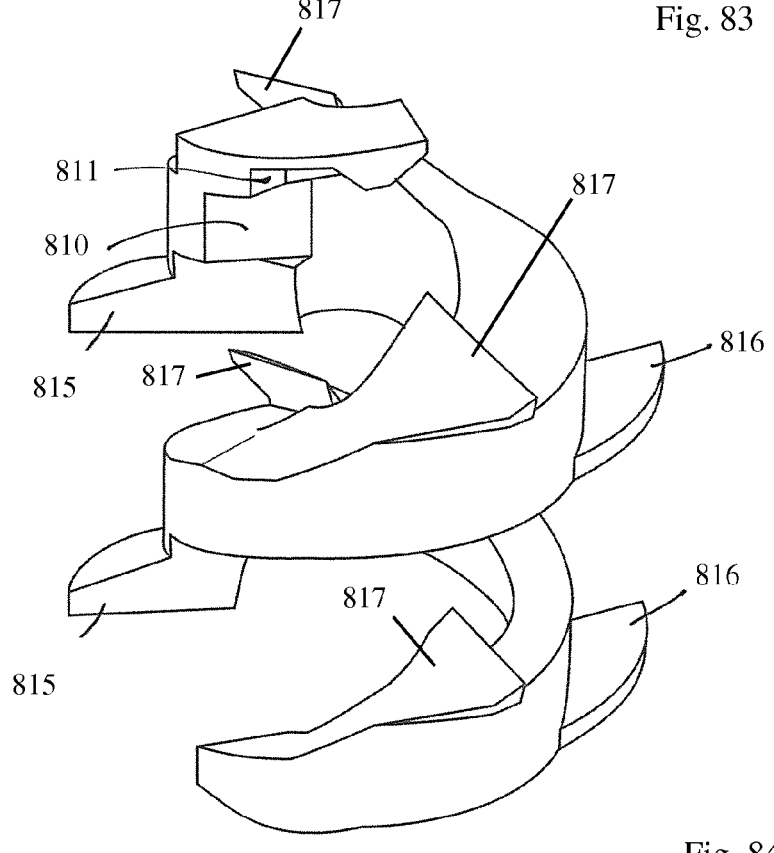
Figure 85:
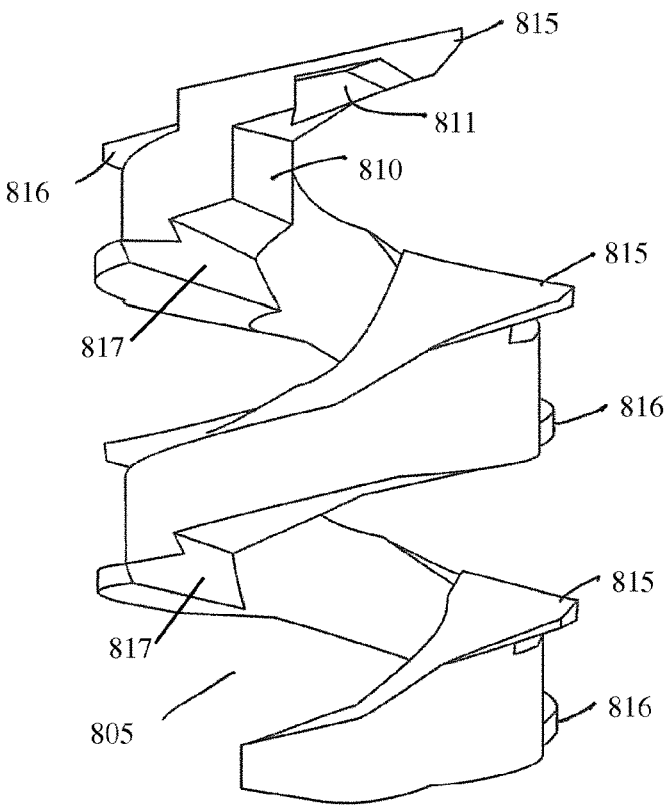

A further method of delivering and retaining a growth enhancement medium or material, or therapeutic agent is by injecting the material both internally to the fistula tract and along and around the length of the tract. Once the desired material has been delivered, the tract may be closed at the internal opening with an implant device as shown in FIG. 80. The implant offers a repeatable and secure closure that can withstand anatomical pressures, ensuring the material is not able to migrate out of, or be expunged through, the fistula tract internal opening. Alternatively, an implant may also be used to close the external opening as shown in FIG. 81. In addition the implant may be used to close both the internal and external openings of the fistula tract as shown in FIG. 82. A drain may or may not be used in conjunction with any of these cases.

Figure 86:
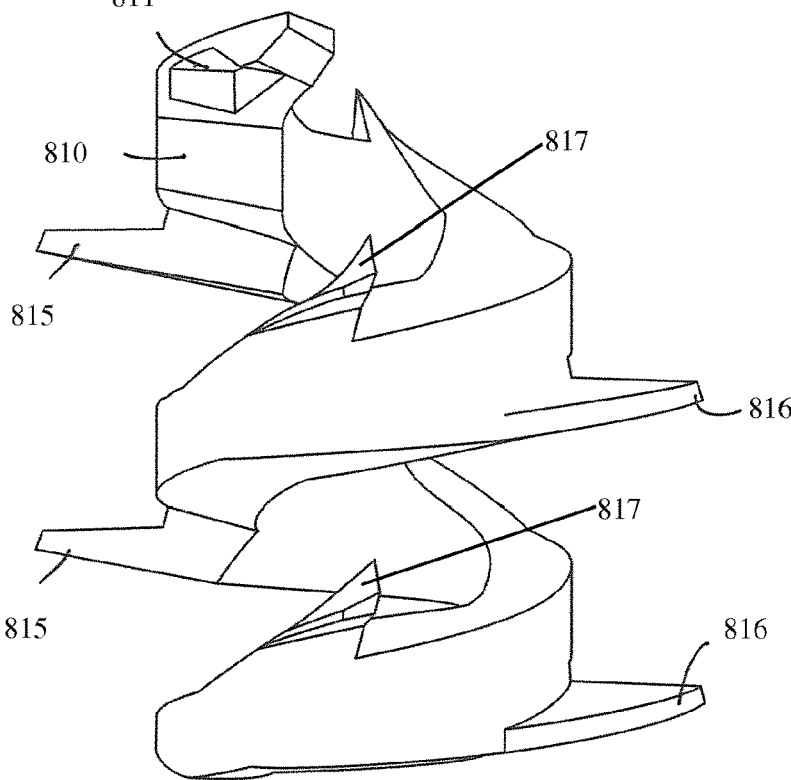

Referring for example to FIGS. 83 and 92 to 96, there is illustrated an implant 801 for closing an opening in tissue such as a sinus or a fistula, for example, a perianal fistula. The implant 801 comprises a coil having an outer diameter that is substantially uniform along the length of the coil and an inner diameter that is tapered between the ends of the coil. The coil has a distal tissue insertion end 802 and a proximal driver end 803 and an internal passageway 804 in the coil tapers from a wide diameter opening 805 at the distal end 802 to a narrow diameter opening 806 at the proximal end 803 as most clearly shown in FIG. 86. The implant typically tapers from an internal diameter at the distal end of from 1 to 6 mm to an internal diameter of from 0.5 mm to 2 mm at the proximal end. The pitch of the coil of the implant is typically from 2 mm to 4 mm.

The implant coil has an engagement feature which in this case is towards the proximal end of the implant and in this particular case comprises a shoulder 810. The engagement shoulder is configured for engagement with a corresponding engagement feature of a driver coil as described in more detail below. The implant also has an interlock feature which in this case comprises a recess or channel 811 which is releasably interlocked with a corresponding feature of a driver.

The implant coil comprises an outer rail that is formed by first and second arms 815, 816 that extend outwardly of the coil. The arms are adapted to receive a portion of a driver coil therebetween. The first arm and the second arm comprise a plurality of spaced-apart segments, 815, 816 respectively, that are spaced-apart along the implant coil. It will be noted that the segments of the first arm 815 are offset from the segments of the second arm 816. At least some of the rail segments 815, 816 comprise an anti-rewind feature (such as a barb) which is configured to facilitate penetration of tissue but will act to prevent re-wind of the implant coil from the tissue.

The implant coil 801 may be used in association with a delivery device for delivery of the implant into tissue. One particular delivery or driver coil 820 is illustrated particularly in FIG. 87. FIGS. 92 to 95 illustrate an implant coil 801 mounted to the driver coil 820. The driver coil 820 has a distal tip section 821 which is adapted from piercing tissue and/or for compression of tissue. A proximal end 822 of the delivery device is adapted for mounting to a handle for turning by a user or may comprise a shaft which may be power driven.

The driver coil is a straight helix having a constant pitch. In this case, neither the inner nor the outer of the driver coil are tapered. The inner diameter of the driver coil is configured to receive the implant coil and is typically from 4 mm to 6 mm. The outer diameter is typically from 6 mm to 8 mm and the wall thickness is from 0.5 mm to 1 mm. The pitch is typically from 2 mm to 4 mm. The driver coil comprises coil struts 825 and the height of the struts is typically from 0.5 mm to 2 mm. The driver coil may comprise from 2 to 5 turns, such as 2.75 turns.

When the implant coil is mounted in the driver coil the struts 825 of the driver coil are embraced between the rail arms 815, 816 of the implant coil so that the arms 815, 816 of the implant coil travel on the track provided by the struts 825 of the driver coil.

The driver coil 820 comprises an engagement feature 827 for releasably engaging with an implant 801. When the driver coil is rotated in a clockwise direction, the engagement projection 827 engages with a corresponding shoulder 810 of the implant coil 801. On rotation of the driver coil in the opposite direction, the driver coil 820 is moved independently of the implant coil 801 to facilitate removal of the driver coil and leaving the implant coil in situ.

In this case there is also a releasable interlock between the driver coil and the implant. The interlock comprises the recess or channel 811 in the implant coil and a corresponding projection 828 of the driver coil. In some cases such an interlock is not essential.

In one case the delivery coil 820 is attached to a delivery tube 830. The delivery tube 830 may incorporate the engagement feature 827 which engages with the proximal end of the implant 801. The delivery tube may also incorporate the interlock feature such as the projection 828 which engages with an interlock feature of the implant 801 such as the recess or channel 811. FIG. 91 illustrates the delivery coil 820 separated from the delivery tube 830. The may be attached in any suitable manner. In some cases the delivery coil 820 and tube 830 may be monolithic.

Figure 89:
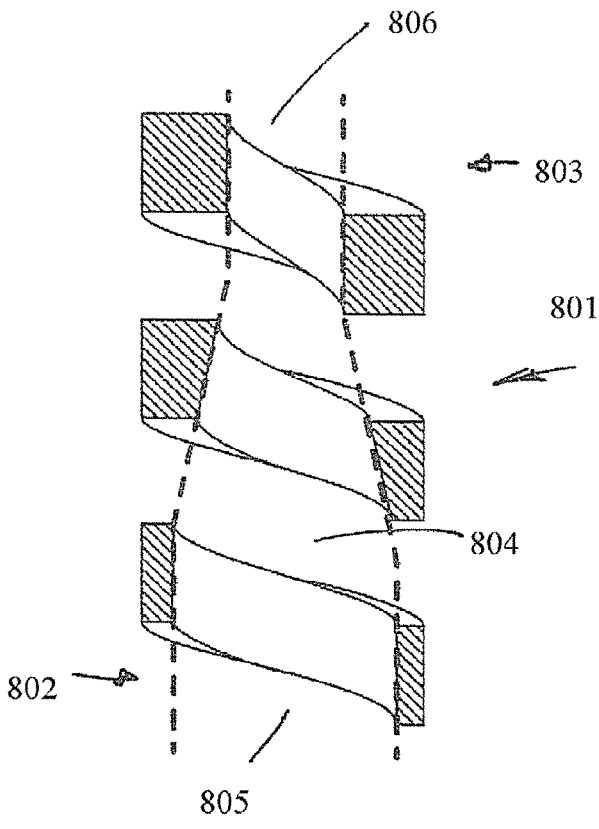
FIG. 89 is a longitudinal cross sectional view of the implant.
Figure 90:
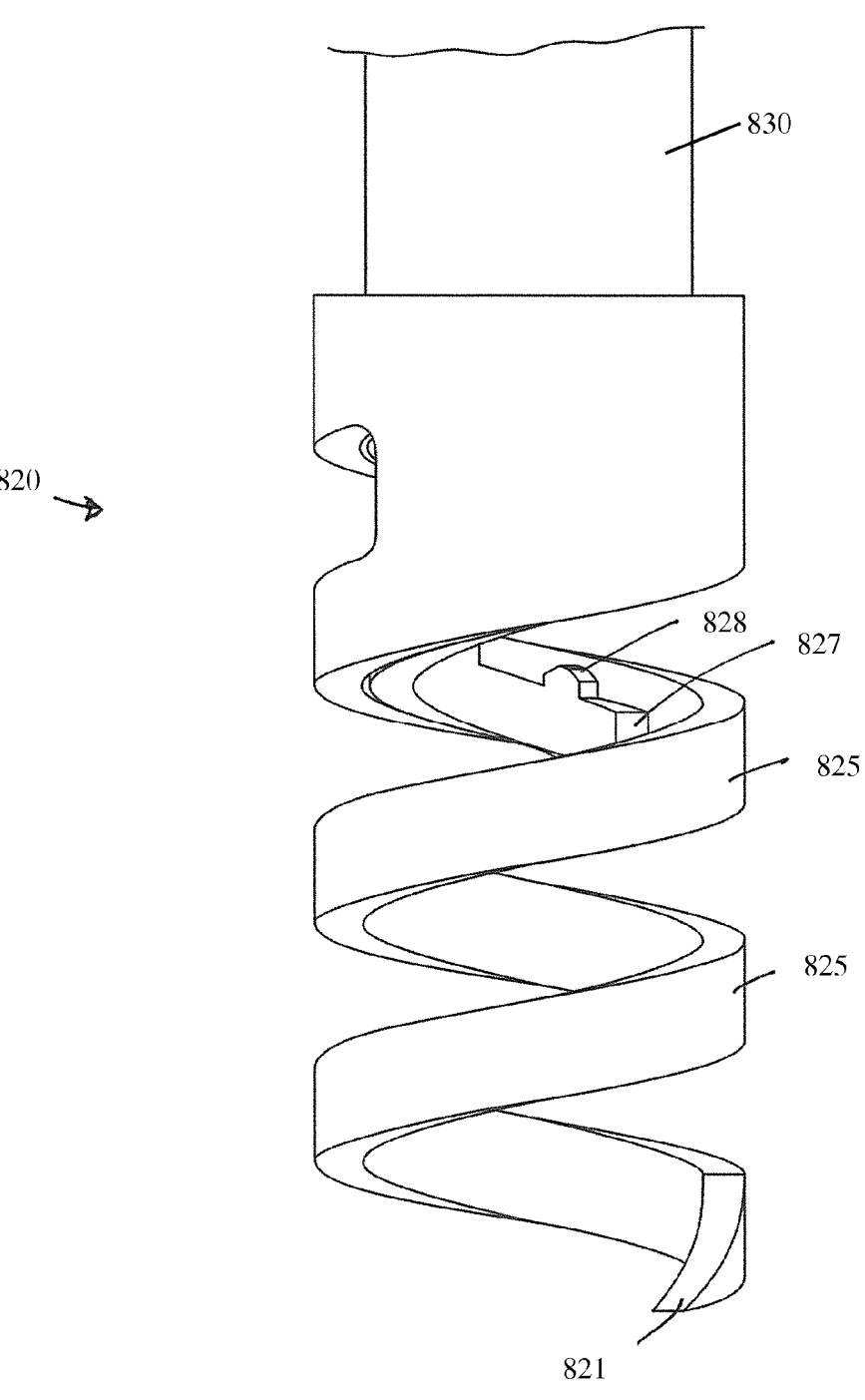
FIG. 90 is an isometric view of a driver coil of the invention.
Figure 92:
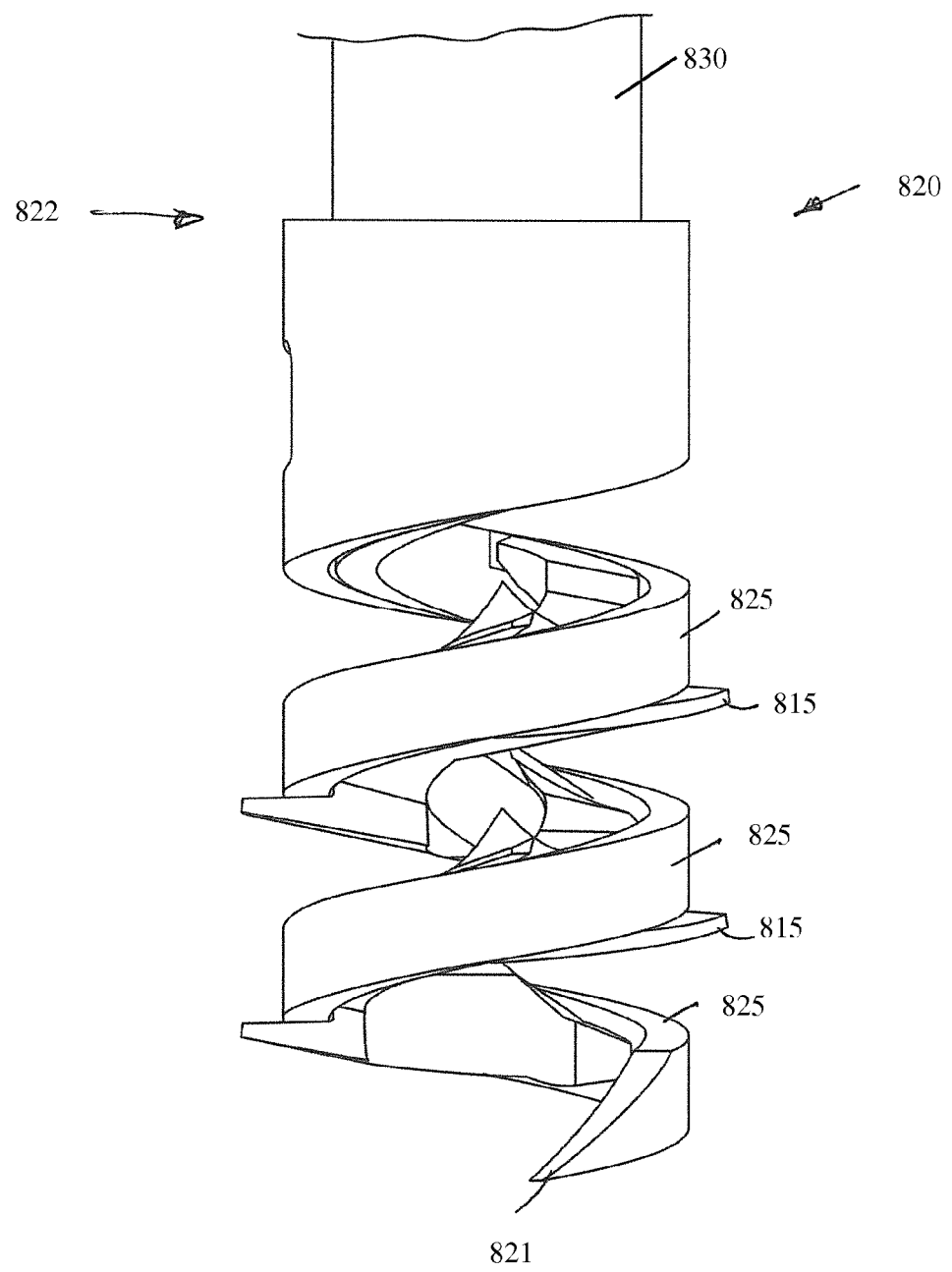
FIG. 92 is an isometric view of the driver coil with an implant positioned within.

It will be noted that in the delivery configuration illustrated in FIGS. 89 and 90 the distal end of the driver coil extends distally beyond the distal end of the implant. In the invention the distal end of the delivery coil 820 effects the initial gathering and compression of tissue.

The delivery coil fully supports the full length of the implant 801 (i.e. the implant 801 is housed within the delivery coil 820). The delivery coil forms a piercing sharp tip 821 at its distal end.

The distal tip 821 of the delivery coil 820 acts to gather the first (largest/distal) loop of tissue and leads this tissue into the tapered compression zone of the implant.

Figure 93:
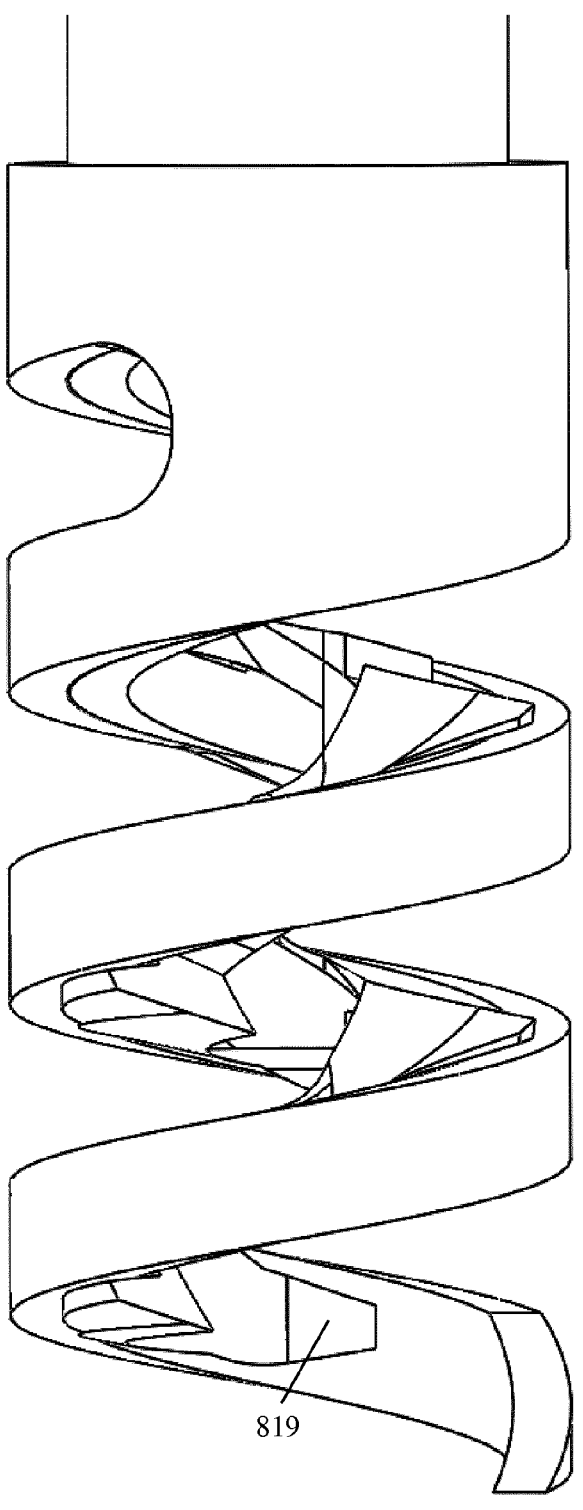
FIG. 93 is another view of the driver coil and implant illustrating particularly a feathered distal end of the implant.
Figures 94, 95:
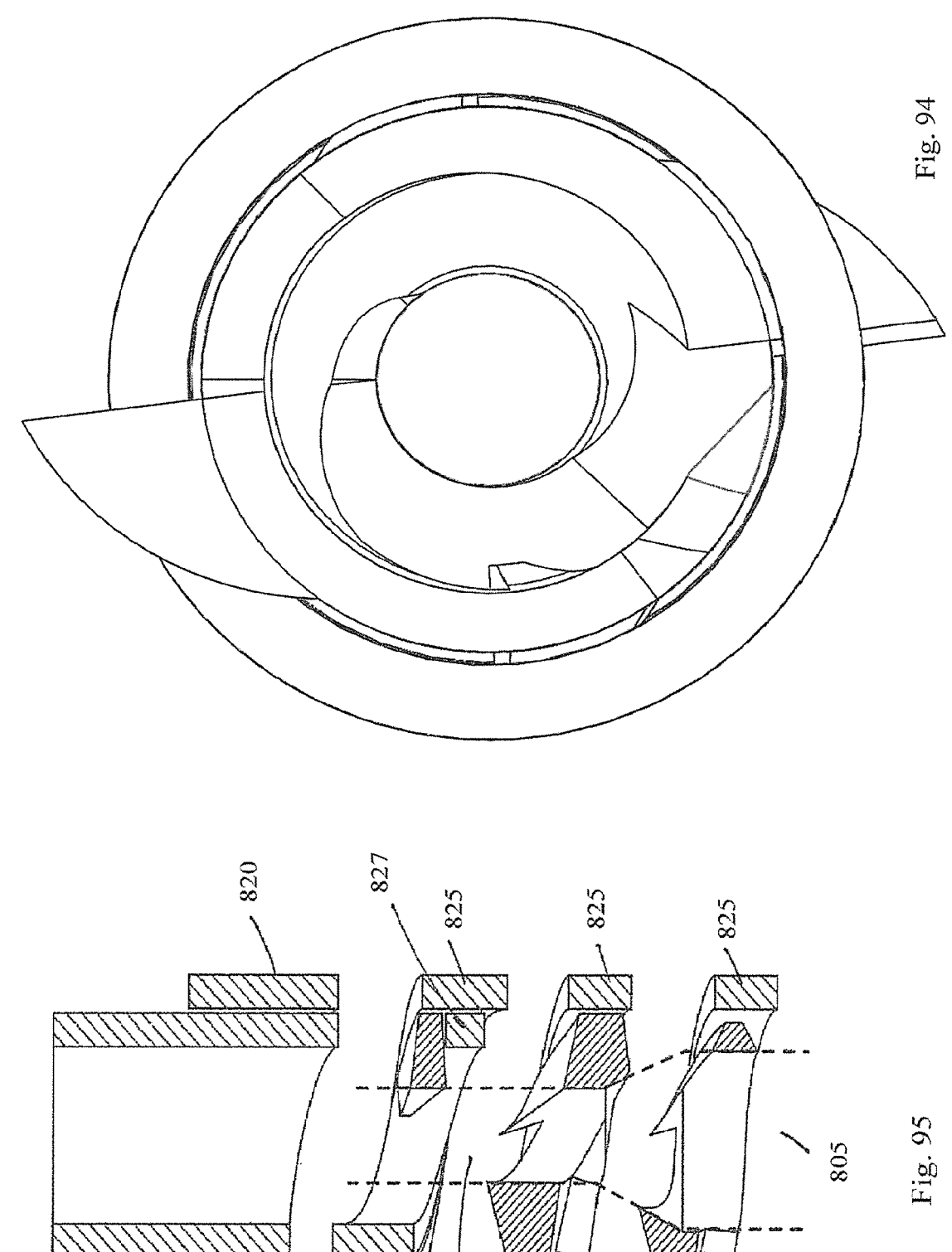
FIG. 94 is a plan view of the implant mounted in the driver coil.
FIG. 95 is a longitudinal cross sectional view of the driver coil and implant of FIG. 88.
Figure 96:
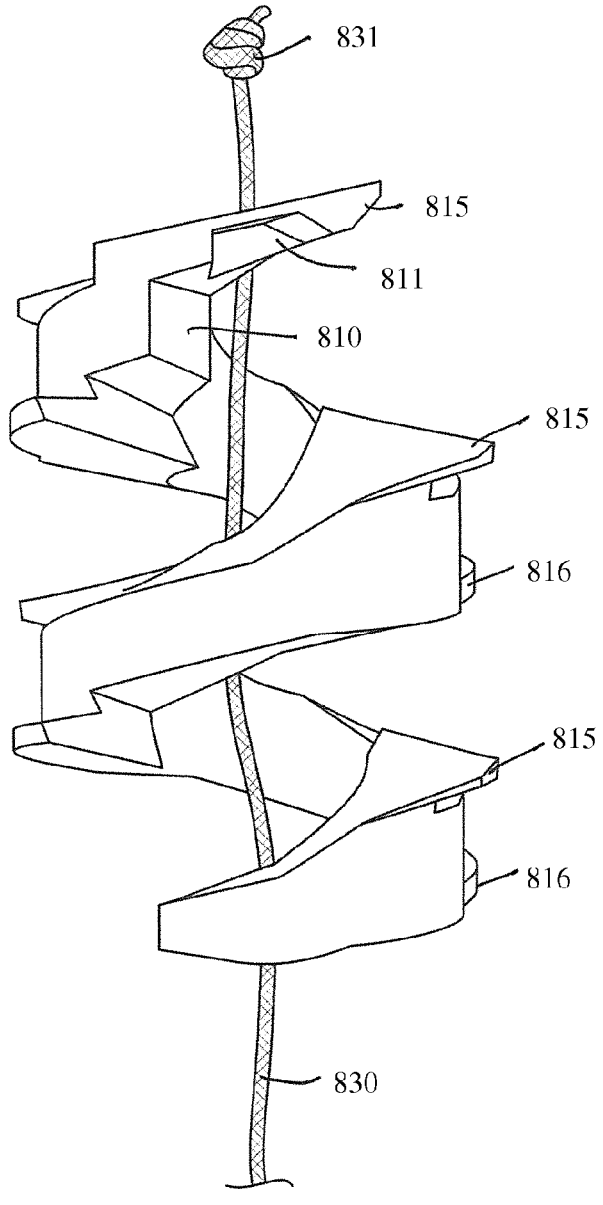
FIG. 96 shows the implant and an associated drain passing though it.

In some embodiments the distal end of the implant is shaped so as to lead to a feathered edge. One such feathered edge 819 is illustrated in FIG. 93. The feathered edge 819 tapers distally to join flush with the internal diameter of the driver coil. This feature facilitates the distal section of the driver coil primarily gathering tissue and leading the tissue into the compression zone of the internal taper of the implant during delivery.

The delivery coil 820 may consist of a number of distal coil loops which are of appropriate dimensions to interface to the implant track. The delivery or driver may comprise a further coil, or plurality of coils proximal to the implant and/or proximal to the shoulder 827, to allow for controlled depth of delivery of the implant into tissue. This additional coil may be of differing cross sectional area, or shape, to the implant engagement coil.

The delivery coil 820 may be attached to a delivery tube. The delivery coil may also formed by a cut (e.g. laser cut) in a delivery tube. The delivery tube is preferentially a hollow tube. It may also be formed form a solid rod in alternative embodiments.

The driver coil tip 821 may be so shaped as to advantageously penetrate the tissue during delivery. The tip 821 may be angled down towards the tissue surface to facilitate piercing, radially outwards to facilitate gathering of tissue for compression and/or to accommodate larger tissue openings, or a combination of both.

The driver coil may have a larger distal diameter than subsequent (more proximal) coils (i.e. tapered coil with larger distal end). A larger diameter allows for gathering of greater bulk of tissue for compression. The larger diameter can also disengage from the implant track due to the straight nature of the outside diameter of the implant.

The internal tapered section of the implant 801 facilitates tissue compression and retention of compression post removal of the driver coil.

The arms 815, 816 on the external diameter of the implant 801 facilitates a track which provides an interface to the driver coil 820. The depth of this track may be undersized to allow for a friction interface keeping the implant in place until delivery.

The cross-section of the distal end of the implant 801 may be 'feathered' or sloped to interface to the driver coil allowing a seamless transition from the driver coil to the implant internal taper during delivery. This geometry reduces the torque required for delivery and prevents tissue fouling on the implant distal edge during delivery. The feathered feature 819 is particularly visible in FIG. 93.

Anti-rewind features, or barbs, may be positioned on the implant externally and/or internally. These features may be beneficial in the disengagement of the driver coil during delivery of the implant into tissue. They also serve to prevent migration of the implant post implantation. Any or all of the arms 815, 816 may be adapted as an anti-rewind feature.

The driver coil 820 and implant engagement track provided by arms 815, 816 may have differing pitch to create a varying 'shelf' feature along the length of the implant. This varying geometry may be beneficial for stabilising (locking) the implant within the driver coil. Additionally this varying feature may be beneficial in providing a stronger surface for the implant/driver coil interaction during dynamic delivery or disengagement and retraction.

In a similar manner the driver coil pitch and implant track pitch may be offset either proximally or distally to allow for a corresponding thicker 'shelf' surface.

There may be anti-rewind features such as barbs on the inner surface of the implant.

Figure 87:
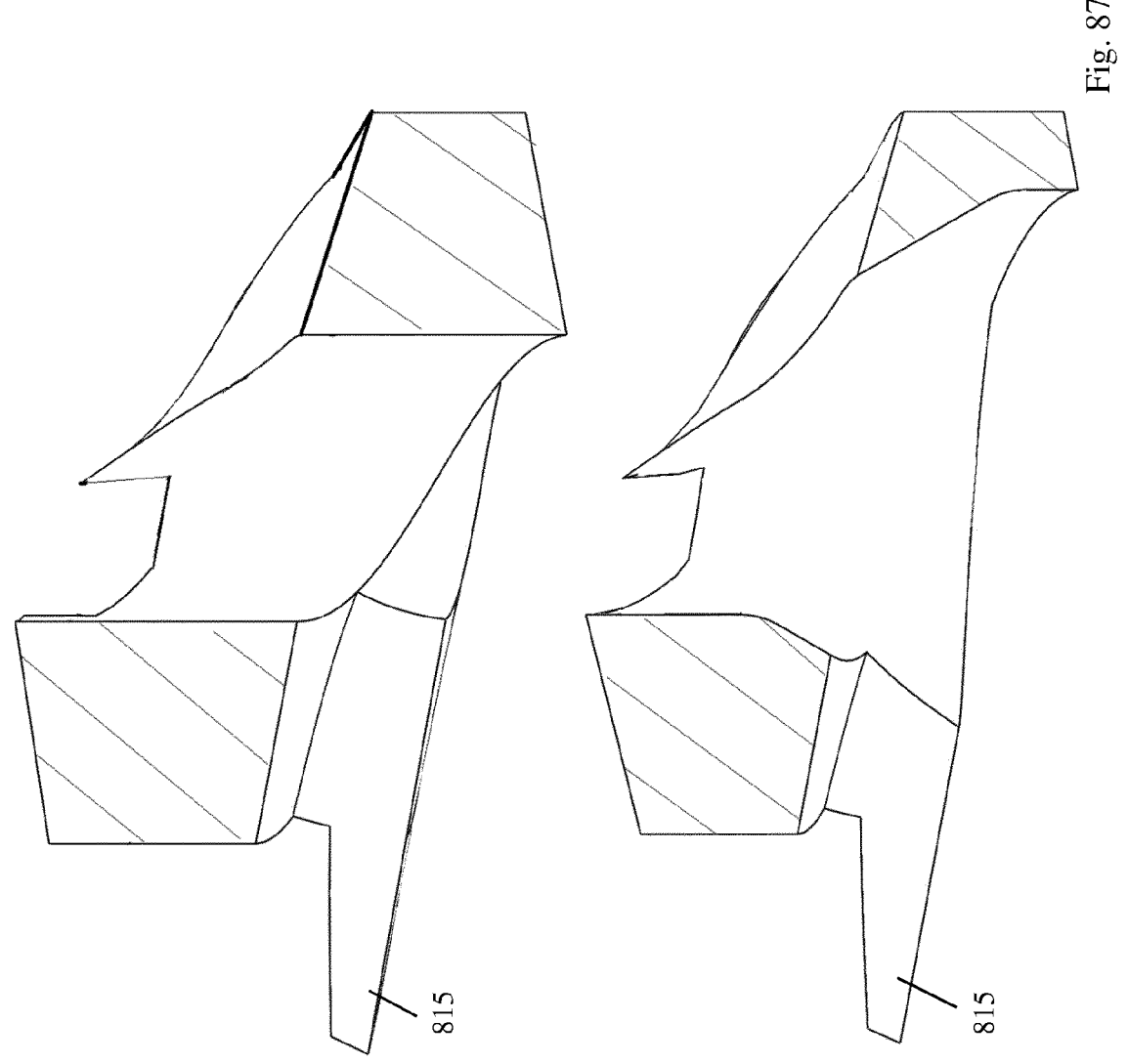
FIG. 87 is an enlarged cross sectional view of portion of an implant illustrating external barbs.
Figure 88:
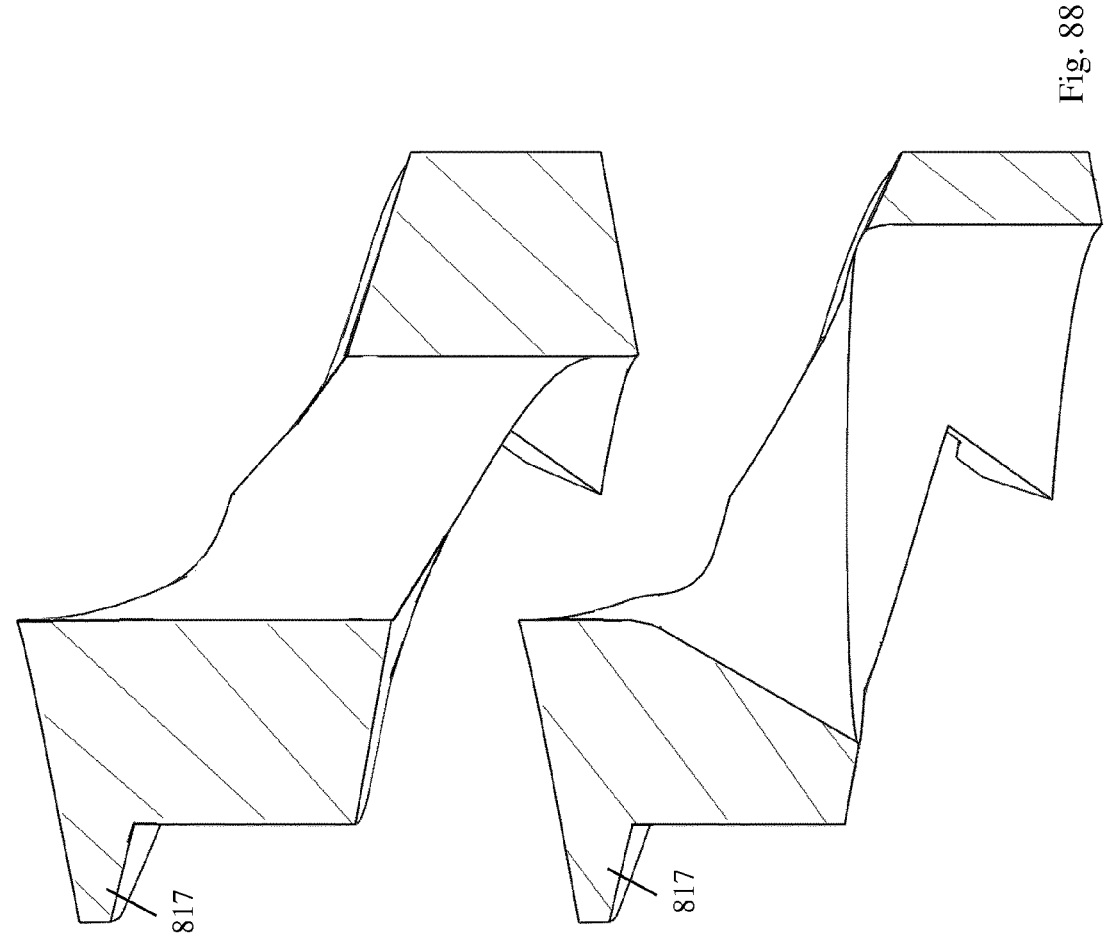
FIG. 88 is an enlarged cross sectional view of portion of an implant illustrating internal barbs.

Referring in particular for example to FIGS. 87 and 88 the implant may have anti-rewind features which in this case are in the form of barbs. In this case the implant has both internal barbs and external barbs. The features or arms 815, may be described as external barbs. Features 817 may be described as internal barbs. In some cases the implant has a plurality (such as four) external barbs and a plurality (such as four) internal barbs.

The internal barbs may be configured to be positioned proximal to the succeeding coils of the driver coil preventing proximal movement of the implant relative to the driver coil. The external barbs may be configured to be positioned distal to the succeeding coils of the driver coil preventing distal movement of the implant relative to the driver coil. The external barbs have the added function of extending radially past the driver coil enabling engagement in tissue during CCW rotation. Both the internal and external barbs are shaped to have a leading edge that allows CW rotation into tissue and presents a flat surface creating anti-rewind force on CCW rotation.

One configuration of internal and external barbs are illustrated in the implant cross sectional views.

FIG. 87 is a cross sectional view that particularly illustrates the external barbs 815.

FIG. 88 is a cross sectional view that particularly illustrates the internal barbs 817.

An interlocking feature may be provided to secure the implant to the driver mechanism until delivery at the appropriate location.

The lock feature may consist of any of the following:

Negative feature on implant surface and corresponding mating positive feature on driver coil Negative feature on driver coil and corresponding mating positive feature on implant surface Alternative embodiments that allow frictional disengagement of the driver coil and the implant after delivery to the appropriate location in tissue Alternative embodiments that allow active disengagement of the driver coil and the implant after delivery to the appropriate location in tissue.

A stabiliser system may comprise a series of needles which may be placed radially around the outside (or inside or inside and outside) of the distal end of a delivery over tube (member). The needles penetrate through the mucosa and a depth into the underlying tissue to stabilize these tissues during the delivery of the implant.

The needles may be stored during device placement and upon localization deployed from their resting place in the distal overtube (crown/rook).

After implantation is complete the needles maybe retracted.

Retractable needles are not necessary but will provide safety from accidental needle sticks to the patient and surgeon, prevent needle damage, and facilitate a lower device profile to ease insertion to the target surgical site. There may be a plurality of needles. There may be a surface stabilisation mechanism used in conjunction with the needles to prevent the movement or binding of the proximal layer of tissue (e.g. mucosal layer in the case of perianal fistula) during implant delivery.

The driver coil may be driven by manual, automatic, powered (e.g. spring loaded, trigger or wheel activated, electrical, pneumatic or other) means. In one embodiment the driver coil is driven by a manual linear actuation, e.g. trigger pull or similar, which is translated to rotational motion via an elongated pitch threaded shaft. In addition the manually operated linear motion may be translated to both rotational and linear forward motion of the driver coil via a worm thread gearbox element or similar.

Preferentially the driver coil is driven a number of turns clockwise to deliver the implant to the appropriate depth in the tissue location and is subsequently reversed in an anti-clockwise direction to disengage from the implant and be removed from the tissue.

In addition to treatment of perianal fistulas the methods and devices of the invention may be used in the treatment of a range of conditions including:

Rectovaginal fistulas

Enterocutaneous fistulas

Enteroenteral fistula

Gastric fistula

Muscle, integument, fascia or other tissue defects

Pilonidal or other sinus

Bodily vessel

Fluid lumen

Repair of anatomical defects or damage

The device is capable of one or more of the following:

accommodating varied fistula tract physiology;

occluding and sealing the internal opening of the tract;

preventing faecal matter re-infecting the tract;

preserving sphincteric function;

enhancing fistula tract healing; and facilitating drainage during healing.

Figure 97:
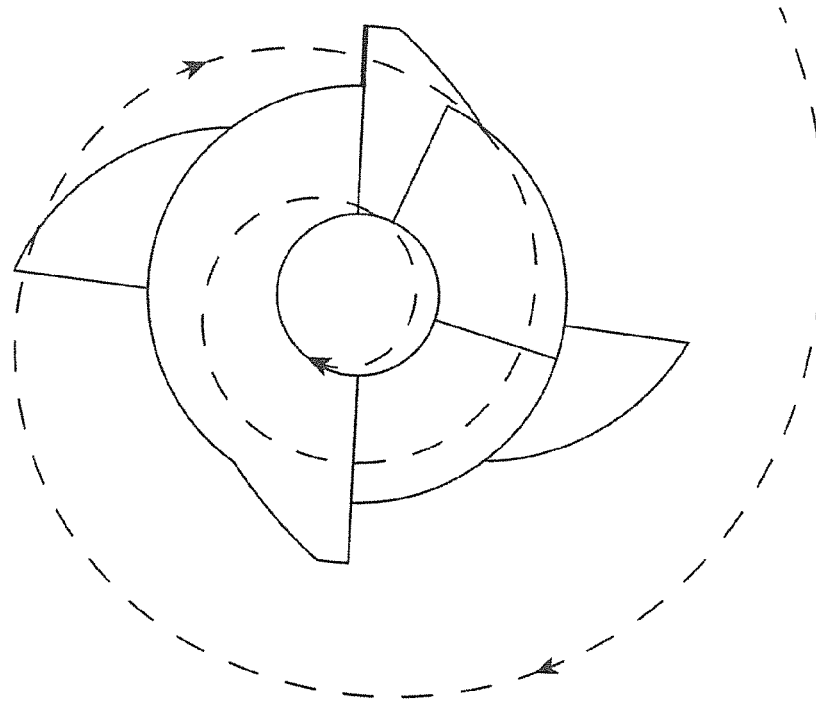
FIGS. 97 and 98 are end views showing the implant in use closing a tissue opening.
Figure 98:
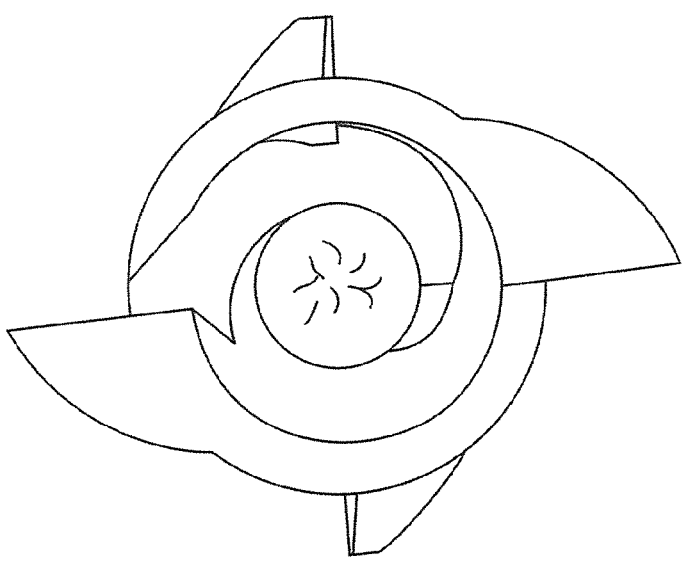
Figure 99A:
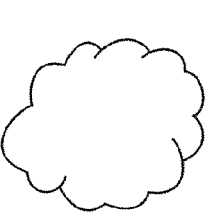
FIGS. 99(a) to 99(e) illustrate the closure of a tissue opening using the implant of the invention.
Figure 99B:
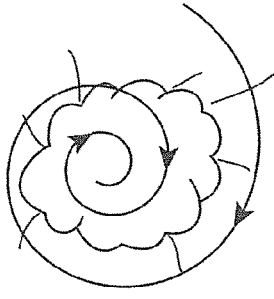
Figure 99C:
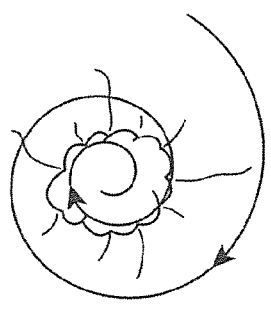
Figure 99D:
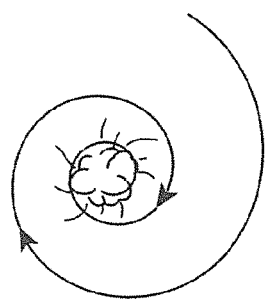
Figure 99E:
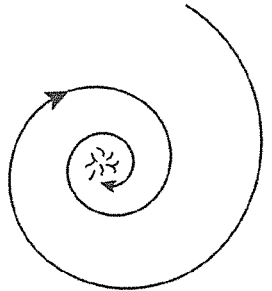
Figure 100A:
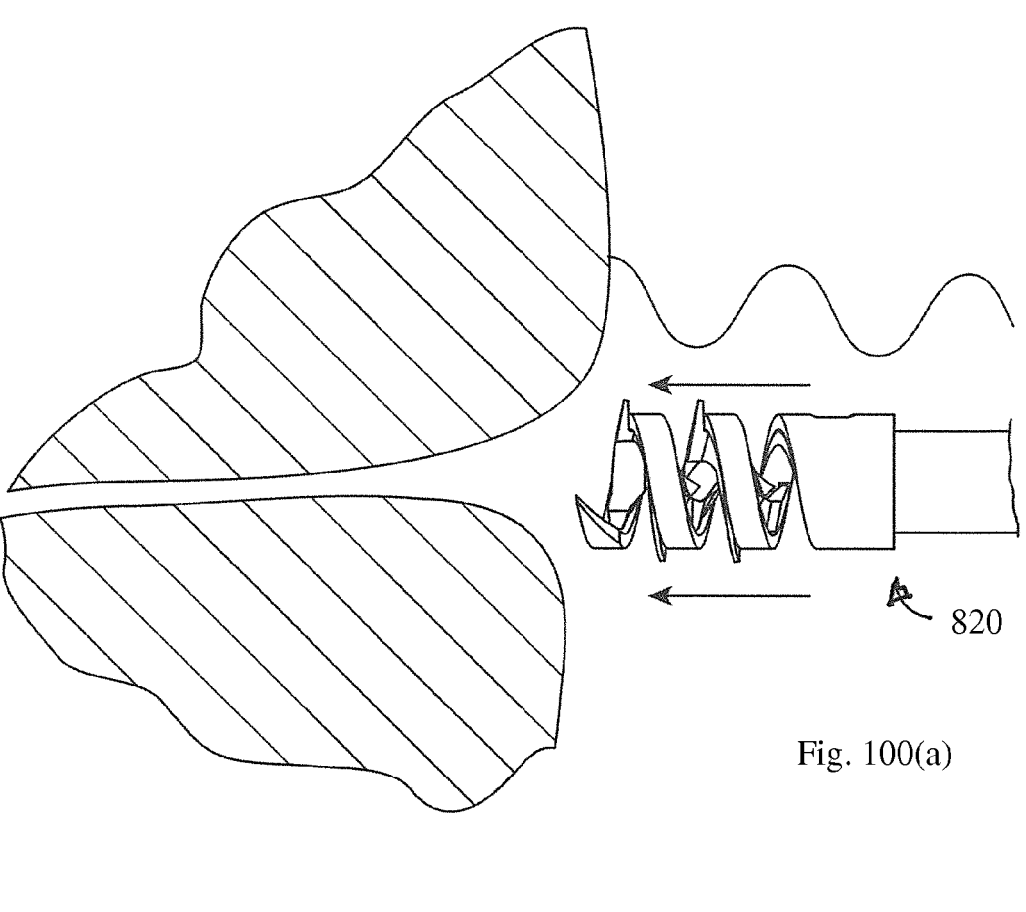
FIGS. 100(a) to 100(d) are partial cross sectional views illustrating the closure of a perianal fistula using the delivery coil and implant of the invention.
Figure 100B:
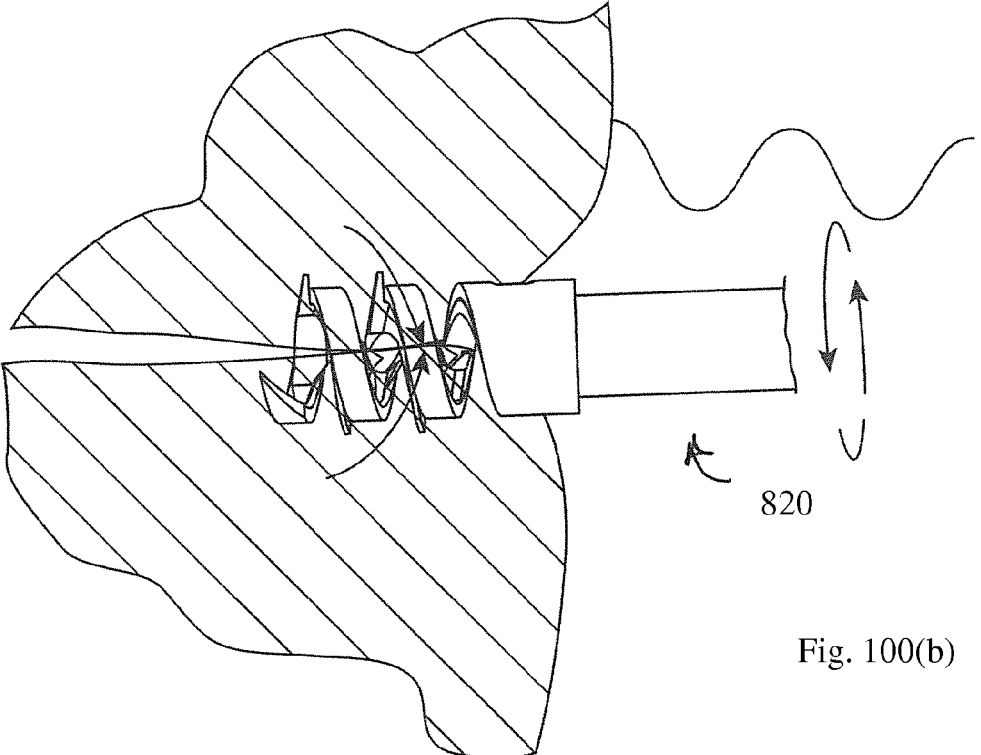
Figures 100C, 100D:
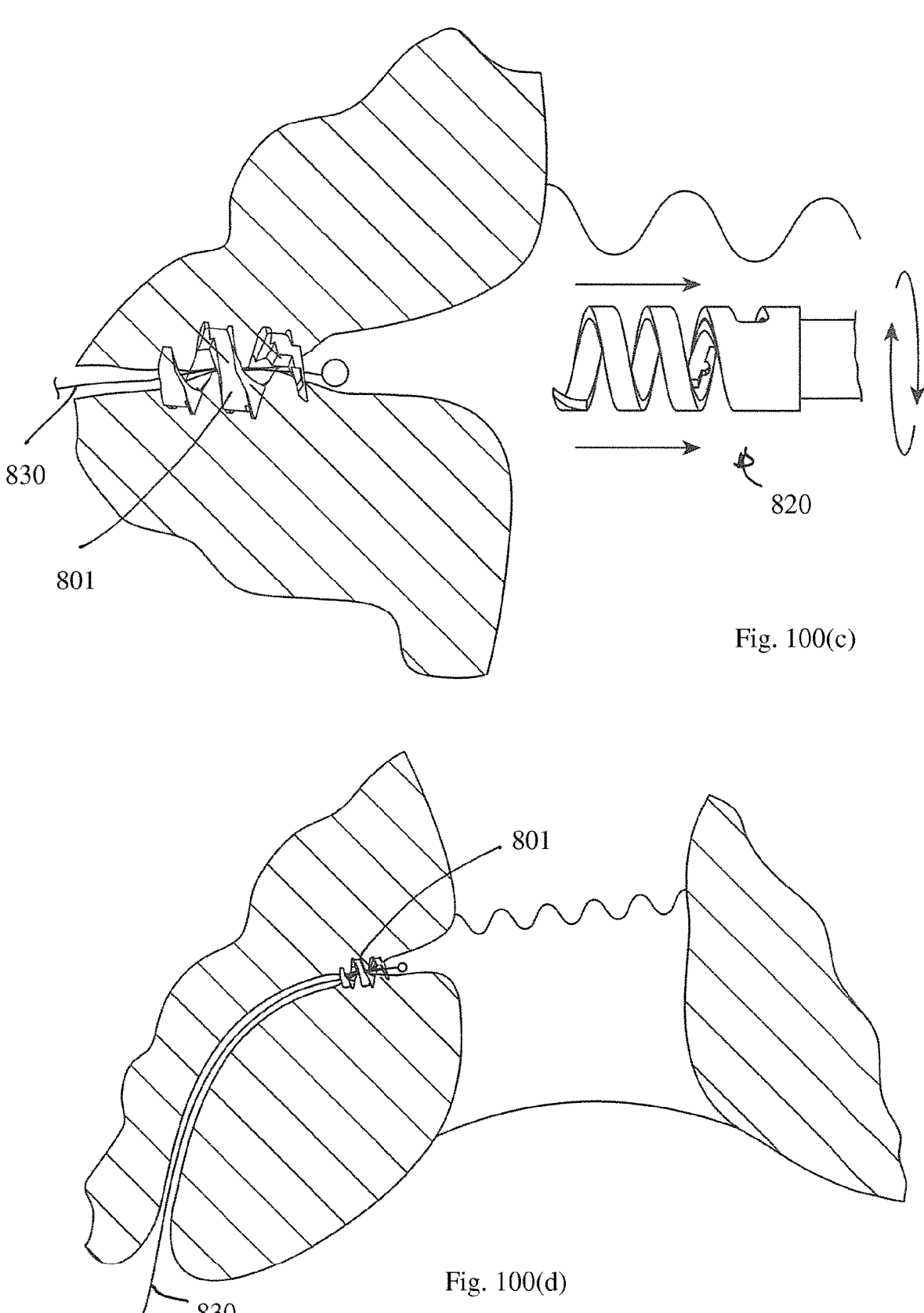
Figure 101:
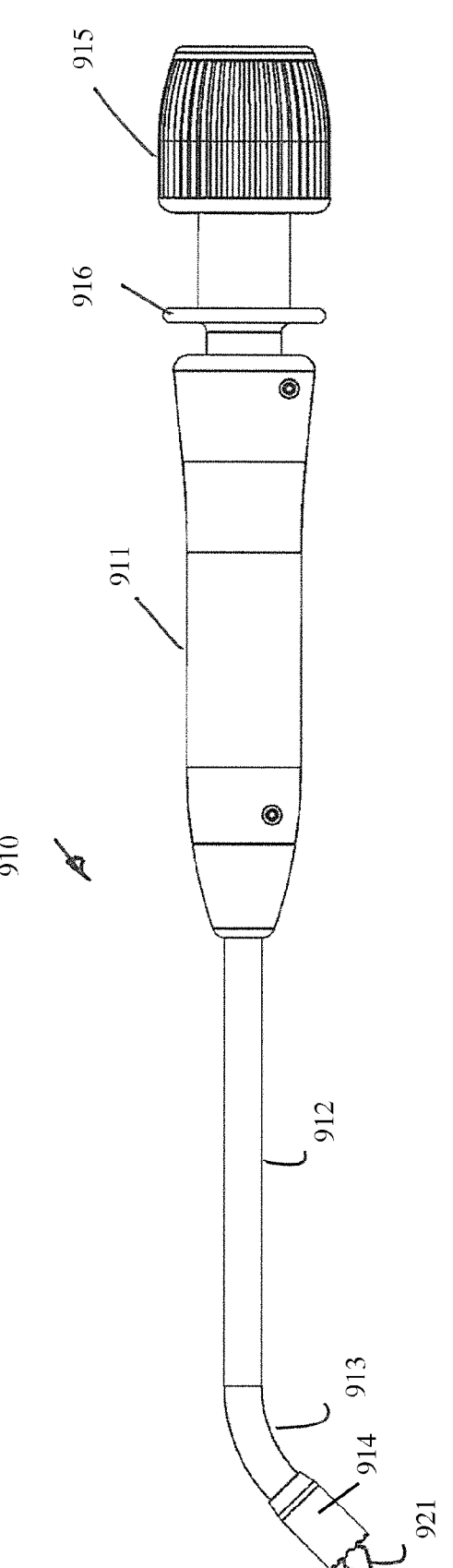
FIG. 101 is an elevational view of a delivery device of the invention.
Figure 102:
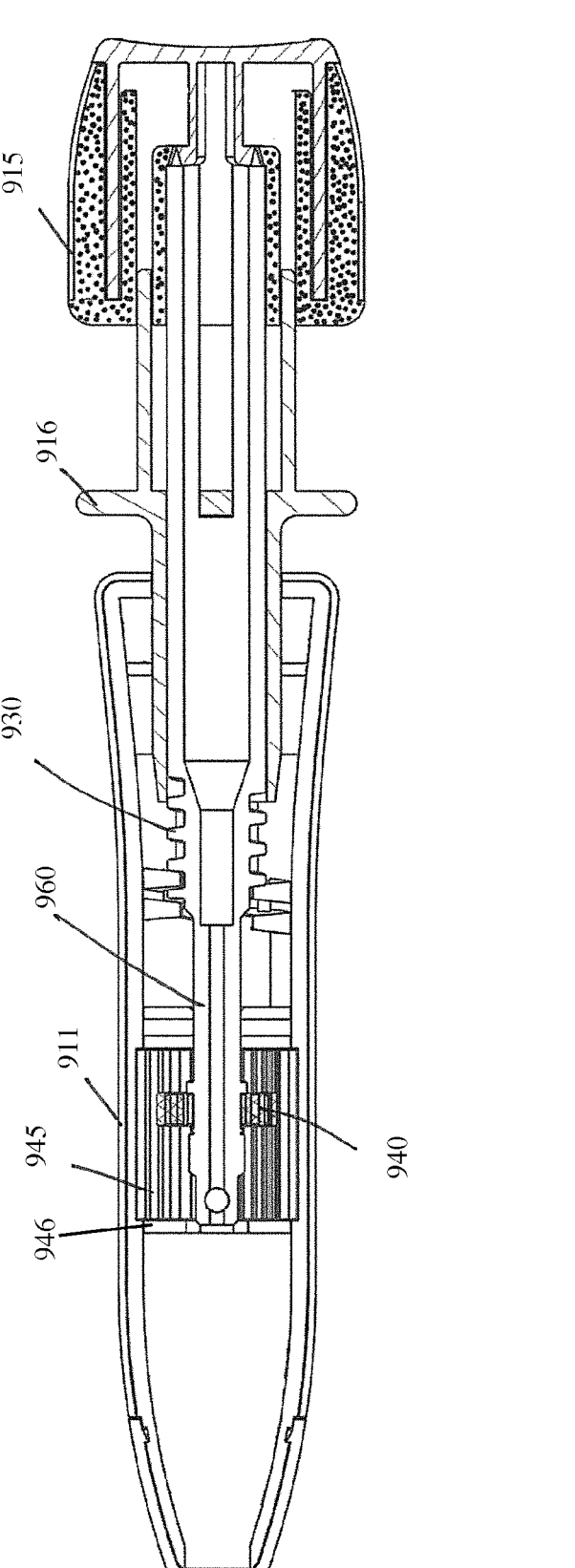
FIG. 102 is a cross sectional view of a handle end of the delivery device.

Referring for example to FIGS. 97, 98, 99(*a*) to 99(*e*) and 100(*a*) to 100(*d*) the driver mechanism delivers the coil through the mucosal lining of the rectum via rotatory or other means for the example of a perianal fistula.

The distal tip of the driver punctures through the mucosal lining surface and engages initially with the internal sphincter muscle surrounding the internal opening of the fistula tract resulting in initial gathering and compression of tissue.

The implant coil is completely delivered through and past the mucosal surface and into the sphincter complex consisting of the internal and external sphincter muscles. The delivery mechanism interface located distally on the delivery mechanism member detaches from the tapered coil and the delivery mechanism is removed from the surgical field.

The mechanism of action of the delivery of the tapered coil results in sphincter muscle complex tissue being drawn into the centre of the coil construct.

The complete delivery of the coil results in closure of the internal opening of the fistula tract by gathering of and compression of sphincter muscle tissue. This mechanism as described allows both the sphincter muscle tissue to knit together, and the mucosal surface to remodel to cover the site of delivery over a period of time, eventually resulting in complete resolution of the sphincter muscle defect associated with the internal opening of the fistula tract.

Alternatively a mucosal slit may be employed to access the sphincter muscle directly and the implant may be delivered as previously described.

The implant comprises a shaft with a substantially uniform outer diameter and a tapered inner diameter. The leading end of the implant is the largest coil and initially surrounds the tissue defect with appropriate margin. As the implant is advanced the leading end provides a large surface area to effectively anchor the implant. Each subsequent coil provides (adds to) the anchoring and compression function. The smallest coil towards the trailing end provides the highest amount of tissue compression. As the implant is turned into the tissue each coil further compresses the captured tissue toward the center of the tissue defect, thus effectively completely compressing the surrounding tissue inwardly. The close approximation of tissue allows for the tissue to heal together. This compression provides an effective seal against the pressures generated in the rectum and prevents entering of passing faeces into the fistula tract thus preventing re-infection. The smaller diameters of the implant coils retain the captured tissue from separating and prevents the breakdown of the healing process or foreign material from entering the tissue defect. This is a major advantage over sutures and suture based surgical techniques such as the advancement flap (dermal flap) and the LIFT procedures.

The compression ensures close approximation of tissue throughout the center of the implant. At the most proximal surface the close approximation of tissue provides support to the healing mucosal lining of the rectum over the implant and tissue defect. Thus the healing tissue is fully supported by the implant during the healing process and is capable of surviving pressures of 150 mmHg and upwards, such as up to 200 mmHg or greater which can be generated in the rectum.

The implant may be used in association with a drain or seton 830 which is illustrated in FIG. 91.

It will be appreciated that the implant device with or without an attached drain (or seton), may be used to close fistula openings that may commonly occur in other areas of the body, such as: biliary (created during gallbladder surgery, connecting bile ducts to the surface of the skin), cervical (either an abnormal opening into the cervix or in the neck), craniosinus (between the space inside the skull and a nasal sinus), enterovaginal (between the bowel and vagina), faecal or anal (the faeces is discharged through an opening other than the anus), gastric (from the stomach to the surface of the skin), metroperitoneal (between the uterus and peritoneal cavity), umbilical (between the navel and gut). These fistulas may be:—blind also known as a sinus (open on one end only, but connects to two structures); complete (has both external and internal openings); horseshoe (connecting the anus to the surface of the skin after going around the rectum); or incomplete (a tube from the skin that is closed on the inside and does not connect to any internal structure).

It will be appreciated that the tapered coil may be of any suitable shape in transverse cross section. For example, the coil may be round, oval, triangular, multifaced or ribbon-like. In some cases the coil may be hollow.

The coil may be intended for subsequent removal or may be bioabsorbable.

Typical materials for the coil include

Bioabsorbable magnesium (including MgFe and other magnesium alloys) would be a material of choice because it offers the strength of stainless steel and similar metals, yet is bioabsorbable. MgFe alloys are well studied and have been used in medical products.

PLA) and PLGA (poly(lactic-co-glycolic acid)) are bioabsorbable polymers and would be a material of choice as they are commonly used bioabsorbable materials and have been well studied and used in medical products for over 70 years.

The coil may also be constructed from other common materials used for suture applications.

A bioabsorbable tapered coil would be beneficial to treatment of perianal fistulas due to the body's natural tendency to reject foreign materials.

The drain (or seton) may be used as a guidance and positioning mechanism and once the device is implanted serves as a means of fistula tract drainage. The drain may be constructed of bioabsorbable materials, tissue healing enchantment properties, infection control agents and be constructed of part or composite of these materials.

After the fistula tract preparation, the drain is attached using standard surgical technique to the existing surgical probe, suture, or drain already in place in the fistula tract. Once the drain is attached, the system is pulled through the fistula tract proximally (towards the physician) until the coil device is adjacent to the tissue wall (rectal wall). The drain ensures that the outer leading coil is centred around the outside of the fistula tract. Tension may be applied to the drain as the coil is advanced into the tissue to aid in advancement and to maintain a centred position around the fistula tract.

The drain (or seton) is attached to the central portion of the coil. With the coil knitting together the sphincteric muscle and closing the fistula tract's internal opening the drain maintains the proximal portion of the fistula tract's patency to facilitate drainage of any abscess, pus, and new accumulation of bodily fluids to prevent infection occurrence. The drain (or seton) prevents the tract from closing in on itself proximal of any fluid accumulation and acts as a conduit allowing material drainage between the wall of the tract and the outer wall of the drain. The drain (or seton) may also have a central lumen with tangential drainage holes entering from the external wall of the drain. The drain (or seton) may be constructed with a multi surface external wall to create channels and optimize the fluid drainage and prevent the fistula tract wall from occluding drainage around the drain (or seton).

The drain (or seton) is constructed of materials that are strong enough to allow for surgical placement in the fistula tract. The drain may be constructed of materials that are non-absorbable and meant to be removed at a later time. Alternatively, the drain may be made of materials that bioabsorb throughout and upon completion of the fistula tract healing processes (examples include magnesium, PLA, PLGA). The drain may be constructed of or include anti-infection agents to prevent infection of the fistula tract (silver ions, antibacterial agents). The drain may be constructed of materials that aid in tissue growth (stem cell, collagen matrix). The drain may be constructed of part or all elements as described.

The drain (or seton) may be of any suitable shape in cross section such as round, oval, cross shape, star or braid. In all cases the drain may be hollow to further enhance drainage. The drain may have peripheral holes to provide for increased drainage effectivity. The holes allow additional surfaces of drainage, by increasing drainage surface area/channels the fluid drains more quickly and reduces the chance that any of the channels will become occluded and prevent fluid drainage at the same moment in time.

As noted above, one or other or both of the coil and drain (or seton) may comprise bioabsorbable materials.

Typical materials for the coil include:

Bioabsorbable magnesium (including MgFe and other magnesium alloys) is one material of choice because it offers the strength of stainless steel and similar metals, yet is bioabsorbable. MgFe alloys are well studied and have been used in medical products.

Synthetic bioabsorbable materials may include PLA and PLGA (poly(lactic-co-glycolic acid)) (PLGA, PCL, Poly-orthoesters, Poly(dioxanone), Poly(anhydrides), Poly(trim-ethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials and have been well studied and used in medical products for over 70 years.

For example, companies such as Ethicon market a number of such products with different absorption rates such as http://www.ethicon.com/healthcare-professionals/products/. Absorbable polymer materials are also available from medical material companies such as Zeus, see http://www.zeus-inc.com/advanced-products/absorv-bioabsorbables.

Typical materials for the drain (or seton) include:

Bioabsorbable magnesium (including MgFe and other magnesium alloys) is one material of choice because it offers the strength of stainless steel and similar metals, yet is bioabsorbable. MgFe alloys are well studied and have been used in medical products.

Synthetic bioabsorbable materials may include PLA and PLGA (poly(lactic-co-glycolic acid)) (PLGA, PCL, Polyorthoesters, Poly(dioxanone), Poly(anhydrides), Poly(trimethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials and have been well studied and used in medical products for over 70 years.

In one case both the coil and the drain (or seton) are bioabsorbable, and the drain degrades prior to the degradation of the coil. This may be achieved in a number of different ways, such as the drain being of a different bioabsorbable material to the coil.

For example, the coil implant may be constructed of PLLA which degrades slowly, typically within 18 to 36 months depending on formulation, cross section, and surface modifications, and the drain may be constructed of PLGA (85L/15G) which typically degrades "faster" in 1 to 2 months depending on formulation, cross section, and surface modifications.

Another method of altering the time of degradation (degradation (absorption) properties) is by providing a reduced cross sectional area, more porosity, less crystallinity, more reactive hydrolytic groups in the backbone, more hydrophilic end groups, and/or more hydrophilic backbone.

In one case, the drain (or seton) substantially maintains its structure for five weeks post-surgical implantation. This is variable depending upon the healing time of the patient, with full healing usually occurring within a 5 to 10 week period. By way of example, the coil implant may remain for a period of at least 10 weeks after healing and may degrade over a 6 to 18 month time period from the date of implantation.

Advantageously, the closure mechanism of the device is maintained during the entire healing process. In some cases the coil remains in situ to withstand rectal pressures and maintain closure of internal tract opening for at least 10 weeks to prevent re-opening of the tract.

The coil implant may remain in place longer to allow full healing of the internal opening of the fistula tract. The drain may degrade at a faster rate compared to the coil implant so long as the drain is in place for a long enough time for all remaining abscess and infection, to drain from the fistula tract and any side branches. It is advantageous that the drain absorbs faster than the coil so that the patient does not have any visually remnant feature of the device or thoughts of fistula. The drain is not needed for as long a period as the coil implant, with the drain absorbing faster than the implant, the patient will not have to return to the surgeon for removal during the internal opening healing process.

Also, the implant remains in place for a long enough period of time (e.g. greater than 1 week) to allow remodelling of the defect in the mucosa and formation of a mucosal layer. This mucosal layer acts as a bacterial seal preventing reinfection of the tract from entering of fasces. The re-formation of the musical layer in conjunction with the sphincter muscle closure mechanism prevents fasces entering the tract.

The implant coil and draining drain (or seton) may be doped or loaded with healing and antimicrobial agents (such as stem cell, silver ions, silver particles, antibiotics, antibacterial agents and the like).

The drain (or seton) may be of differential bioabsorption wherein the drain is absorbed at a different rate along its length.

The drain (or seton) may be of differential bioabsorption wherein the distal portion of the drain absorbs more quickly than the proximal portion. This differential absorption of the drain results in the drain remaining attached to the coil via the proximate portion until fully absorbed. Advantageously, this allows for the external opening to close and remove the chance of the drain being pulled out through the external opening.

The drain (or seton) may also be of differential bioabsorption wherein the proximal portion of the drain absorbs more quickly—in this case the anchoring mechanism of the closure device with relation to the drain could be broken at an earlier time than the full drain absorption allowing the drain to be removed (by the patient or doctor or naturally fall out) through the external opening.

In both differential absorption embodiments, the entire drain (or seton) would have to remain in place for sufficient drainage during the healing time of the tract (e.g. 2 to 10 weeks).

The bioabsorbable materials used in the construction of the implant coil, or drainage drain (or seton), or both, can be both natural or synthetic polymers such as those listed below.

Natural Polymers
    Fibrin
    Collagen
    Chitosan
    Gelatin
    Hyaluronan
Synthetic Polymers
    PLA, PGA, PLGA, PCL, Polyorthoesters
    Poly(dioxanone)
    Poly(anhydrides)
    Poly(trimethylene carbonate)
    Polyphosphazenes The selection of the material used can be made whilst taking the following factors into account.

Factors that accelerate polymer degradation:
    More hydrophilic backbone
    More hydrophilic end groups
    More reactive hydrolytic groups in the backbone
    Less crystallinity
    More porosity
    Smaller device size The delivery system has the following advantages:
    Ability to follow the tract of the implant coil allowing deep delivery to the sphincter muscle complex allowing for greater anchoring and sphincter muscle apposition at the muscle defect
    Ability to disengage and retract in a spiral nature, reversing through the same tract as delivery preventing further damage to the tissue
    Prevents the mucosa of the rectum being pulled down towards the sphincter muscle complex
    Enables the implant to be delivered through and past the anoderm resulting in lower pain due to interference with the nerve endings of the anoderm
    Prevention of bacterial tracking by delivering deep sub mucosally.

These delivery mechanisms may be coupled to a manually operated, trigger operated user interface or similar.

In current techniques for treating a fistula a surgeon identifies the external opening of the fistula tract and carefully inserts a probe through the external opening, through the fistula tract and through the internal opening of the fistula. The probe is then extended back through the rectum and a localisation drain (or seton) or suture is attached to the end of the probe which is then drawn back through the rectum and the fistula tract until it exits through the external opening of the fistula tract. The localisation drain (or seton) loop is then tied off.

The implant and delivery system of the invention is compatible with this known current technique. In the invention the probe or the localisation drain may be used to guide the leading end of the implant coil and/or the drainage drain.

The implant body in some cases is in the form of an "open" tapered coil body in which the distal edge (leading edge, into the muscle) is of a larger diameter than the proximal edge (trailing edge, rectum surface), the proximal portion is of smaller diameter than the distal portion. The coil is of open form, therefore there is no inward protrusion at either the proximal nor distal end of the body. The open form factor enables the implant to be driven into the tissue body to a pre-determined depth (depending on the taper which results in progressive tissue compression).

The open coil design allows for the mucosal layer to heal over the top of the implant, and the implant supports the healing of the mucosal layer, by preventing the pressure from opening the tract, and compromise freshly healed mucosa layer. With the implant below the mucosa it does not interfere with external rectal surface and interact with faeces that may drag the implant out of its purchase or lend to tract infection along its body. Thus, the implant is suitable for submucosal delivery which facilitates the formation of a continuous mucosal surface over the site of implantation.

The implant in some cases has anti-movement (anti-rewind) features to prevent the rotational movement of the implant in the counter-clockwise motion. Typically, the implant is driven into the tissue body in a clockwise motion consistent with the usual direction of driving fixation medical devices. However, it will be appreciated that the implant may also be driven into the tissue in the counter clock-wise direction. The anti-rewind features facilitate the forward driving motion into the tissue body in a clock-wise motion to be effortless during delivery but provide resistance to prevent the implant from working itself out or unwinding during the course of natural wound healing and normal physiological forces experienced day to day of the patient's life.

The anti-rewind features may include one or more of:

Positive feature such as a barb, fishhook, arrowhead or the like. Such positive barb type features may be added in the X, Y, or Z plane to enhance the fixation of the implant;

Negative features such as trough features along the body of the implant, such trough features may be one or more of a square trough, a lead in trough, and/or a square back trough;

V-Lock type, quills may be incorporated along the body of the implant. The quills may be shaped to facilitate ease of entry into tissue but does not allow the implant to move in the opposite direction. The quill may lay fat upon insertion and then become exposed if moved in the opposite direction. A multiple of such quills increases the surface area (friction) of the implant body and prevents the implant from re-winding;

Surface modification/surface area enhancing. The surface of the implant body may be modified to increase the surface area to increase the friction interaction between the implant and the tissue it is implanted in.

Surface roughening mechanical:

May include sandblasting, micro stamping (impression on material)

Surface treatment chemical:

May include soaking (being exposed to) in a chemical agent that roughens the implant body surface May include chemical photo etching Surface treatment in manufacturing process:

The tooling of a moulded implant design may have positive features that when the implant is removed from the mould, rough features are left on the body of the implant Surface "pillar" like gecko feet (*Setae*) Biomimicry The driver coil surface may be constructed so as to have a lubricious nature (e.g. by means of a coating or surface treatment or other) in order to minimise the torque requirement associated with the tissue friction during delivery of the implant coil and during retraction of the delivery coil.

The coiled section of the delivery coil may include features to temporarily lock or fasten to the implant prior to and during implant delivery. This provides a positive interface between the implant and the delivery mechanism, to prevent premature implant detachment and related delivery issues.

When the implant has been delivered to the correct location and depth the delivery mechanism detaches/disengages from the implant and is removed from the anatomy.

The driver coil may have an interface to the implant which allows positive (interlocking) when the driver coil is turned in a clockwise direction and negative (i.e. disengagement) interaction when the driver coil is turned in an anti-clockwise direction (or vice versa). Thus when the implant has been delivered to the tissue by means of a clockwise driver coil motion, the driver coil may then turn in an anti-clockwise direction, disengage from the implant, and exit (or 'back out') from the tissue.

The implant may be attached to the delivery coil by a mechanism that prevents the implant becoming dislodged from the delivery coil prior to complete delivery. Thus, the implant coil is prevented from prematurely detaching from delivery coil.

The internal support structure of the implant coil may have a positive feature (peak) that locks into a negative (valley) feature on the implant. There may be several features of this type to enhance the locking grip.

The inverse of this arrangement may also be implemented in which a positive feature is provided on the implant and a negative feature is a part of the driving mechanism.

Alternatively or additionally, the implant may be attached to the internal opening of the implant driver by friction/interference fit/surface roughness. The driver col may be hollow and accept a solid implant or the driver may be solid and inserted into the hollow portion of the implant.

The cross section of the driver coil may be a channel or slot rather than closed circular. A coil with such a cross section may be more easily manufacturable. It may also allow the incorporation of internal (to the driver coil) locking features to interface with the implant.

The implant is interfaced to the driving mechanism such as a driver coil. In one case the interface comprises a flare or step or shoulder that abuts against the driving mechanism. Such a flare provides the push point of the implant and transfer of force to drive the implant into the tissue body.

The flare may also act as a barb or anti-rewind feature allowing only one way (e.g. clockwise) motion which in one case is forward motion (clockwise motion driven into the tissue body) and prevents the implant from moving in a backwards motion (unwinding/counter clockwise).

Such a barb feature may be achieved by having the flare surface area greater than the driving coil interface surface area.

The flare may be positioned anywhere along the implant body that is optimal for the implant driving force, driver attachment coupling, and/or anti motion control (anti-rewind can be clockwise or anti clockwise).

It will be appreciated that as an alternative to such locking features on the implant coil similar features may be provided on the engagement surfaces of the delivery coil.

The implant is in some cases in the form of a coiled body structure. The distal end of the implant is the largest coil, and the distal end initially surrounds the tissue defect with appropriate margin. As the implant is advanced the distal portion provides a large surface area to effectively anchor the implant (each subsequent coil provides (adds to) the anchoring and compression function). The smallest proximal coil provides the highest amount of tissue compression. As the implant is turned into the tissue each coil further compresses the captured tissue toward the centre of the tissue defect, thus effectively completely compressing the surrounding tissue inwardly. The close approximation of tissue allows for the tissue to heal together. This compression provides an effective seal against the pressures generated in the rectum and prevents entering of passing faeces into the fistula tract thus preventing re-infection. The smaller diameters of the implant coils retain the captured tissue from separating and prevents the breakdown of the healing process or foreign material from entering the tissue defect. This is the advantage over sutures and suture based surgical techniques such as the advancement flap (dermal flap) and the LIFT procedures.

The compression ensures close approximation of tissue throughout the centre of the implant. At the most proximal surface the close approximation of tissue provides support to the healing mucosal lining of the rectum over the implant and tissue defect. Thus the healing tissue is fully supported by the implant during the healing process and is capable of surviving pressures of 150 mmHg and upwards of 200 mmHg which are generated in the rectum.

Preferably, the coil is delivered submucosal (at a predetermined depth) below the surface of the mucosa. This ensures there is a full mucosal seal at the rectal mucosa surface to provide for a bacterial seal barrier. With the implant just below the surface the tissue is draw inwards for complete compression and supports the mucosa healing process.

As the implant is turned into the tissue the compression becomes greater along the depth of the coil (progressive compression) and the length of the tract captured internal of the implant is compressed completely, the close approximation of tissue aids in the healing process.

The implant and delivery system is compatible with current surgical technique.

Upon completion of the surgeon preparing the tissue tract, the device drain is attached to the rectal end of the fistula probe or drain/suture that was used to localize the tract.

The probe/drain is pulled toward the surgeon through the fistula tract out of the external opening until the large distal portion of the implant is abutted against the rectal wall. The implant coil is aligned to be concentric to the internal tract opening.

The device drain is tied to the fistula probe or localization drain (or seton).

In one embodiment the drain runs distal of the implant and through the length of the handle and may be anchored in the proximal portion of the drive shaft or handle.

At the interface of the implant and driver a cutting mechanism (such as a snip, guillotine or the like) may be provided to automatically cut the drainage drain once the implant is delivered. The handle/delivery system may then be readily removed from the surgical field.

The invention also provides an implant and a driver element such as a coil with a locking feature. The implant and driver may be locked together during insertion until the desired implant depth has been reached.

The locking feature may comprise an element at the proximal end of the implant that is engaged by the driver coil during insertion and released when the implant is delivered. The release may be an automatic release. The implant may be locked to the delivery by a distal cap.

In some embodiments a positive feature or rail is provided on the external of the implant for engagement in a corresponding recess in the delivery element such as a coil. The rail may be of I-shape in cross section.

The rail may comprise a plurality of segments spaced-apart along the implant.

The implant may have laterally projecting features that embrace a driver coil strut therebetween.

The rail feature may be tapered.

The distal tip of the driver element may be shaped for initial engagement with tissue. The driver coil may have a distal slit for engagement with a rail of the implant.

Also provided is an implant with a feature for mounting a drain or seton to the implant.

In some embodiments the implant tapers from an internal diameter of from 1 to 6 mm at a distal end to an internal diameter of from 0.5 to 2 mm at a proximal end.

In some embodiments the pitch of the coil of the implant is from 2 mm to 4 mm.

The implant may comprise a locking feature for locking with a delivery device. The locking feature may be releasable. In some cases the locking feature is releasable automatically. The locking feature may comprise a flexible armature.

In some embodiments the implant comprises an outer rail. The rail may be of I-shape in cross section.

In some cases the rail comprises a plurality of segments.

In some embodiments an outer surface of the rail is not smooth over at least portion of the length thereof.

The implant may be at least partially coated with a hydrophilic coating.

In some cases the inner diameter of the driver coil is from 4 mm to 6 mm.

In some cases the outer diameter of the driver coil is from 6 mm to 8 mm.

The wall thickness of the driver coil may be from 0.5 mm to 1 mm.

In some cases the pitch of the driver coil is from 2 mm to 4 mm.

In some embodiment the driver coil comprises a plurality of coil struts and the height of a strut is from 0.5 mm to 2 mm.

The driver coil in some cases comprises from 2 to 5 turns such as 2.75 turns.

In some cases the driver coil comprises a trough for reception of a rail.

The driver coil may be coated with a lubricious material.

In some embodiments the driver coil comprises a hydrophilic coating.

A distal tip of the driver coil may comprise a plurality of facets to form a sharp tip.

The delivery device in some cases comprises a locking feature for locking with an implant.

The invention also provides a delivery system comprising a delivery device of the invention and a driver shaft for the delivery device.

In some cases the driver shaft and the delivery device are integral.

The driver shaft and the delivery device in some cases are monolithic.

In some embodiments the driver shaft comprises at least one bend.

The driver shaft may be at least partially flexible and/or malleable.

The invention also provides a system comprising an implant of the invention and a delivery device of the invention.

The system as in some cases further comprises a drain.

The implant may comprise a mounting feature for mounting the drain to the implant.

The invention also provides a drain (or seton) such as a drainage drain comprising a plurality of peripheral holes or pores.

The invention also provides a method for treating a defect comprising:— creating a mucosal slit to expose tissue surrounding a defect;

inserting an implant coil into the exposed tissue; and rotating the implant to draw tissue inwardly.

In some cases the defect is a fistula.

In some embodiments the defect is a perianal fistula and the mucosal slit is created to expose the sphincter muscle surface.

The invention further provides a method for treating a defect comprising a tract, the method comprising:— introducing a growth enhancement medium into the tract, inserting an implant into tissue adjacent to the tract, and rotating the implant to draw tissue inwardly to substantially close an opening of the tract.

The tract may comprise a first opening such as an internal opening and a second opening such as an external opening and the method comprises using the implant to close at least one of the first and second openings.

The method may comprise closing the first opening with a first implant.

The method may comprise closing the second opening with a second implant.

In some embodiments the method comprises injecting a growth enhancement medium into the tract.

In some cases the method comprises injecting a growth enhancement medium into tissue surrounding the tract.

The method may comprise the step of leading a drain through the tract. The drain may be led through a first opening in the tract. Alternatively or additionally the drain is led through a second opening in the tract.

In another aspect the invention provides an implant comprising a growth enhancing medium.

The implant may have a coating which comprises a growth enhancing medium. In some cases the implant is at least partially constructed from a growth enhancing medium.

In a further aspect the invention provides a drain such as a drainage drain which comprises a growth enhancing medium.

The drain may have a coating which comprises a growth enhancing medium.

The drain may be at least partially constructed from a growth enhancing medium.

In another embodiment the drain (or seton) is locked to the handle/driver mechanism during implantation (delivery of implant) to maintain traction. Once the implant is fully implanted the handle is decoupled (automatically or manually) from the drain (or seton). The excess drain material may be trimmed at the external surface of the closed tissue tract site at the surface of the rectum.

A drain (or seton) is held in a fixed position along the length of the tissue tract due to the compression at the internal opening. The implant opening compresses the tissue opening around (onto) the drain, locking it into place. The drain may have a specialty designed/located compression zone and may have corresponding features to facilitate the anchoring of the drain in this zone.

The drain is fixed in place due to the compression forces of the internal tissue tract being compressed inwardly by the radial forces applied by the implant.

To further enhance fixation of the drain and prevent the drain from moving out of the tract distally or proximally the drain may be constructed with locking features such as a knot 831 along the entire length, partial length, and defined/predetermined compression zone at the site of the implant tissue compression, or any combination of these.

Knots may be implemented along the length of the drain or at a specific location such as that of the implant compression zone.

Spheres, cylinders, triangles and other multifaceted shapes may be provided such as by moulded over along the length of the drain or at a specific location such as that of the implant compression zone.

To enhance the anchoring of the drain barbs may be incorporated along the length of a drain or at a specific location such as that of the implant compression zone. The barbs may face in both the external and internal opening directions to prevent motion in either direction.

To enhance the anchoring of the drain (or seton) quills may be incorporated along the length of the drain or at a specific location such as that of the implant compression zone. The quills may face in both the external and internal opening direction to prevent motion in either direction.

The drain may be constructed to act purely as a drain and/or as a scaffold to enhance tissue healing.

To provide enhanced drainage, the drain (or seton) may have a plurality of peripheral holes and may include (pores). The shape of the drain in cross section may be selected from one or more of round, oval, star and cross. The drain is constructed to be bioabsorbable.

An example of potential materials include: PLA and PLGA (poly(lactic-co-glycolic acid)) (PLGA, PCL, Polyorthoesters, Poly(dioxanone), Poly(anhydrides), Poly(trimethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials.

The shape is designed to enhance the drainage of the residual tract. The shape may also act as a scaffold to improve/enhance the healing of the tract.

The plurality of peripheral holes/pores enhance drainage of the tract to prevent the drain/drain from blockage.

To enhance scaffolding, the plurality of peripheral holes/pores may serve as a structure of a scaffold that enhances tissue integration and improves wound healing of the tract.

A variety of materials may be used as a tissue scaffold that enhance and improve tissue wound healing. Many of these materials are bioabsorbable polymers or natural tissue materials. An example of potential materials include: PLA and PLGA (poly(lactic-co-glycolic acid)) (PLGA, PCL, Polyorthoesters, Poly(dioxanone), Poly(anhydrides), Poly(trimethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials.

The invention also provides a mechanism to stabilise the tissue during the delivery of the implant to prevent bunching and twisting of the mucosal layer during delivery of the implant. By preventing such tissue interaction, the delivery forces may be reduced and a more reliable and repeatable depth of delivery may be achieved.

One mechanism of stabilising the mucosal tissue is achieved by utilising a hollow overtube. The overtube interfaces onto the surface of the mucosal lining and may stabilise the tissue prior to and during the delivery of the implant using one or more of the following mechanisms:

Pressure—the trumpet may be spring loaded or otherwise to apply pressure to the mucosal surface. The pressure may be manual force from the user's application of the delivery mechanism while abutting to the mucosal surface Spike type features. The surface of the trumpet that interfaces to the mucosal surface may contain features that penetrate into the mucosal surface and hence prevent rotation or twisting of the mucosal lining. These features may be in the form of:

Needles

Microneedles

Micro-spikes

Castellated features (similar to the features of a rook in a chess set)

The features may be incorporated into the trumpet by means of:
Overmoulding
Injection moulding
Press fit
Surface treatment
Rubberised surface
Surface modification
Surface roughening (sand blasting etc.).

The implant may be doped or loaded with healing and antimicrobial agents (such as stem cell, silver ions, silver particles, antibiotics, antibacterial agents and the like).

The driver coil and/or implant system described herein may be useful for closing various types of tissue defects, including a perianal fistula, other types of fistula in other locations in a body, or a sinus. The devices described may be used for joining tissues together.

The driver coil and implant system described may be useful for closing various types of tissues defects, other types of fistula in other locations in a body, other sinuses, or joining tissues together. Examples of suitable applications include, but are not limited to: treatment of esophageal varices, recto-vaginal fistula repair, treatment of diverticulitis, tightening of sphincteric junctions: e.g. tightening of gastro esophageal junction for treatment of gastro esophageal reflux disease, tightening of anorectal sphincter for treatment of faecal incontinence, tightening of pyloric sphincter for treatment of obesity of other gastro intestinal conditions. Other applications may include; repair of patent foramen *ovale* (PFO) or atrial septal defect, left atrial appendage closure, closure of fallopian tube for sterilisation, vas deferens blockage for male sterilisation, tissue repair due to trauma e.g. puncture trauma due to piercing, post-surgery trocar site closure, apposition of tissue for treatment of obesity during bariatric surgery.

The majority of perianal fistula have an internal opening less than 1 mm in diameter.

In the case of perianal fistula we have found that a driver coil ID of 4 mm to 6 mm ensures that adequate tissue margin surrounding the internal opening is captured so that the implant will not pierce through the fistula tract and that the implant has an adequate amount of tissue to compress against the tract lumen to provide a secure tract closure.

We have found that the driver coil OD is preferably in a range of 6 mm to 8 mm so that only a small amount of extra tissue is involved in the procedure. In this way the device avoids unnecessarily disrupting healthy tissue.

We have found that the wall thickness of the driver coil is preferably 0.5 mm to 1 mm. If the wall of the driver coil is too thick the puncture defect is larger than needed and will increase the amount of driver force required to deliver the implant into the tissue. A larger wall thickness may also rip the tissue instead of creating a uniform tract that the implant will reside in.

We have also found that the driver coil pitch is preferably between 2 mm to 4 mm. If the pitch is too long the coils become too elongated and will not form a "hoop" around the tissue tract and will not be able to compress the tract closed. If the pitch is too short tissue will become caught between the driver coil struts, which may result in deformation, binding, and/or un-straighten the direction of the driver coil travel.

The strut height is preferably in the range 0.5 mm to 2 mm.

The implant ID preferably has a distal range from 1 to 6 mm and a proximal range from 0.5 to 2 mm.

The pitch of the implant will mimic the driver pitch.

Referring for example to FIGS. 101 to 127 there is illustrated a delivery device for an implant such as the implant described above.

The delivery device comprises a driver coil 900 and a drive shaft 901 for the driver coil 900. The driver coil 900 engages an implant 902. The driver shaft 901 is movable from a retracted loaded configuration to an extended delivery configuration. The shaft 901 in this case is rotatable in a delivery direction for movement between the loaded and delivery configurations. While the shaft 901 is being moved for delivery of the implant, the shaft 901 is prevented from rotation in a direction which is opposite to the delivery direction.

When the implant 902 has been delivered, the shaft 901 is movable from a delivery configuration to a retracted configuration in which it is disengaged from the implant 902. In some cases the delivery direction is a clockwise direction and the disengaged direction is a counter clockwise direction. On movement between the loaded configuration and the delivery configuration, the shaft 901 travels a first distance and on movement between the delivery configuration to the disengaged retracted configuration, the shaft travels a second distance greater than the first and is is free to rotate in a counter-clockwise direction. This allows tissue to be released from the driver coil 900 as the driver coil 900 is being retracted.

The delivery device comprises a housing 910 for the delivery coil and the drive shaft 901. The housing 910 comprises a grip portion 911 and a tube 912 extending from a distal end of the grip portion 911. The tube 912 comprises a distal bend 913 to assist in directing the implant for delivery at the site of interest. At least a portion 915 of the drive shaft 901 may be flexible to account for the outer tube bend.

The delivery device comprises a distal overtube 914 which has distally projecting tissue. Stabilisation features 917 which in this case are provided by surface features such as castellations at the distal end of the overtube 914.

Figure 111:
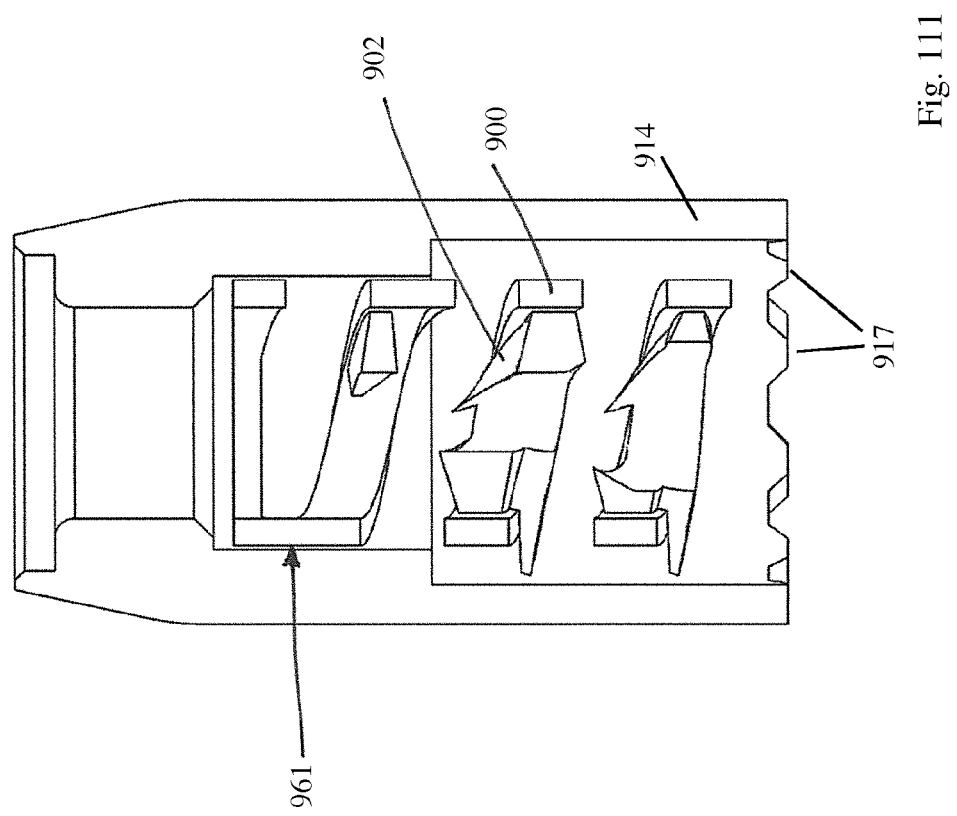
FIG. 111 illustrates the driver coil supporting the implant in a retracted configuration.

The delivery coil 900 and the implant 902 are constrained on-axis with the overtube 914 to prevent non-concentric delivery relative to the fistula tract. Referring to FIG. 111, it will be noted that the driver coil 900 is supported by an on-axis shoulder 961 so that the driver coil 900, and hence the implant 902, engages perpendicular to tissue during movement from the retracted configuration to the delivery configuration.

The delivery device also comprises a rotary knob 915 for manually rotating the shaft 901. There is a releasable lock 916 to prevent undesirable rotation of the shaft 901 prior to appropriate location and orientation at the tissue site of interest (e.g. accidental delivery of the implant when removing from packaging).

The delivery device also comprises a mounting element 920 (or centering member) comprising a distal loop 921 for mounting a drain 925 to the lock element 916. The mounting element 920 is movable with the shaft from a loading configuration for mounting a drain 925 to the mounting element 920 to a retracted configuration.

Figure 112:
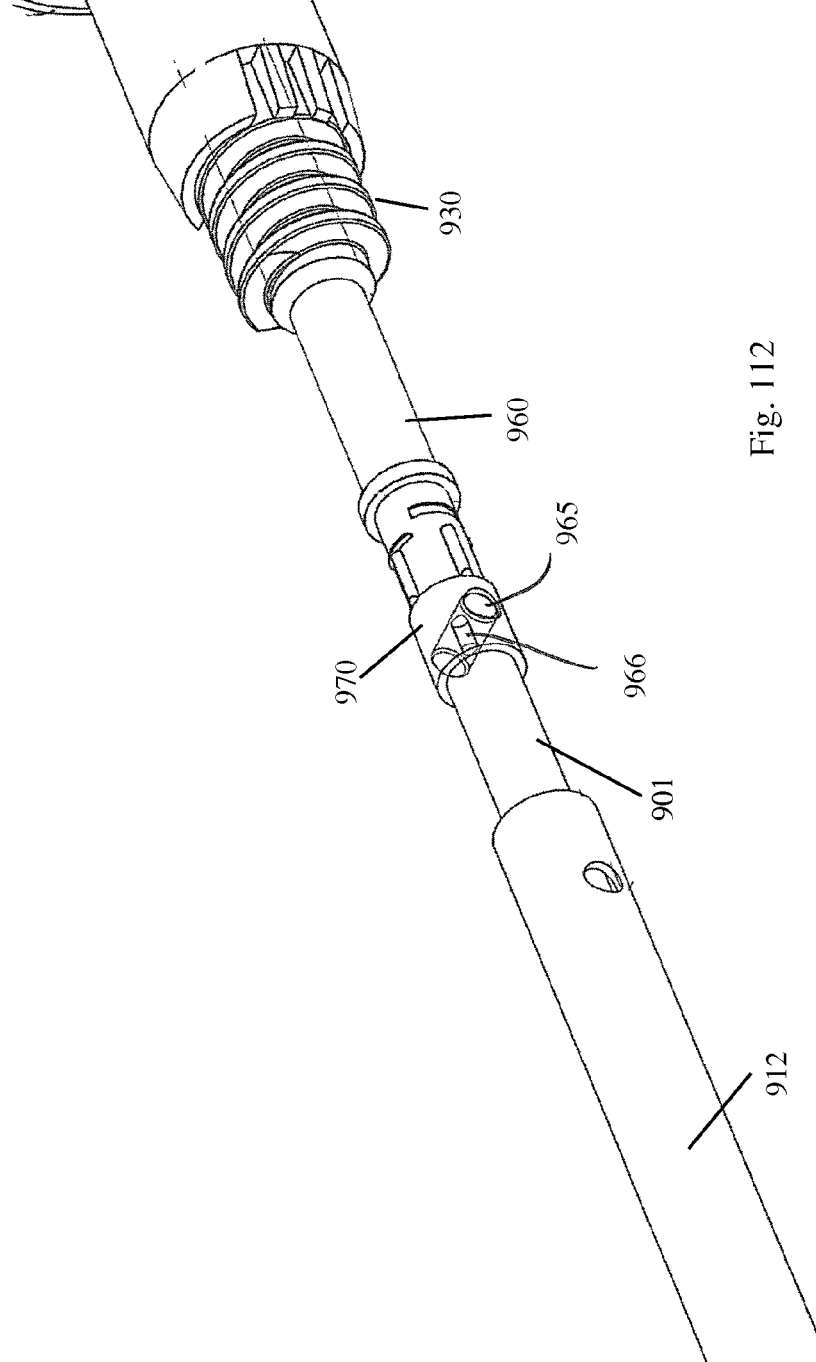
FIG. 112 is an enlarged view of a detail of the delivery device.
Figures 113, 114:
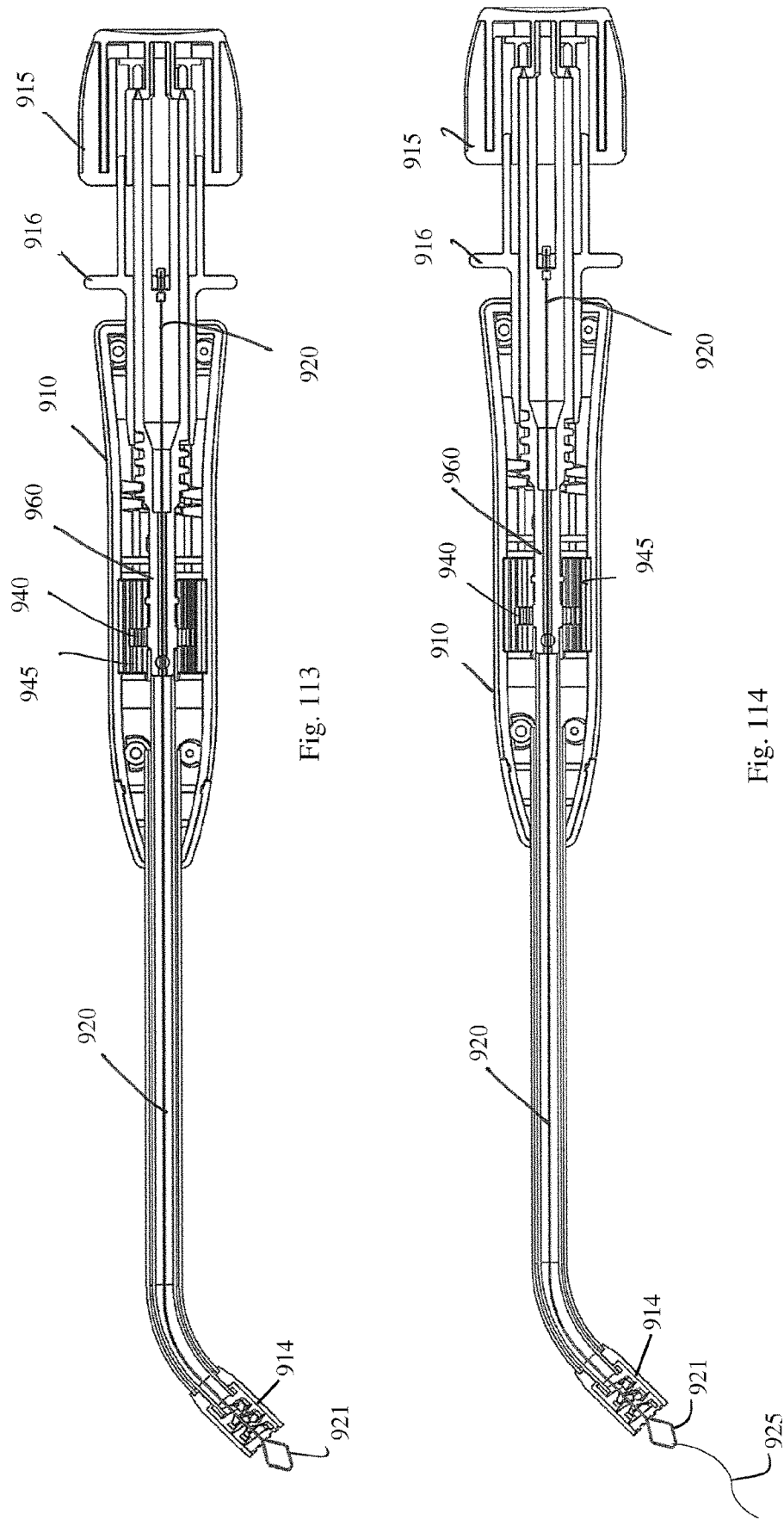
FIGS. 113 to 116 illustrate the delivery device and the implant in different configurations of use.
Figure 115:
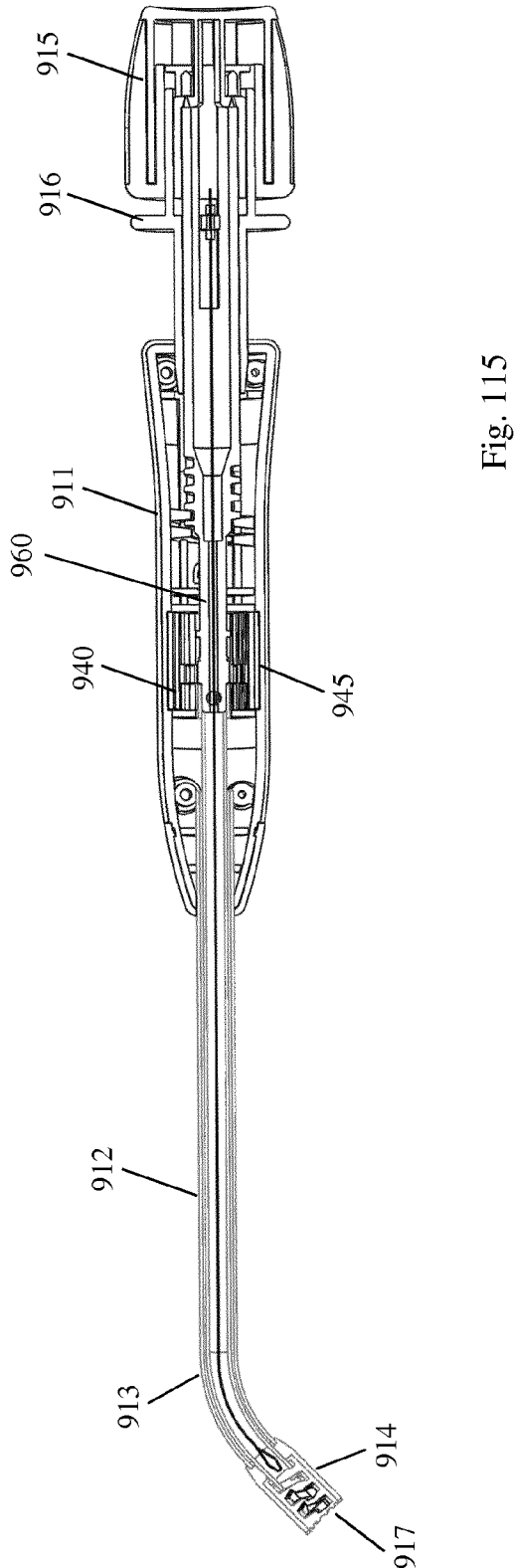
Figure 116:
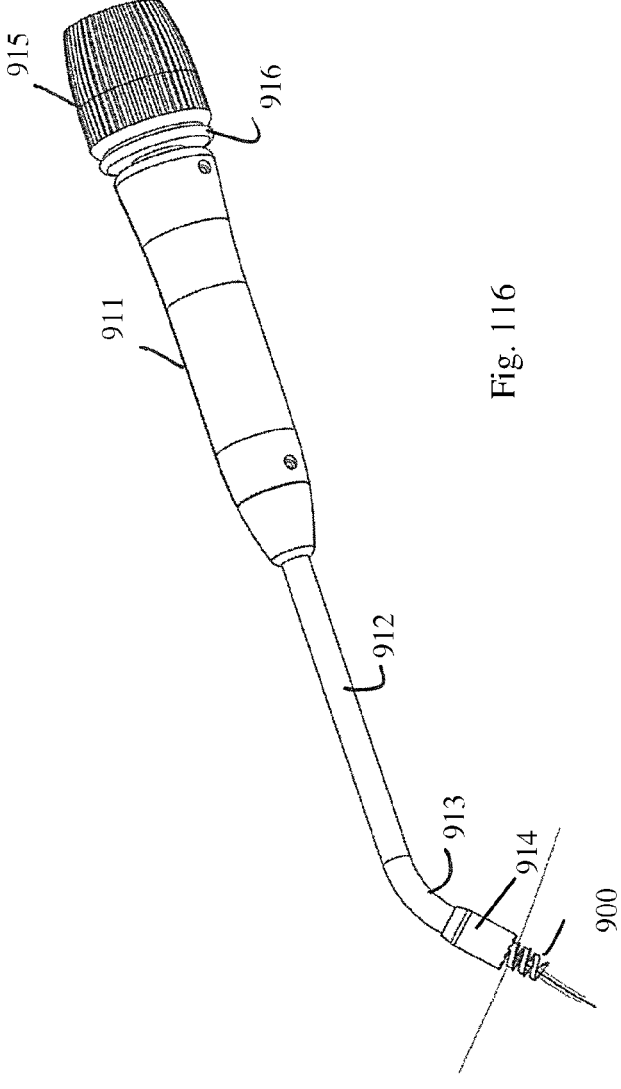
Figure 117:
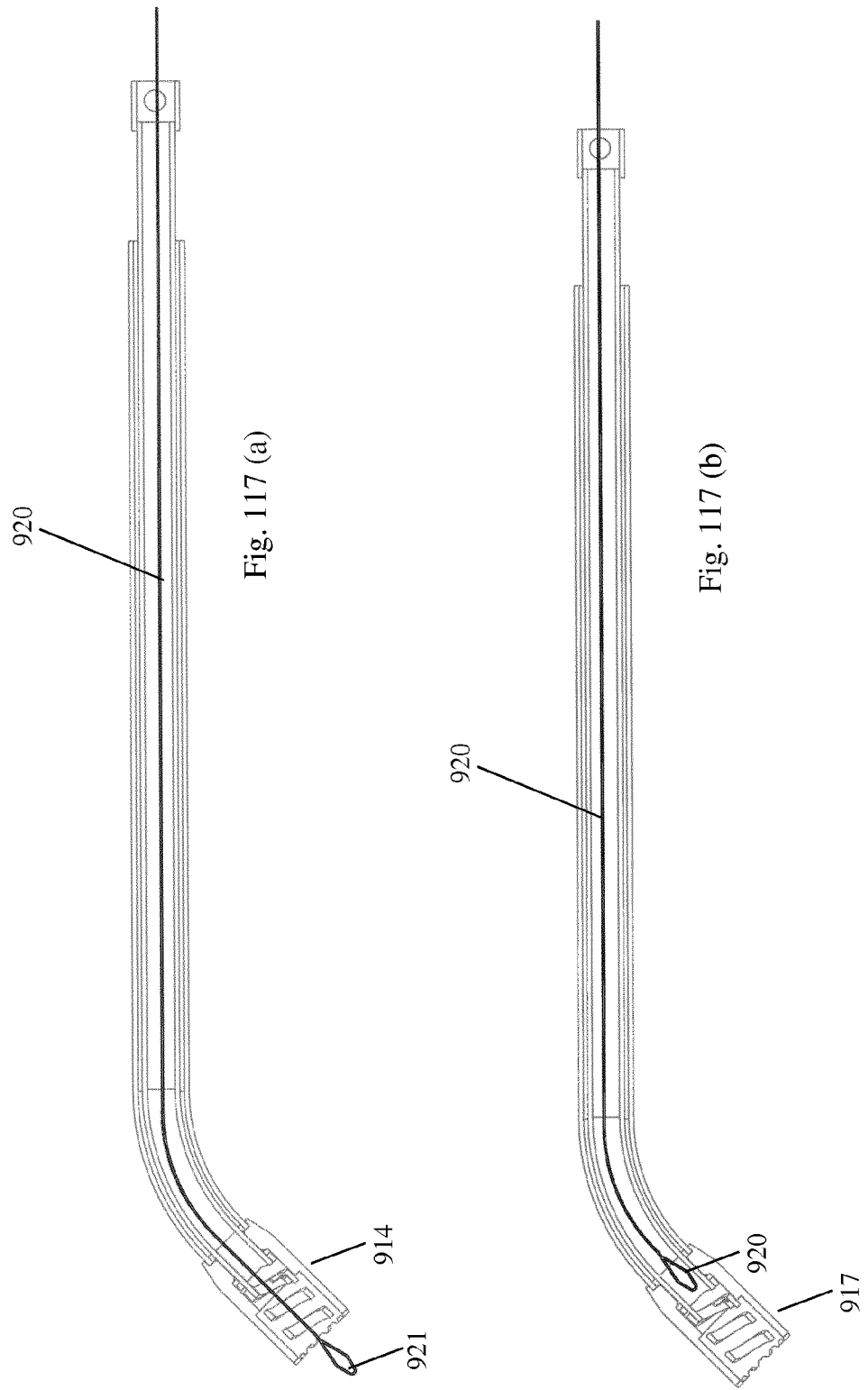
FIGS. 117(a) and 117(b) illustrate shaft parts of the delivery device with a suture capture device in different positions of use.
Figure 118:
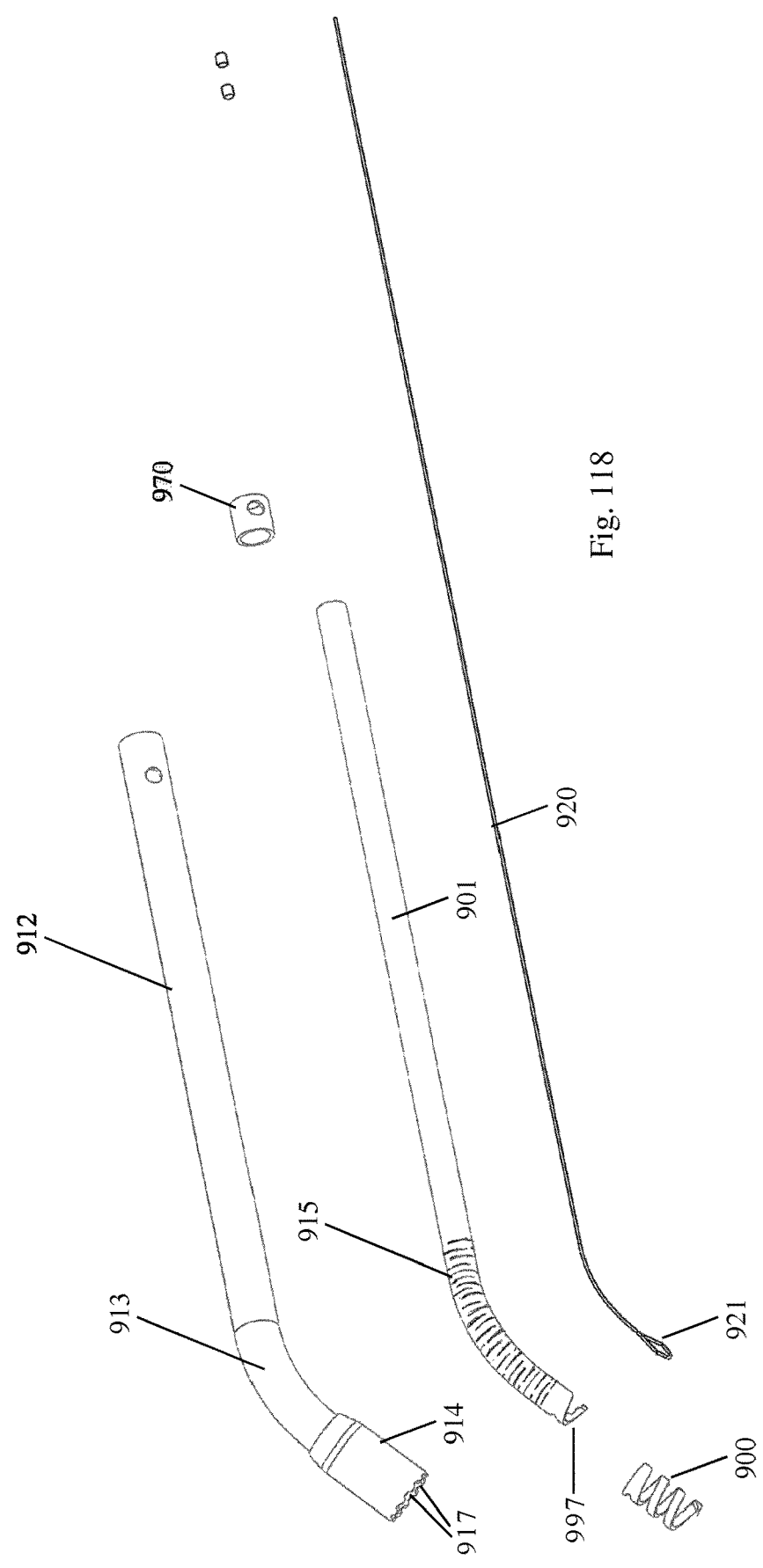
FIG. 118 is an exploded view of the shaft parts of FIG. 117(a)
Figure 119:
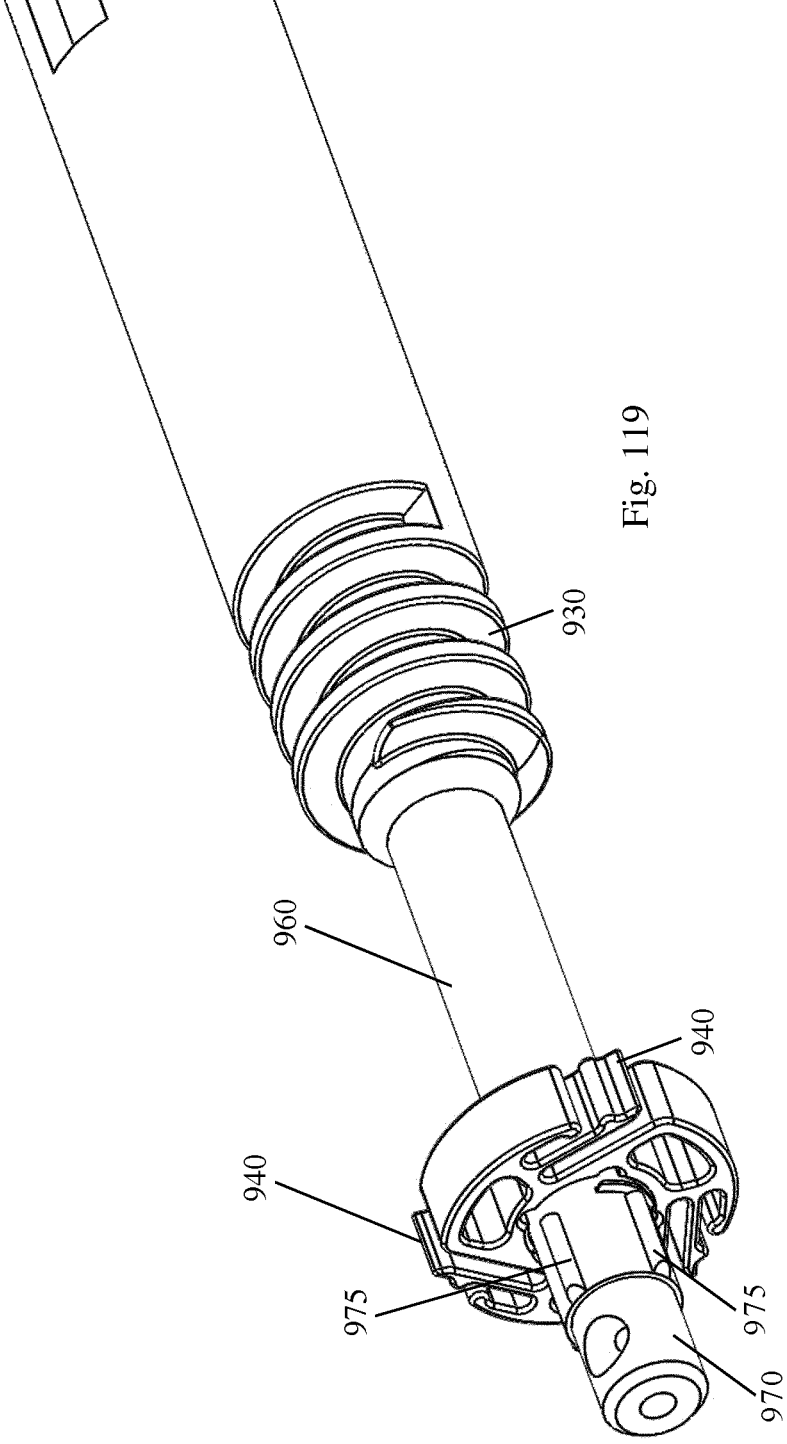
FIGS. 119 and 120 are enlarged views of a pawl and ratchet detail of the delivery device with the pawl in different positions of use.
Figure 120:
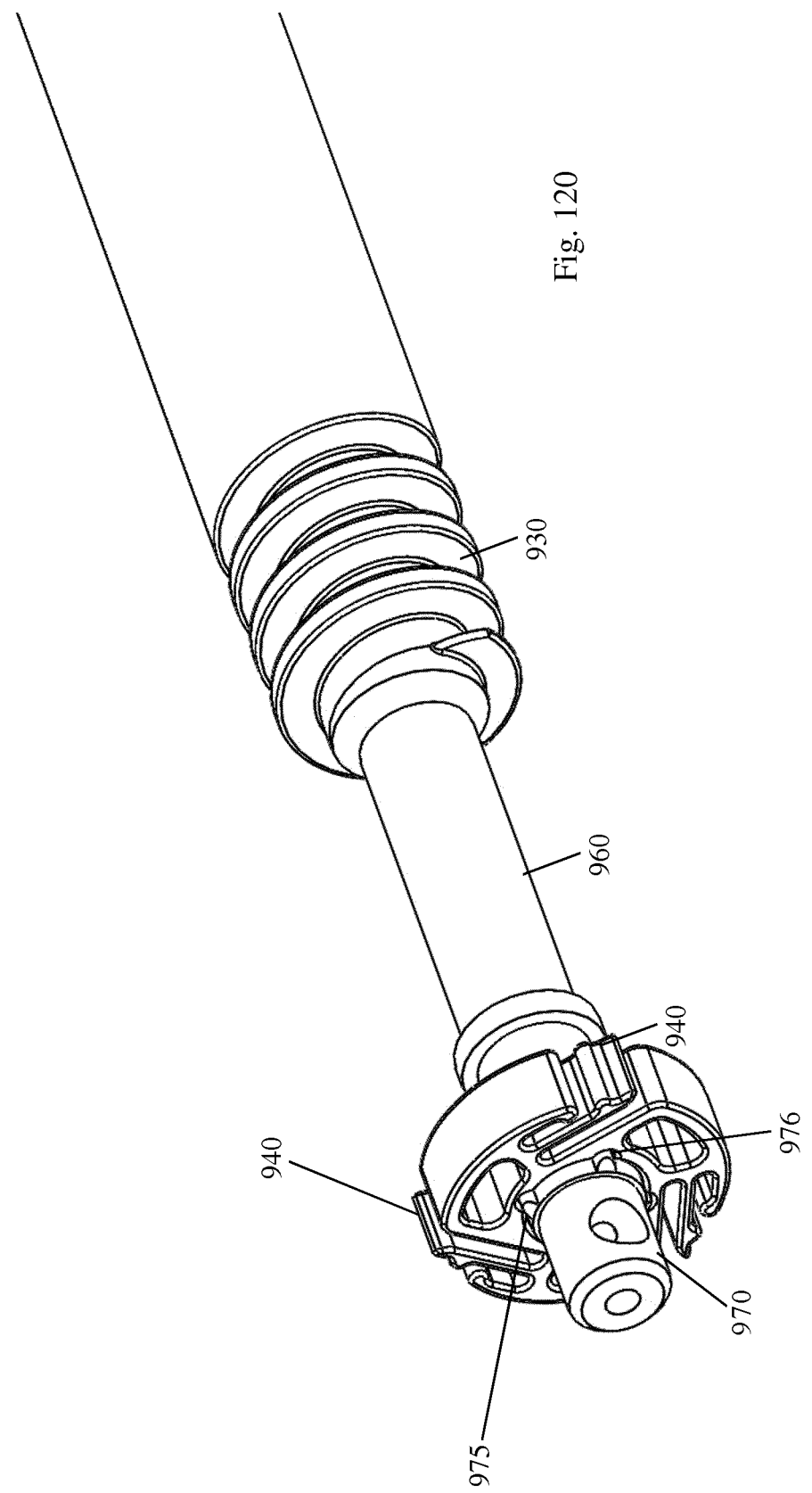
Figure 121:
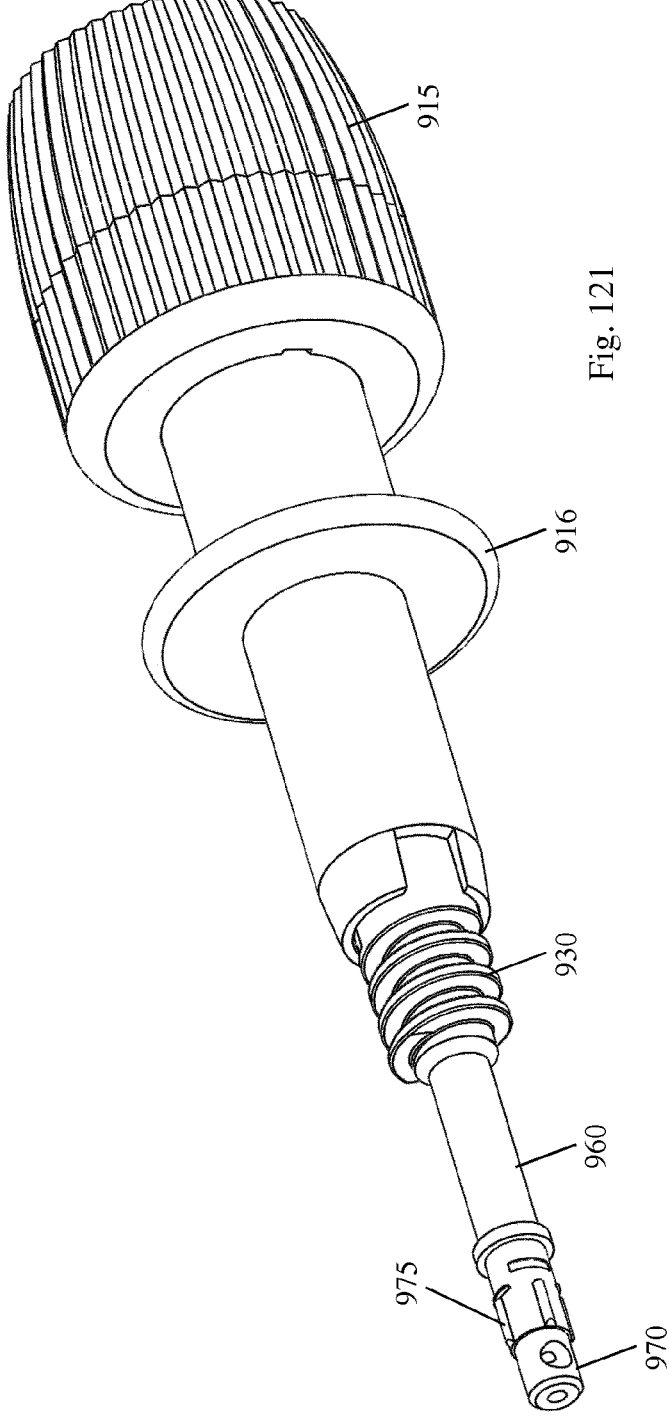
FIG. 121 is an enlarged view of a handle end of the delivery device.
Figure 122:
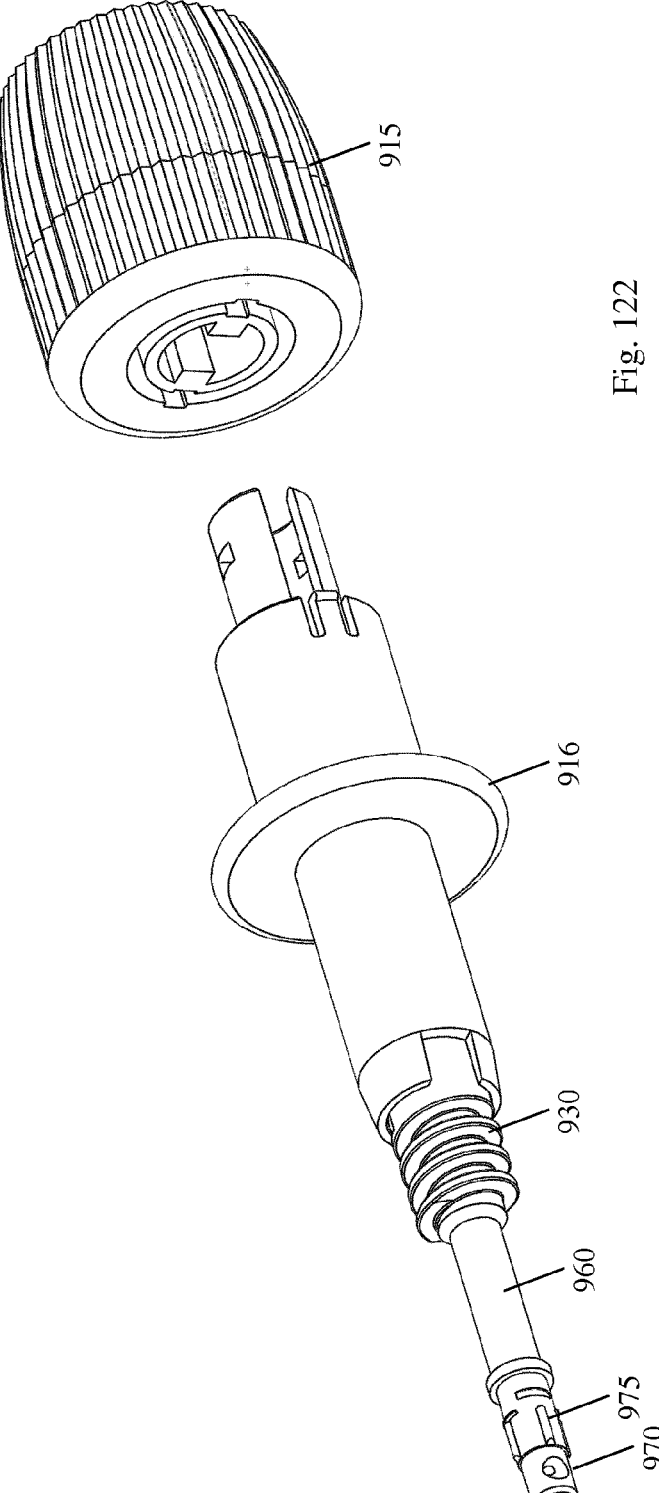
FIGS. 122 to 127 are views of elements of the handle end of the delivery device.
Figure 123:
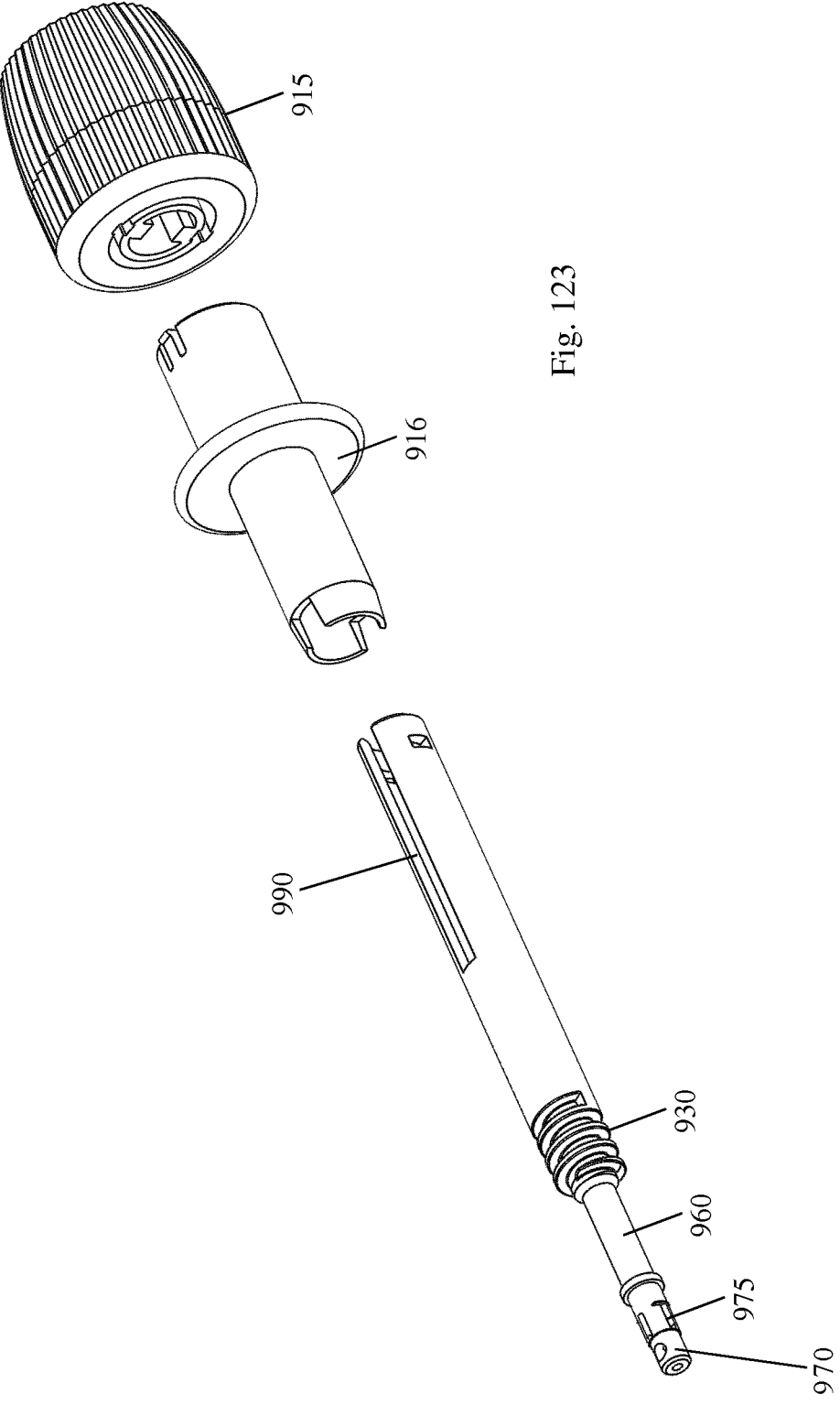
Figures 124, 125:
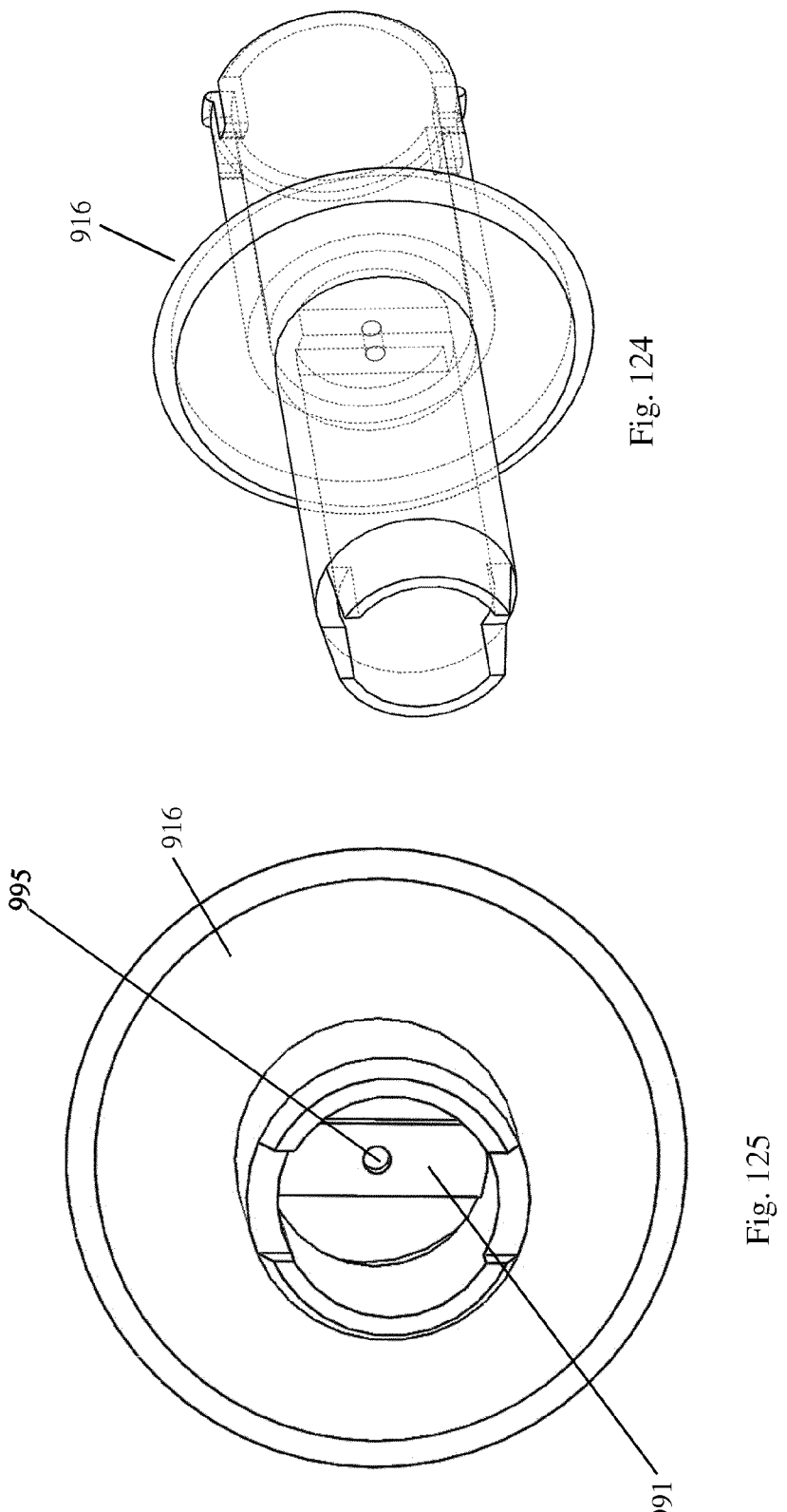
Figure 126:
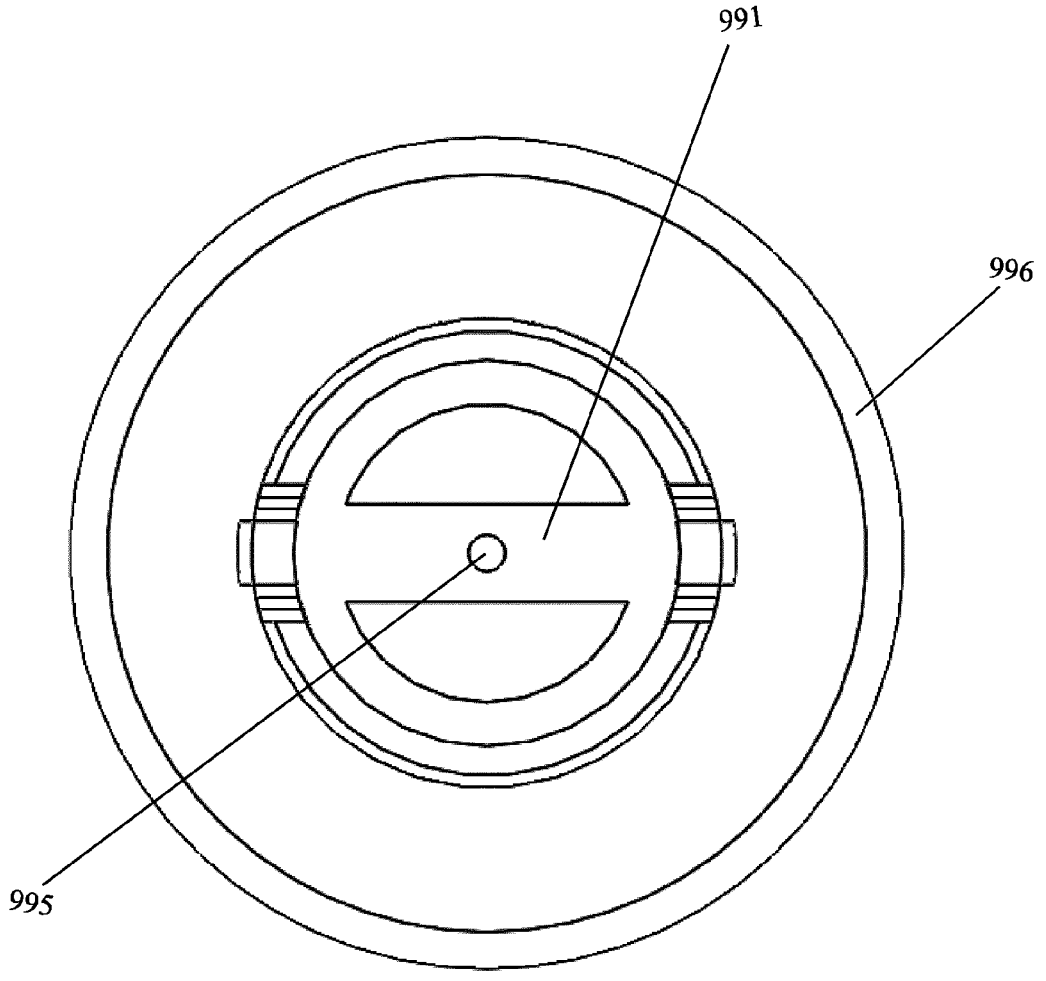
Figure 127:
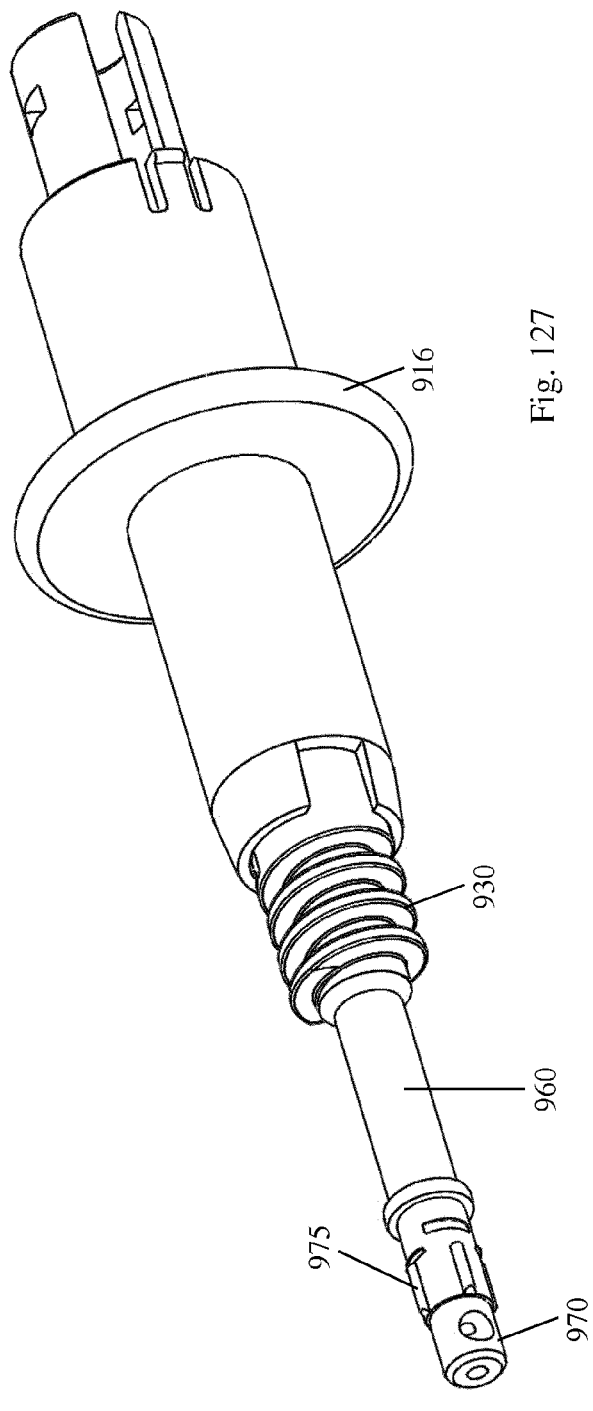
Figure 130:
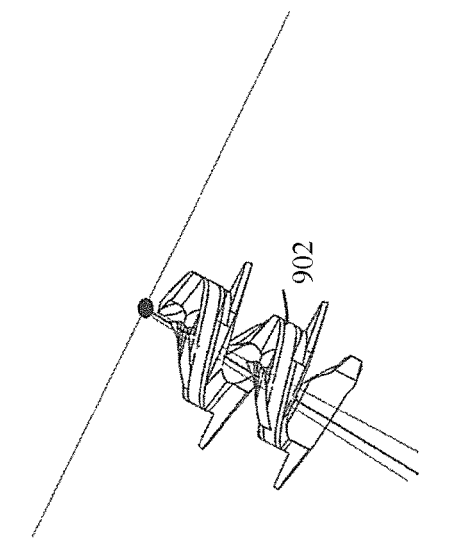
FIGS. 128 to 130 show the deployment of the implant.
Figure 129:
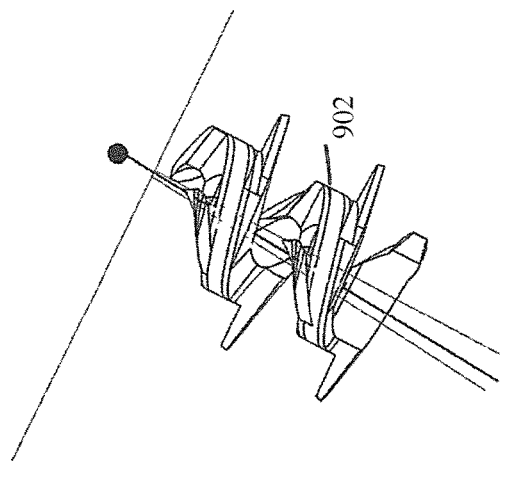
Figure 128:
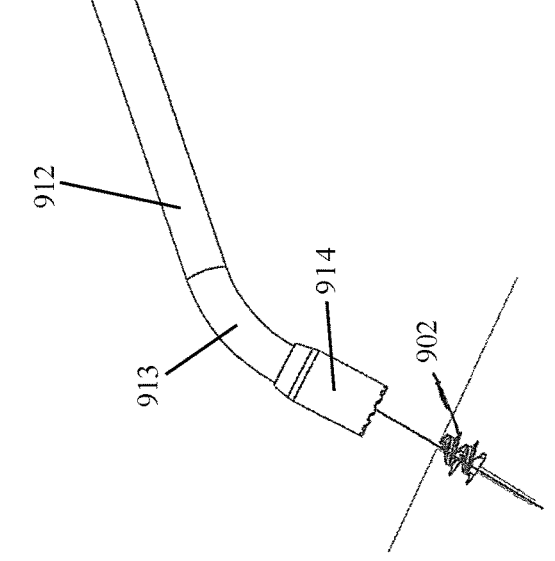

In one case the device shaft 901 has a proximal extension 960 which extends towards the rotary knob 914. The extension 960 is joined to the drive shaft 901 by a collar 970. Referring in particular to FIG. 112, a cross pin 965 extending through the collar 970 is used to connect proximal extension 960 to drive shaft 901. The drive shaft 901, collar 970 and cross pin 965 may be of metal and the proximal extension 960 may be of plastic. The cross pin 965 has a through hole 966 to allow the drain mounting element 920 to pass therethrough.

Functionally the implant is delivered as follows:

Step 1: A suitable length of drain material 925 (e.g. Size 2/0 absorbable suture) is looped through the suture capture loop 921 and either tied off, or looped though to provide a double strand drain 925. This drain 925 is then attached to the seton, brush, probe or similar, that is in place occupying the fistula tract. The device is led into place by retraction of the drain 925 through the external opening as previously described.

Step 2: Once the device is in place (with the implant and driver coil positioned concentrically around the fistula Internal opening), the lock 916 is disengaged by pulling the lock component 916 towards the rotary handle 915.

Step 3: The rotary handle 915 is now turned in a clockwise ('CW') rotation to deliver the implant 902. The rotary handle 915 is rotated until it bottoms out and is not capable of further rotation. It will be noted that the rotary handle 915 may not be rotated in a counter clockwise ('CCW') direction until the implant 902 has been fully delivered and the ratchet mechanism consisting of pawl gear 940 and of radial ratchets 945 has been disengaged.

Step 4: The rotary handle 915 is rotated in a CCW direction to disengage the implant 902 from the delivery coil 900 and remove the delivery coil 900 from the tissue. The rotary handle 915 may be turned as many turns in a CCW direction as necessary to disengage the delivery coil 900 from the tissue.

Step 5: The delivery mechanism is pulled away from the tissue, leading the drain 925 through the fistula internal opening. The drain 925 is then cut from the delivery handle and a knot is tied. The drain 925 is pulled through the external opening until the knot is snug against the implant 902—lodging the drain 925 in place.

The following aspects of the delivery mechanism are particularly important:

1. Rotational to On-Axis Linear Movement

The handle 915 turns on a screw thread 930, the pitch of which is identical to the pitch of the coil of the implant 902. Hence, by turning the handle 915 the implant 902 is both rotated and driven forward by the delivery coil 900 into tissue.

2. Pre-Delivery Lock

A lock 916 is provided to prevent inadvertent delivery (rotation of the handle).

Figure 103:
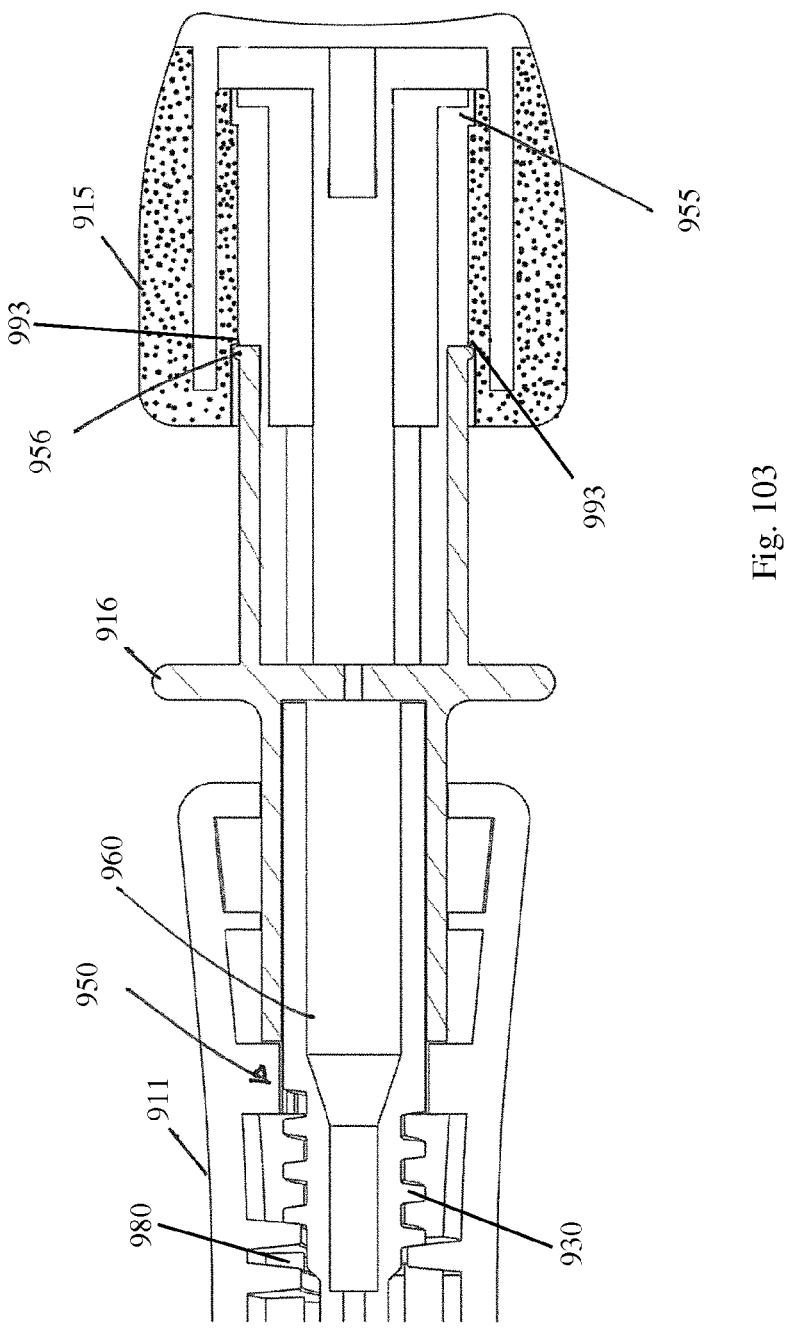
FIG. 103 is an enlarged view of part of the handle end of the delivery device.

The lock 916 is keyed to the rotational shaft at via slot 990 of the rotational shaft and cross bar element 991 of the lock 916 (FIG. 103). It will be noted that the rotational shaft is attached to the delivery handle via male thread form 930 and corresponding female thread form 980. In the locked state, the distal end of the lock 916 is engaged with the handle body preventing rotation of the delivery handle. To unlock, the lock 916 is pulled back towards the handle 915, disengaging the interference with the handle body. The delivery handle 915 is then free to rotate.

The lock 916 has a second purpose, as the suture capture wire 920 is fastened to the lock component 916. When the lock is retracted (by e.g. 20 mm), the suture loop 921 is pulled proximally to the implant. A bump feature 956 prevents inadvertent disengagement of the lock via interference with shoulder 993 of handle 915. This bump feature 956 is overcome when the user applies force. The bump feature 956 snaps into a recess 955 when the lock is fully released preventing reengagement of the lock 3. Premature Retraction Prevention The handle 915 is prevented from being turned in a CCW direction prior to complete delivery of the implant 902. When the handle 915 is turned in the CCW direction, the barbs of the implant 902 lock into tissue and release the implant from its delivery lock 997. If this happens prior to complete delivery, the implant may be released from the delivery mechanism in a partially delivered state.

To prevent this condition, a ratchet mechanism is employed to only allow CCW rotation after full delivery of the implant. The ratchet mechanism (FIG. 106) consists of a pawl gear 940 which is keyed to the rotational shaft 960 (for example by splines 975 that travel in corresponding elongate grooves 976 in the pawl gear 940) and rotates on a set of radial ratchets 945. The pawl 940 rotates and moves linearly with the delivery shaft 901 until, just prior to complete delivery of the implant 902, it interfaces on a shoulder 946 which pushes it over bump 996 and off the keyed area of the shaft. The pawl gear 940 is now free to spin on the shaft 901 and hence allows CCW rotation.

Figures 104, 105, 106:
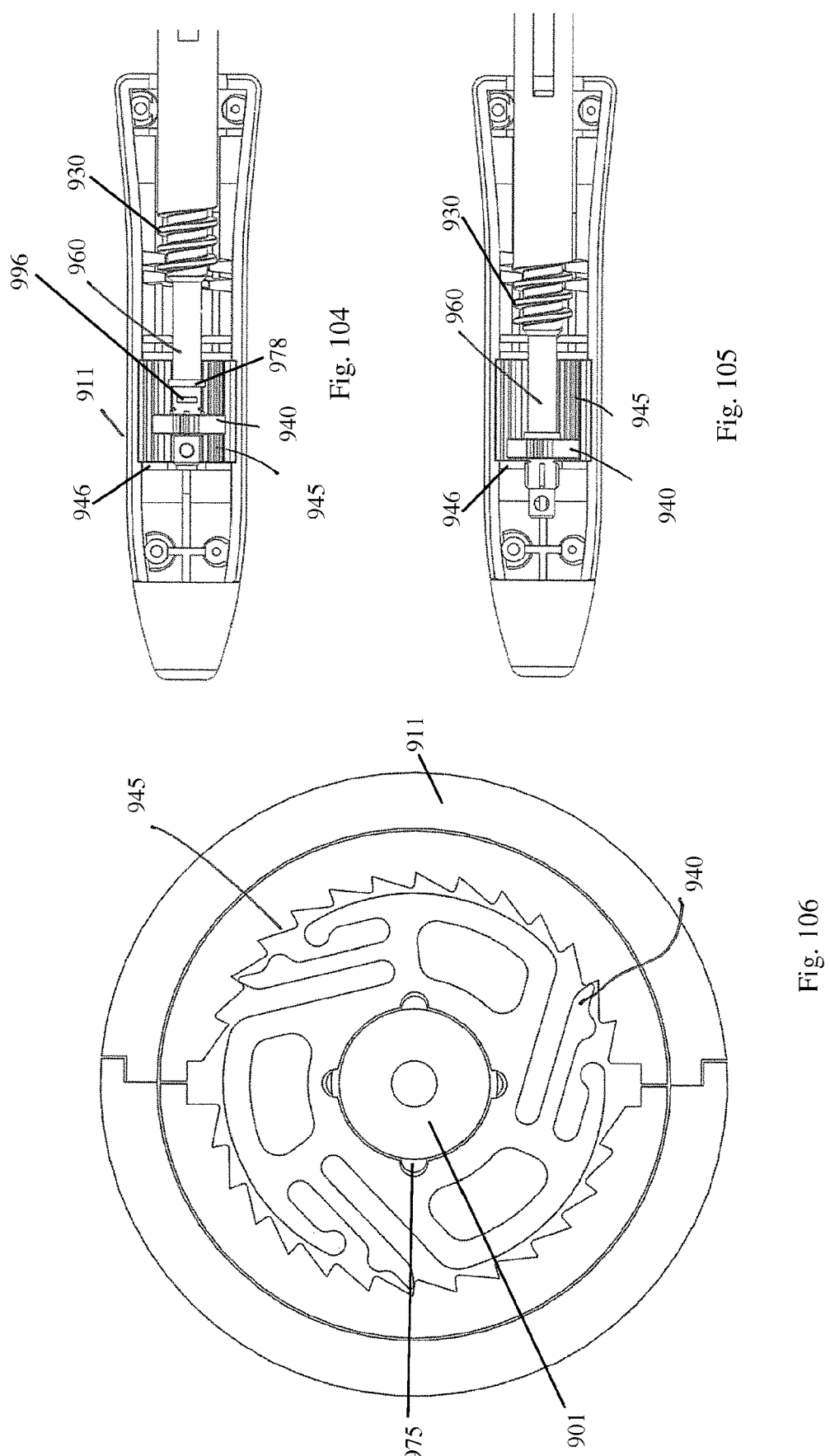
FIGS. 104 and 105 are cross sectional views of part of the delivery device in different configurations of use.
FIG. 106 is an enlarged view of a ratchet and pawl system used in the delivery device.
Figure 108:
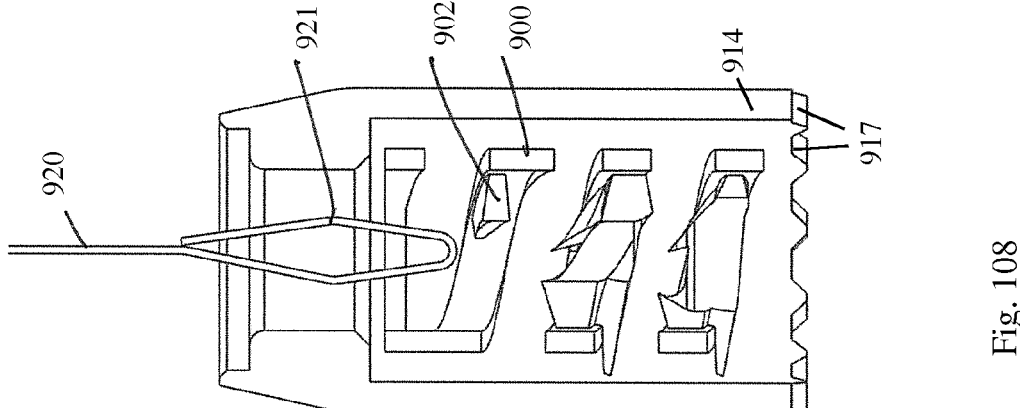
FIGS. 107 and 108 are cross sectional views of a distal end of the delivery device with a mounting element for a drain in different configurations.
Figure 107:
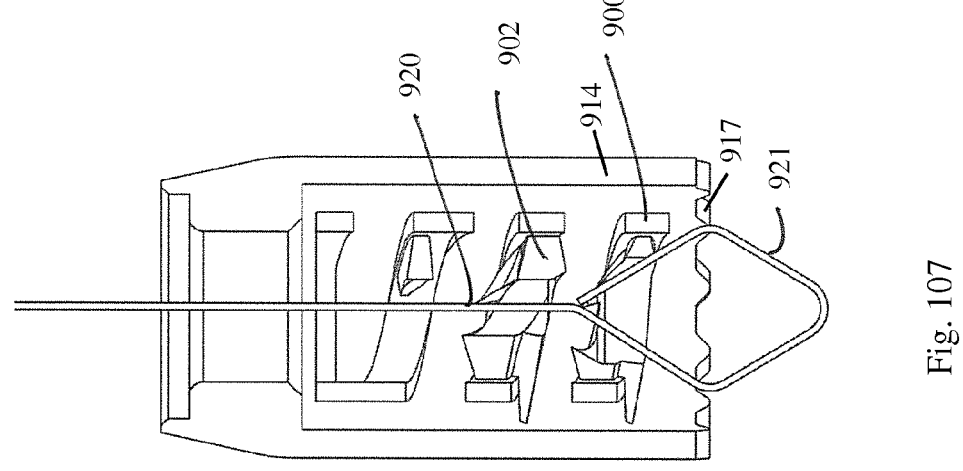
Figure 110:
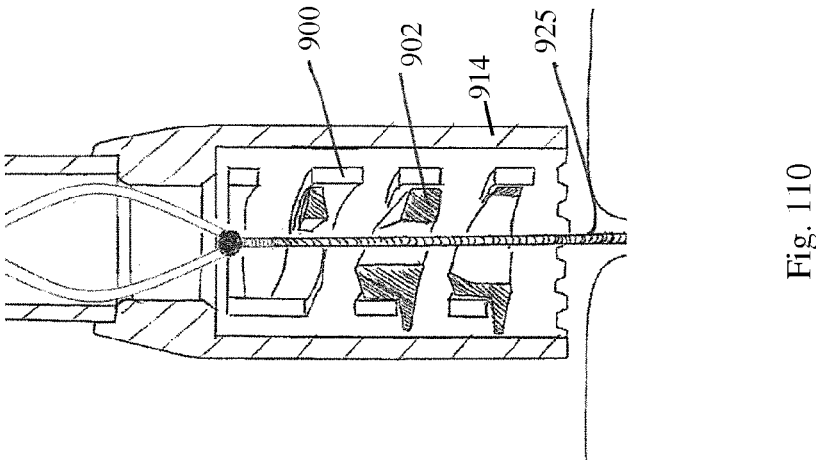
FIGS. 109 and 110 illustrate the use of the mounting element attached to a drain.
Figure 109:
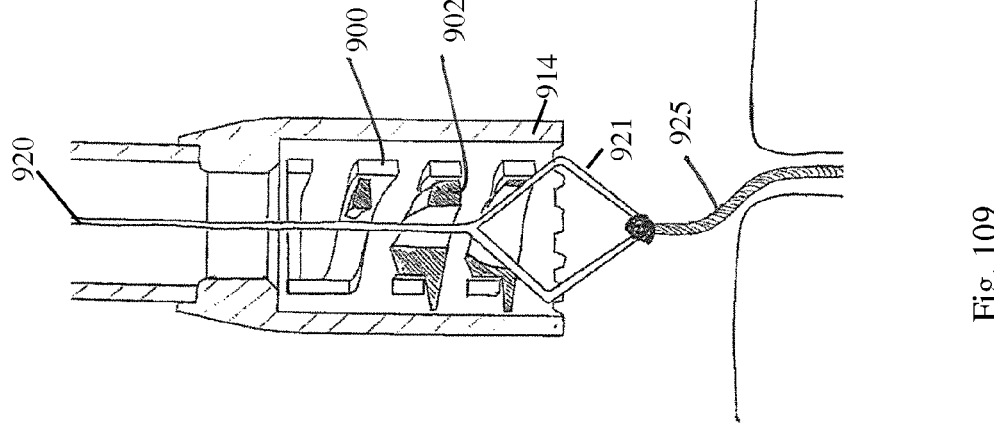

Referring to FIG. 104, it will be noted that the pawl 940 is keyed to the shaft 901 as it rotates clockwise. This prevents rotation in an anticlockwise direction.

Referring to FIG. 105, when the full distance of travel is reached, the pawl 940 is pushed off the key by engagement with the shoulder 946, allowing anticlockwise rotation.

The pawl gear 940 is held in place by collar 978 and bump 996 after disengagement of the ratchet mechanism post implant delivery.

4. Drain Capture/Mounting Element 920

A drain capture wire/mounting element 920 is provided to allow attachment of a suitable drain 925 (such as an off the shelf absorbable suture) prior to use. The drain capture wire 920 is pulled into the outer tube by activation of the lock 916, so as the wire loop 921 and the suture knot are pulled proximal to the implant 902 preventing fouling and preventing interference of the wire 920 to the tissue during implant delivery. The drain capture element may comprise a loop, hook, cleat, ball or diamond shape.

The capture wire 920 extends through the shaft 901, the shaft extension 960, and through a hole 995 in the lock cross bar element 991. The wire 920 is retained by the cross bar element 991 by any suitable means such as an enlarged element or part of the wire 920 proximal of the hole 995 which prevents the proximal end from passing through the hole 995.

The drain may also be preassembled during manufacture of the system wherein the drain is tied to the drain mounting element prior to use.

5. Post Retraction 'Free-Spin'

It was found in animal and cadaver testing, that in some cases, additional CCW turns of the delivery device were needed in some cases to dislodge any tissue that may have become lodged or captured on the delivery coil 900, e.g. while three clockwise turns are used to fully deliver the implant 902, four turns or more in reverse may be required to fully disengage the driver coil 900 from the tissue.

A mechanism has been incorporated to facilitate the required additional CCW rotation. The drive shaft thread 930 and the corresponding female thread forms 980 in the handle body are designed to disengage from each other on full retraction. The handle, drive shaft, and driver coil are now in a state of 'free-spin' whereby infinite counter clockwise rotation is facilitated.

The delivery system of the invention may be used in other applications such as in the treatment of a fistula other than a perianal fistula. Examples include rectovaginal fistulas, enterocutaneous fistulas, enteroenteral fistula, gastric fistula. It may also be used in other applications such as, bone anchor fixation (e.g. bone screws), suture fixation devices, bone pins, wound closure (e.g. Muscle, integument, fascia or other tissue defects), stent delivery, pilonidal or other sinus closure, closure of bodily vessel, fluid lumen or other repair of anatomical defects or damage, delivery of coiled implants (e.g. neurological, bio-electrical), delivery of clot removal structures or devices, traversing lumen blockages (e.g. chronic total occlusion of vessels), delivery of drug delivery scaffolds or coils, maxillofacial applications (e.g. muscle tightening, delivery of anchoring devices for cosmetic applications), delivery of devices for muscle tightening (e.g. faecal incontinence), tendon or ligament reattachment.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described, which may be varied in construction and detail.

The invention claimed is:

1. A method of delivering an implant to an opening in a tissue using a delivery device, the delivery device including a centering member and a handle assembly including a rotary member, the method comprising:

attaching a seton or suture to the centering member via a centering member loop located at a distal end of the centering member;

applying tension to the seton or suture via the delivery device;

centering the delivery device with the centering member with respect to the opening in the tissue based on the tension applied to the seton or suture, the centering member being a separate element from the implant and that extends through the delivery device and through the implant;

rotating the rotary member of the delivery device in a first direction to rotate the implant and drive the implant into the opening in the tissue; and rotating the rotary member of the delivery device in a second direction to disengage the implant.

2. The method of claim 1, wherein the handle assembly further includes a lock, and the method further comprises:

unlocking the rotary member by movement of the lock to an unlock position, wherein the unlocking retracts the centering member towards a proximal end of the delivery device.

3. The method of claim 1, wherein movement in the second direction is prohibited until a predetermined number of rotations of the rotary member.

4. The method of claim 3, wherein the predetermined number of rotations corresponds to a bottoming out of the rotary member or a predetermined delivery depth of the implant.

5. A method of delivering an implant to an opening in a tissue using a delivery device, the delivery device including a driver coil engaging the implant and a handle assembly including a lock and a rotary member, the method comprising:

attaching a seton or suture to a centering member via a centering member loop located at a distal end of the centering member, the centering member being a separate element from the implant;

positioning the driver coil of the delivery device and the implant adjacent to the opening in the tissue with the centering member that extends through the delivery device and through the implant;

centering the seton or suture based on applying tension to the seton or suture via the delivery device;

unlocking the rotary member by movement of the lock to an unlock position;

rotating the rotary member of the handle assembly in a first direction to rotate the driver coil and the implant and drive the driver coil and the implant into the opening in the tissue; and rotating the rotary member of the delivery device in a second direction to disengage the implant from the driver coil and remove the driver coil from the opening of the tissue.

6. The method of claim 5, wherein the movement of the lock to the unlock position includes moving the lock toward the rotary member.

7. The method of claim 6, wherein rotating the rotary member also rotates the lock.

8. The method of claim 5, wherein the rotating the rotary member in the first direction both rotates the driver coil and translates the driver coil distally, and wherein movement in the second direction is prohibited until a predetermined number of rotations of the rotary member.

9. The method of claim 8, wherein the predetermined number of rotations corresponds to a bottoming out of the rotary member or a delivery depth of the implant, and wherein the predetermined number of rotations is identified by indicia on the handle assembly.

10. A method of delivering an implant to an opening in a tissue using a delivery device, the delivery device including a rotary member and a one-way rotation mechanism, the method comprising:

positioning the implant adjacent to the opening in the tissue using the delivery device with a centering member located adjacent to a distal end of the delivery device, the centering member being a separate element from the implant;

centering a seton or suture by applying tension to the seton or suture via the delivery device after attaching the seton or suture to the centering member via a centering member loop located at a distal end of the centering member;

unlocking the rotary member by movement of a lock along a longitudinal axis of the delivery device;

rotating the rotary member of the delivery device in a first direction while prohibiting rotation in a second direction, the rotating of the rotary member in the first direction being for a predetermined number of rotations to rotate the implant, drive the implant into the opening in the tissue, and disengage the one-way rotation mechanism to allow for rotation of the rotary member in the second direction; and rotating the rotary member of the delivery device in the second direction to disengage the implant from the delivery device and remove the delivery device from the opening of the tissue.

11. The method of claim 10, wherein unlocking the rotary member by movement of the lock along a longitudinal axis of the delivery device permits the rotation in the first direction.

12. The method of claim 11, wherein rotating the rotary member also rotates the lock.

13. The method of claim 10, wherein rotating the rotary member in the first direction both rotates a driver coil of the delivery device that engages the implant and translates the driver coil distally.

14. The method of claim 10, further comprising:
interfacing a pawl gear of the one-way rotation mechanism with a bump of a drive shaft to remove the pawl gear from a keyed area of the drive shaft.

15. The method of claim 10, wherein the predetermined number of rotations corresponds to a bottoming out of the rotary member or a predetermined delivery depth of the implant.

16. The method of claim 10, wherein the predetermined number of rotations is identified by an indicia on a handle of the delivery device.

17. The method of claim 10, wherein the positioning the delivery device and the implant adjacent to the opening in the tissue includes centering the delivery device with the centering member.

18. The method of claim 10, wherein the centering member is attached to the seton or suture provided through the centering member loop.

19. The method of claim 10, wherein the positioning includes the centering member having a portion extending through the opening in the tissue.

\* \* \* \* \*